(12) United States Patent
Gulati

(10) Patent No.: US 7,006,680 B2
(45) Date of Patent: Feb. 28, 2006

(54) SYSTEM AND METHOD FOR CHARACTERIZING MICROARRAY OUTPUT DATA

(75) Inventor: Sandeep Gulati, La Canada Flintridge, CA (US)

(73) Assignee: ViaLogy Corp., Altadena, CA (US)

( * ) Notice: Subject to any disclaimer, the term of this patent is extended or adjusted under 35 U.S.C. 154(b) by 16 days.

(21) Appl. No.: 10/430,664

(22) Filed: May 5, 2003

(65) Prior Publication Data

US 2003/0215867 A1 Nov. 20, 2003

Related U.S. Application Data

(60) Provisional application No. 60/377,520, filed on May 3, 2002.

(51) Int. Cl.
*G06K 9/00* (2006.01)

(52) U.S. Cl. ...................................................... 382/133
(58) Field of Classification Search ................ 382/128, 382/129, 133; 430/8, 21, 139, 503, 508, 511; 702/19, 21, 28; 600/309, 310, 336
See application file for complete search history.

(56) References Cited

U.S. PATENT DOCUMENTS

| | | | | |
|---|---|---|---|---|
| 5,371,669 A | 12/1994 | Ven Kataraban | ............ | 700/40 |
| 5,371,834 A | 12/1994 | Tawel | ............ | 706/25 |
| 5,631,734 A | 5/1997 | Stern | ............ | 356/317 |
| 5,733,729 A | 3/1998 | Lipshutz | ............ | 435/6 |
| 5,784,162 A | 7/1998 | Cabib et al. | ............ | 356/456 |
| 5,812,272 A | * 9/1998 | King et al. | ............ | 356/445 |
| 5,822,466 A | 10/1998 | Morfill | ............ | 382/260 |
| 5,858,659 A | 1/1999 | Sapolsky et al. | ............ | 435/6 |
| 5,925,525 A | 7/1999 | Fodor | ............ | 435/6 |
| 5,968,740 A | 10/1999 | Fodor | ............ | 435/6 |
| 5,974,164 A | 10/1999 | Chee | ............ | 382/129 |
| 6,025,601 A | 2/2000 | Trulson | ............ | 250/461.2 |

(Continued)

FOREIGN PATENT DOCUMENTS

EP 1162572 A2 * 12/2001

OTHER PUBLICATIONS

Kuklin, et al., High throughput screening of gene expression signature, 2000, pp. 41–46.*
Cheung et al., Analysis of gene microarray images, 1999, pp. 627–632.*
PCT/US03/14182 to VIOLOGY Corp.*

*Primary Examiner*—Andrew W. Johns
*Assistant Examiner*—Shervin Nakhjavan
(74) *Attorney, Agent, or Firm*—Fish & Richardson P.C.

(57) ABSTRACT

The current invention discloses a novel spectral transformation technique for characterizing digitized intensity output patterns from microarrays. This method yields improved sensitivity with reduced false positives and false negatives. Current microarray methods are overly sensitive to the detection of a visible distinction between pixels associated with probes and pixels associated with background. In one embodiment, a technique is disclosed that comprises the steps of: extracting pixels associated with an object of interest and transforming such pixels from an intensity representation to a spectral representation. In some embodiments, the extraction is based on a tessellated logarithmic spiral extraction that may yield a pixel core with a sampling of both foreground and background pixels. This core may then be computationally rescaled by 10×–10,000× to enhance spatial resolution. Once the extracted pixels are represented in the spectral regime, convolution with resolution-enhancement kernels may be used to accentuate morphological features capturing platform specific phenomenology.

300 Claims, 54 Drawing Sheets

U.S. PATENT DOCUMENTS

| | | | | |
|---|---|---|---|---|
| 6,066,454 | A | 5/2000 | Lipshutz | 435/6 |
| 6,090,555 | A | 7/2000 | Fiekowsky | 435/6 |
| 6,136,541 | A | 10/2000 | Gulati | 435/6 |
| 6,142,681 | A | 11/2000 | Gulati | 702/19 |
| 6,165,734 | A * | 12/2000 | Garini et al. | 435/7.21 |
| 6,171,793 | B1 | 1/2001 | Phillips | 435/6 |
| 6,185,561 | B1 | 2/2001 | Balaban | 707/6 |
| 6,218,122 | B1 | 4/2001 | Friend | 435/6 |
| 6,223,127 | B1 | 4/2001 | Berno | 702/19 |
| 6,225,625 | B1 | 5/2001 | Pirrung | 250/302 |
| 6,228,593 | B1 | 5/2001 | Lipshutz | 435/6 |
| 6,229,911 | B1 | 5/2001 | Balaban | 382/128 |
| 6,242,180 | B1 | 6/2001 | Chee | 435/6 |
| 6,245,511 | B1 | 6/2001 | Gulati | 435/6 |
| 6,294,327 | B1 | 9/2001 | Walton | 435/6 |
| 6,308,170 | B1 | 10/2001 | Balaban | 707/3 |
| 6,342,355 | B1 | 1/2002 | Hacia | 435/6 |
| 6,344,316 | B1 | 2/2002 | Lockhart | 435/6 |
| 6,349,144 | B1 * | 2/2002 | Shams | 382/129 |
| 6,361,937 | B1 | 3/2002 | Stryer | 435/6 |
| 6,368,799 | B1 | 4/2002 | Chee | 435/6 |
| 6,370,478 | B1 | 4/2002 | Stoughton | 702/19 |
| 6,391,550 | B1 | 5/2002 | Lockhart et al. | 435/6 |
| 6,420,108 | B1 | 7/2002 | Mack | 435/6 |
| 6,453,241 | B1 | 9/2002 | Bassett | 702/19 |
| 6,468,744 | B1 | 10/2002 | Cronin | 435/6 |
| 6,485,913 | B1 * | 11/2002 | Becker et al. | 435/6 |
| 6,490,533 | B1 | 12/2002 | Weiner | 702/27 |
| 6,495,363 | B1 * | 12/2002 | Bogdanov | 435/287.2 |
| 6,498,863 | B1 * | 12/2002 | Gaidoukevitch et al. | 382/173 |
| 6,542,638 | B1 | 4/2003 | Campbell | 382/201 |
| 6,567,750 | B1 | 5/2003 | Nadon | 702/19 |
| 6,571,005 | B1 | 5/2003 | Li | 382/133 |
| 6,671,625 | B1 | 12/2003 | Gulati | 702/20 |
| 6,704,662 | B1 | 3/2004 | Gulati | 702/27 |
| 6,716,629 | B1 * | 4/2004 | Hess et al. | 435/420 |
| 2001/0033364 | A1 * | 10/2001 | Cabib et al. | 351/221 |
| 2002/0052882 | A1 | 5/2002 | Taylor | 707/104.1 |
| 2003/0044775 | A1 | 3/2003 | Gulati | 435/5 |
| 2003/0071843 | A1 | 4/2003 | Hoff | 435/5 |
| 2003/0112446 | A1 * | 6/2003 | Miller et al. | 356/504 |
| 2003/0219150 | A1 * | 11/2003 | Niles et al. | 382/128 |
| 2003/0235840 | A1 * | 12/2003 | Ward et al. | 435/6 |

* cited by examiner

1ng

SYSTEM AND METHOD FOR CHARACTERIZING MICROARRAY OUTPUT DATA

CLAIM OF PRIORITY

This invention claims priority from U.S. patent application Ser. No. 60/377,520, filed on May 3, 2002, which is hereby fully incorporated by reference.

SOFTWARE APPENDIX

A Software Appendix comprising four sheets is included herewith.

FIELD OF THE INVENTION

The invention relates to a system and method for characterizing output data from an arrayed platform, and more specifically, arrays for characterizing biological material, including genetic material.

BACKGROUND OF THE INVENTION

Arrayed platforms or arrays typically consist of an arrangement of two or more detectors in one or more dimensions. The detectors of such arrays output data that may be monitored to observe various conditions of interest. In particular, arrayed platforms with a plethora of detectors may be useful in simultaneously monitoring a wide range of conditions by providing many different detectors and/or by utilizing numerous identical detectors for redundant measurements. However, errors still occur when characterizing data that is output from an array.

Most arrayed platforms suffer from background noise and other interferences that distort or obscure the output data resulting in erroneous measurements. This is particularly the case where the intensity of the output from each detector is close to or below the background noise threshold.

One type of arrayed platform are microarrays which typically comprise of a plurality of detectors (target probes) to which biological matter, such as a sample of genetic material (e.g., oligonucleotides, peptides, cDNA, proteins, etc.) may hybridize in some fashion to complimentary material. The genetic material used with typical microarray experiments is often labeled using fluorescence, chemiluminescence, bioluminescence, photoluminescence, or some other spectral emitter. The presence of a spectral emitter at a detector probe (also referred to herein as an object of interest) suggests that hybridization has taken place, and therefore, that the sample includes genetic material corresponding to the detector. However, the background noise on microarrays, label signals associated with non-specific hybridization, poor resolution, and protocol variations, among other things, often distort the spectral output and result in false negatives where an expressed hybridization signal is not detected, and false positives, where noise, platform defects, or other signals (such as non-specific hybridization) are incorrectly determined to be signals associated with hybridization.

The spectral intensity generated by a microarray is detected using a scanner (e.g., laser scanner, CCD array) or other detection device such as those sold by Axon, Affymetrix, Agilent and others. The detected spatial intensity is saved as a pixellated or raster output pattern data file (referred to herein as an "output pattern"). Typically, these images are saved in standard formats such as .jpg, .tif, gif, etc. and may be analyzed using a variety of analysis programs. The output patterns comprise an array of contiguous pixels that include both the pixellated intensity provided by the detectors on the array as well as other portions of the array within the total scan area of the scanner.

The total intensity emitted by an object of interest (i.e., a detector) within an output pattern is commonly referred to as a "feature" or "spot". One or more features or spots may correspond to a specific gene that is being detected or analyzed. This identification may occur by parameterizing the spots, using spot size, spacing, layout, packaging, distortion boundaries, etc.

Traditional microarray characterization techniques analyze pixels associated with objects of interest, as well as pixels associated with background noise on the microarray. However, such techniques are imprecise and require the analysis of large amounts of data that is not germane to the microarray experiment. In addition, while some techniques attempt to extract relevant information from an output pattern, conventional systems often exclude pixels associated with an object of interest and/or include pixels associated with background results, resulting in inaccurate and imprecise characterization (especially with regard to microarrays used for weakly expressed gene detection and gene quantitation). The imprecision in results becomes worse for situations where (i) images are very noisy due to instrument, coating, linker chemistry, or platform substrate noise; (ii) images are noisy due to biological or assay noise; (iii) the sample applied to the microarray is inadequately labeled due to poor labeling efficacy; (iv) photo bleaching effects; (v) imprecise and variations in spotting; (vi) labels or dyes bleed through in images where multiple dye scanning are used in connection with energy transfer dyes; and (vii) the output patterns often do not have sufficient spatial resolution to characterize each object of interest on an array.

Conventional techniques for spot extraction utilized in hybridization images (microarrays, biochips and protein arrays), include rectilinear scanning on regular grids and the use of extraction masks. Rectilinear scanning refers to a pixellated spot represented in Cartesian (x, y) coordinate space. With this arrangement, the spot, covering m×n pixels, is either traversed in x-direction, row-by-row for the m-rows, or it is traversed in the y-direction for all the n-columns. With extraction masks, a square, circular, elliptical or polygonal mask is pre-designed as an extraction template. A "set-intersection" with the pre-configured mask is then performed to extract all the pixels that are contained within the mask boundary. The mask application may be preceded by an additional spot registration step that entails sliding the mask around the centroid of the segmented object to a position that minimizes the number of segmented pixels that are outside the mask boundary. Alternatively, the segmented object may be translated in a rectilinear or diagonal direction to increase precision. While rectilinear scanning and extraction masks provided an advantage over some extraction techniques, there remains a need for an improved system with increased precision that is adaptable to extraction non-standard spot sizes. In addition, there remains a need for an array analysis system that can provide enhanced spatial resolution over output patterns generated by a scanning/detection device.

Notwithstanding the above, arrayed platforms remain a useful and promising technique for simultaneously detecting multiple conditions of interest. Greater adoption of arrays would occur if there was a system and method for characterizing output patterns that was robust and repeatable. Accordingly, it will be appreciated that there remains a need for an improved system for extracting information relating to an object of interest within an array output pattern and for enhancing the resolution of an array output pattern. It is to these and other ends that aspects of the present invention are primarily directed.

SUMMARY OF THE INVENTION

The invention is disclosed, in a technique for characterizing information from a pixellated output pattern of a microarray having one or more objects of interest. The technique commences with the step of extracting pixels within the output pattern representative of each object of interest. Next, the intensity representation of the extracted pixels are transformed to a spectral representation.

In some embodiments, the step of transforming the intensity representations of the extracted pixels is dependent upon the expected signal level for each object of interest and may be adjusted accordingly.

In some embodiments, the pixels are extracted using a radial spiral transversal. With some arrangement the radial spiral traversal originates at a centroid of each object of interest and progresses outwardly and in other arrangements the radial spiral traversal originates at a pre-determined distance from the centroid. The radial spiral traversal may terminate at a segment boundary pixel for each object of interest, or the radial spiral traversal may terminate at a pre-determined distance beyond a segment boundary for each object of interest. In yet another embodiment, the radial spiral traversal terminates at a pre-determined distance before a segment boundary for each object of interest.

In yet other embodiments, the radial spiral traversal converges inwardly toward a centroid of each object of interest. With such arrangements, the radial spiral traversal may terminate at the centroid for each object of interest, or it may terminate at a pre-determined distance inside a segment boundary for each object of interest. The radial spiral traversal may originate on a segment boundary pixel, at a pre-determined distance outside a segment boundary, or within a segment boundary for each object of interest.

The use of logarithmic spirals are also disclosed to extract pixels. In some embodiments, the logarithmic spiral uses a tessellated extraction mask, which may comprise a texture mask. A variety of texture masks may be used in connection with the current invention including Bernoulli spiral masks, logistique masks, Hirschorn masks, Voderberg masks, bent-wedge tile masks, kinked tile masks, rhomboidal tile masks, triangular tile masks, equiangular spiral masks, symmetric tessellation masks, asymmetric tessellation masks, and spiral mirabilis masks.

The current invention also may adapt to differing types of objects of interest. For example, the radial spiral traversal for pixel extraction may be configured to extract pixels associated with objects of interest having varying geometric sizes, pixels associated with objects of interest distributed geometrically irregularly on the microarray, and pixels associated with objects of interests having varying geometric sizes and distributed geometrically irregularly on the microarray.

Other types of pixel extraction techniques that may be used in connection with the current invention include degenerate logarithmic spiral masks, rectilinear masks, row-major extraction, column-major extraction.

In some variation of the preferred embodiment, the characterization technique further comprises the step of computationally re-scaling the extracted pixels to increase spatial resolution of the extracted pixels prior to the step of transformation the intensity representation. The computationally re-sampling the extracted pixels comprises may result from the convolving of the extracted pixels with a kernel, which may be a discretized kernel with coefficients chosen from the groups comprising linear functions, non-linear functions, and canonical kernel functions. In some embodiments, the computational re-sampling of the extracted pixels results from the product of a scalar dot product with an affine transformation, or a linear function. The spatial resolution may also be increased by convolution of the extracted pixels with a canonical coefficient kernel that yields two or more modified pixels for each extracted pixel, or through the utilization of a cascade of computational convolutions with discretized canonical kernel functions, with each successive convolution conducted on the results of preceding convolution. Such convolution cascades may be serial cascades, parallel cascades, or a a combination of a serial cascade and a parallel cascade.

The output pattern that is characterized may comprise an array of spatially contiguous pixels. In such arrangements, it is determined which pixels are representative of each object of interest, or indicative of morphological representation of an object of interest. Information-theory or information measure may be used to determine which pixels should be associated with an object of interest.

The invention discloses the use of the step transforming the domain of the extracted pixels from spatial intensity to spatial frequency. This transformation may occur through a Fourier transform, such as a Fast Fourier Transform, or a Discrete Fourier Transform. Once the domain has been transformed to a spatial representation, a spectral vector representing the transformed object may be partitioned into overlapping, or non-overlapping subvectors prior to convolving with discretized coefficients of a function. The power spectral density may be estimated from the spectral representation of the extracted pixels. In some embodiments, a spectrally transformed vector is decomposed into subvectors associated with an object of interest, where each subvector is convolved with a resolution enhancement kernel and synthetically resampled. The post-convolution computationally re-sampled transformed spectral subvectors may then be combined to yield a single spectral vector.

In some embodiments of the current invention, the technique further includes the step of decomposing the extracted pixels into a set of discrete extracted objects, where each discrete extracted object is transformed into a spectral representation. In other embodiments, the technique removes pixels that do not pertain to an object of interest prior to the pixel extraction step.

The invention also discloses the use of a logarithmic spiral to estimate a local background of an object of interest A wide variety of arrays may be utilized with respect to the current invention, including arrays such as hybridized spotted cDNA microarrays, synthesized oligonucleotide arrays, spotted oligonucleotide arrays, peptide nucleotide assays, single nucleotide polymorphism (SNP) arrays, carbohydrate arrays, glycoprotein arrays, protein arrays, proteomic arrays, tissue arrays, antibody arrays, antigen arrays, bioassays, sequencing microarrays, sequencing by hybridization (SBH) microarrays, siRNA duplexes, RNAi arrays glass-based arrays, nylon membrane arrays, thin film arrays, polymer-substrate arrays, capillary electrophoresis arrays, genospectral arrays, electronic arrays, bead arrays, quantum dot arrays, and gylcan arrays. Such arrays may include emitters including: fluorescence, chemiluminescence, bioluminescence, and photoluminescence.

In order to facilitate the approximate location of objects of interest, the technique includes the step of registering and/or segmenting the pixels within the output pattern to approximate the location of the objects of interest.

In some analysis techniques, it may also be desirable to adjust the contrast of the output pattern. The invention describes a variety of contrast filters including Gabor filters, low-pass band-pass filters, high-pass band-pass filters, edge detection operators, Laplacian filters, gradient-focusing filters.

Another specific method is disclosed which may be utilized to characterize information from a pixellated microarray output pattern. This method includes the steps of segmenting the output pattern to approximate the locations of the objects of interest within the output pattern; filtering the segmented output pattern to enhance the contrast; extracting a core of pixels associated with each object of interest; resampling the extracted core pixels to enhance spatial resolution; transforming the representation of the resampled extracted core pixels from the intensity domain to the spectral domain; convolving the transformed spectral domain resampled extracted core pixels with a kernel; and estimating the power spectral density from the convolved transformed spectral domain resampled extracted core pixels.

The current invention is also embodied in a computer code product that characterizes information from a pixellated output pattern of microarray that represents one or more objects of interest, The computer code product includes computer code that extracts spatial data elements within the output pattern representative of each object of interest; and computer code that transforms the intensity representation of the extracted pixels to a spectral representation The current invention is also disclosed in a computer system for characterizing information from a pixellated output pattern of a microarray representing one or more objects of interest. The computer system includes a processor and a memory coupled to said processor. The memory is configured to encode one or more programs that may perform the steps of: extracting spatial data elements within the output pattern representative of each object of interest; and transforming the intensity representation of the extracted pixels to a spectral representation.

In yet another embodiment, a system for analyzing an output pattern of an array of detectors, each detector representing one or more objects of interest is disclosed. This system includes means for extracting spatial data elements within the output pattern representative of each object of interest; and means for transforming the intensity representation of the extracted pixels to a spectral representation.

The current invention is also disclosed as an article of manufacture, made by a method for characterizing information from a pixellated output pattern of an array of detectors, each detector representing one or more objects of interest. The method includes the steps of extracting spatial data elements within the output pattern representative of each object of interest; and transforming the intensity representation of the extracted pixels to a spectral representation.

As can be appreciated, a wide range of embodiments are consistent with the general principles of the invention.

DESCRIPTION OF THE ACCOMPANYING FIGURES

FIG. 6($b$) illustrates the ordering of the pixels as traversed in FIG. 6($a$);

FIG. 8($b$) illustrates a sample logarithmic spiral with a pre-defined parametric constant a having a value of 0.17;

FIG. 8($c$) illustrates a sample logarithmic spiral with a pre-defined parametric constant $\alpha$ having a value of 0.25;

FIG. 9($b$) illustrates a first embodiment of a tessellated spiral extraction mask overlaying an object of interest with outward radial progression commencing from the centroid of the object of interest;

FIG. 9($c$) illustrates a first embodiment of a tessellated spiral extraction mask overlaying an object of interest with inward radial progression commencing from a boundary point of the object of interest;

FIG. 10($b$) illustrates a second embodiment of a tessellated spiral extraction mask overlaying an object of interest with inward radial progression commencing from a boundary point of the object of interest;

FIG. 11($b$) illustrates a third embodiment of a tessellated spiral extraction mask overlaying an object of interest with inward radial progression commencing from a boundary point of the object of interest;

FIG. 12($b$) illustrates a fourth embodiment of a tessellated spiral extraction mask overlaying an object of interest with inward radial progression commencing from a boundary point of the object of interest;

FIG. 13($b$) illustrates a fifth embodiment of a tessellated spiral extraction mask overlaying an object of interest with inward radial progression commencing from a boundary point of the object of interest;

DETAILED DESCRIPTION OF THE EXEMPLARY EMBODIMENTS

With reference to the figures, exemplary embodiments of the invention will now be described. The current invention is embodied in a technique for characterizing output data from an arrayed platform. While the invention is primarily described in connection with genomic microarrays, biochips and protein arrays, it will be appreciated by one of the ordinary skill in the art that the invention may be used in connection with a wide variety of arrayed platforms of detectors, including detectors for characterizing biological materials and other applications. It will also be appreciated that while the current invention is primarily described as a method, it may also be embodied in system comprising a computer processor and a memory coupled to the processor, where the memory is encoded with one or more programs that may perform the methods disclosed herein. One of ordinary skill in the art will also appreciate that the invention may also be embodied in an enhanced output pattern (which is an article of manufacture) that is the result of the techniques described herein.

Figure 1:
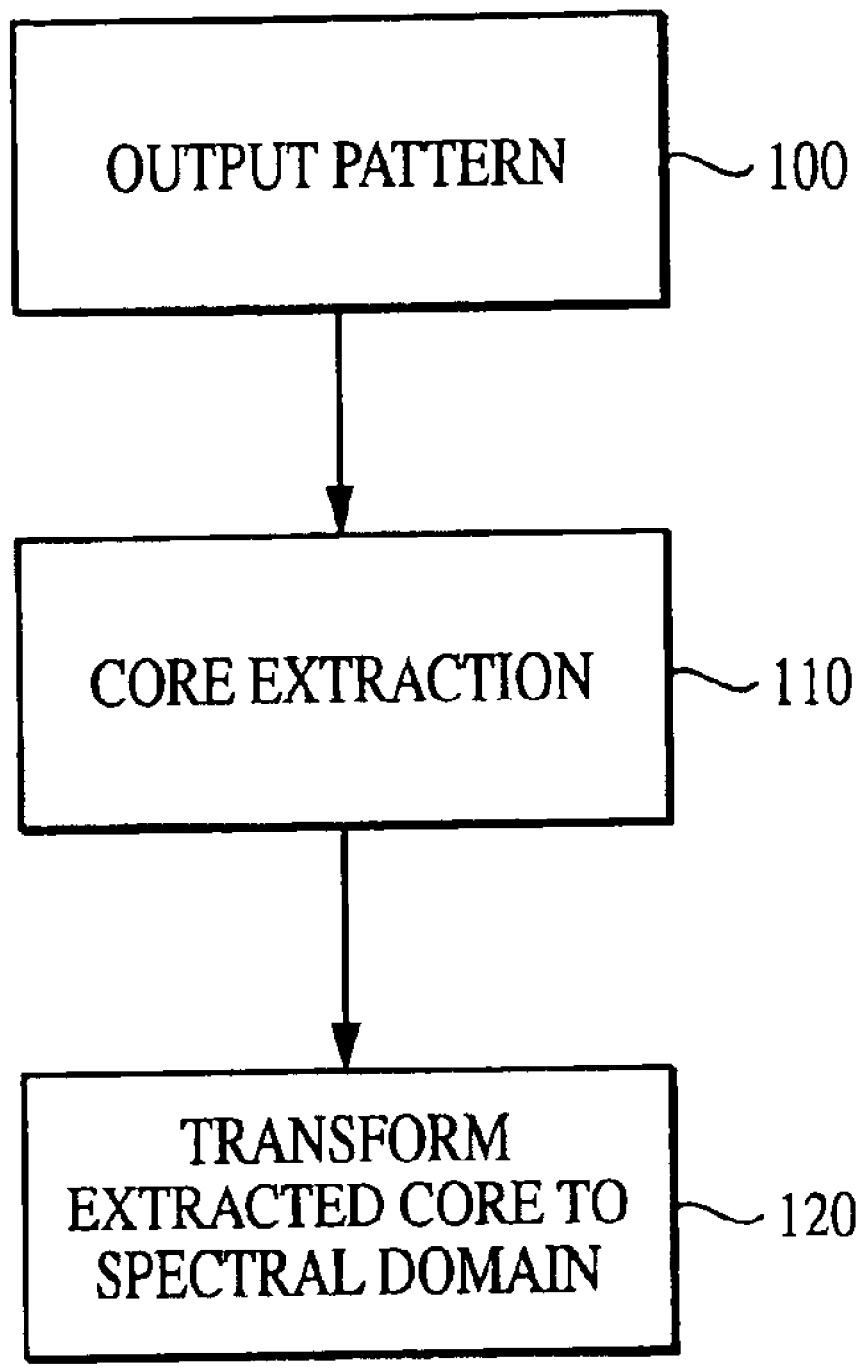
FIG. 1 illustrates a flowchart providing an overview of the preferred embodiment of the invention.
Figure 2:
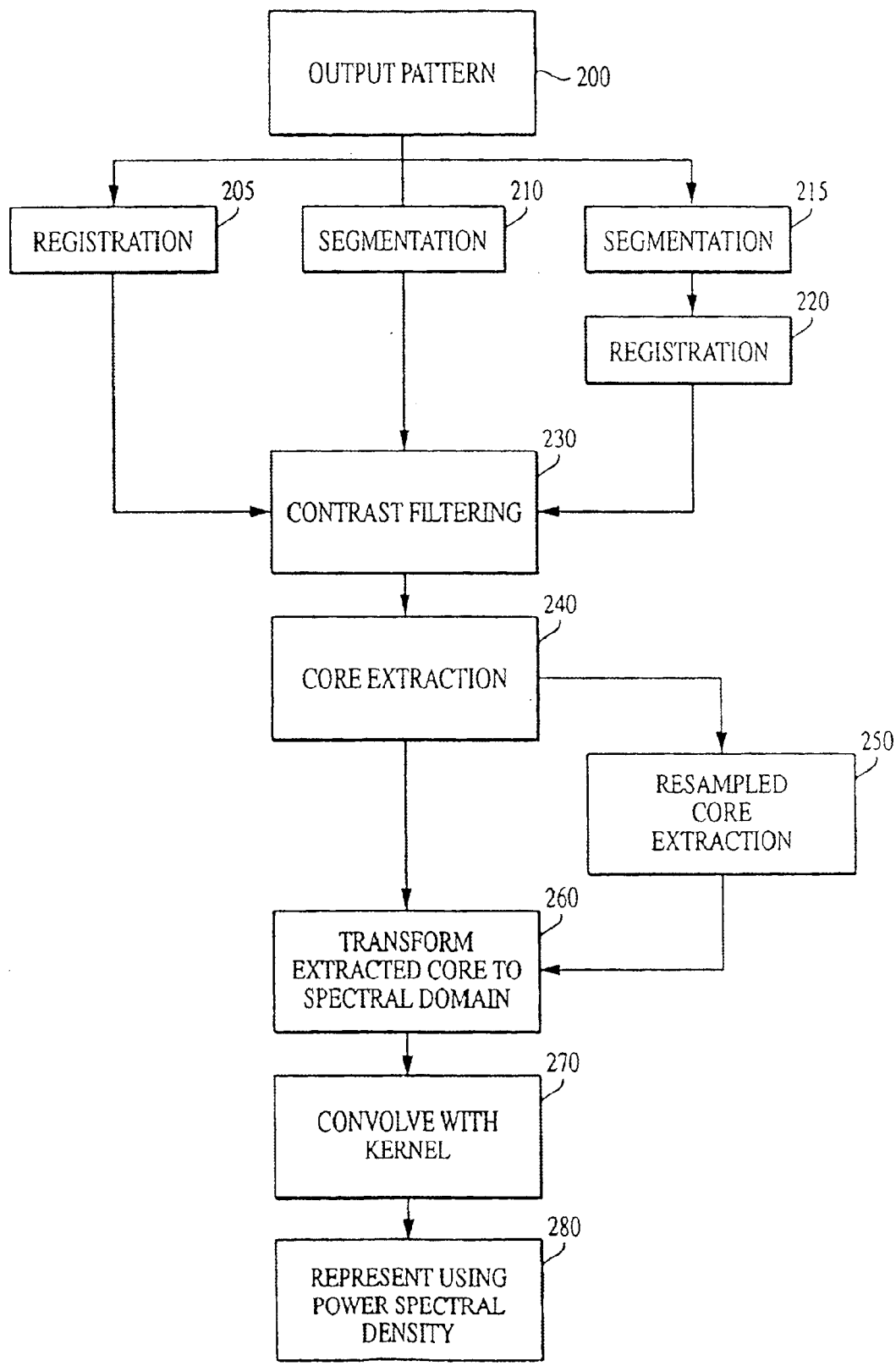
FIG. 2 illustrates a more detailed version of the flowchart of FIG. 1 including variations found in additional embodiments.

With reference to FIG. 1, the preferred embodiment of the current invention describes a method and system for extracting a core of pixels relating to an object of interest 110 within an array output pattern 100, and then transforming the domain of the extracted core from the spatial domain to the spectral domain 200. In other embodiments as shown collectively in FIG. 2, the output pattern 200 is first registered 205, or segmented 210, or segmented 215 then registered 220, to provide an approximate location for each object of interest within the output pattern. A contrast enhancement filter 230 (which may be in addition to the previous segmentation filtering 210, 215) is then applied to the output pattern to enhance the contrast of the output pattern prior to extraction of the core 240. In some embodiments, the extracted core is computationally (or synthetically) re-sampled to increase spatial resolution 250. The domain of the extracted core is then transformed into the spectral domain 260 followed by a convolution with a kernel 270, such as a resolution enhancement kernel. The last step consists of estimating the power spectral density (PSD) from the spectral components of the transformed core 280. The resulting data may then be used to characterize events on the microarray.

In an exemplary embodiment, the arrayed platform comprises an array of detectors or probes labeled with spectral emitting dyes (each referred to herein as an object of interest) useful in characterizing labeled genetic material within a sample (a microarray). The probes, sample or both may be pre-labeled. Preferably, the genetic material being analyzed is labeled using traditional techniques and dyes that may be detecting using fluorescence, chemiluminiscence, bioluminescence, and photoluminescence imaging modalities. Sample arrays include hybridized spotted cDNA microarrays, synthesized oligonucleotide arrays, spotted oligonucleotide arrays, peptide nucleotide assays, single nucleotide polymorphism (SNP) arrays, carbohydrate arrays, glycoprotein arrays, protein arrays, proteomic arrays, tissue arrays, antibody arrays, antigen arrays, bioassays, sequencing microarrays, sequencing by hybridization (SBH) microarrays, siRNA duplexes, RNAi arrays, glass-based arrays, nylon membrane arrays, thin film arrays, polymer-substrate arrays, capillary electrophoresis arrays, genospectral arrays, electronic arrays, bead arrays, quantum dot arrays, glycan arrays as well as any other arrays that are indicative of binding phenomenology and provide an output in a spectral regime.

The current invention relates to the analysis and characterization of a microarray output pattern. An output pattern is first examined to identify those pixels within the output pattern that correspond to objects of interest (this process is also known as registration). For example, see FIG. 3 which includes a portion of an output pattern 300 which includes two objects of interest 310, 320. In one embodiment, a grid is provided that identifies the location of the objects of interest within the output pattern. This grid is typically generated by the instrumentation software utilized to generate the objects of interest (e.g., for microarrays, it may be the spotter). Most grids will provide information to facilitate the identification of some or all of the total number of objects of interest that are present, including the sizes of each object of interest, their spatial distribution, and the center points associated with the objects of interest. Graph isomorphism algorithmic techniques may also be utilized to register objects of interest to accommodate distortions in the output pattern.

In other embodiments, registration may occur using only information contained within the output pattern. For example, the output pattern may include explicit grid alignment controls/indicators present on the arrayed platform to facilitate the definition of corners, boundaries and guide points within the output pattern. By geo-referencing the grid alignment controls of the image, all objects of interest may be segmented. In other variations, registration takes place without any apriori information regarding the array by associating pixels within the output pattern to expected spot sizes, locations, geometric constraints, and other features of the array.

In output patterns where multiple dyes or multiple imaging modalities are employed, registration acts to correlate the differing modalities. For example cDNA arrays use Cy3 and Cy5 (two color dyes) as indicators of hybridization in differentially labeled samples, and as a result, two different output patterns are generated for two spectral dimensions. With such multiple dye arrangements, registration also correlates two different spots within the two images that represent the same physical detector probe location. Preferably, spatial overlaying, graph isomorphisms, sub-graph isomorphisms and polarization filters are used to overlay and register different images, and correct for local distortion effects.

In some embodiments, the current invention relates to the analysis of microarrays to detect the presence of genes and their respective expression levels. Such microarrays may include objects of interest such as genomic detectors including oligonucleotide, cDNA, RNA, and the output pattern represents the imaged intensity at the objects of interest on the microarray. Within the output pattern, the current invention also identifies pixels that are representative of each object of interest including their morphological representations and morphological invariants as related to the cumulative effects from source such as the substrate, probe type, microarray printing instrumentation, bioassay, and scanning instrumentation.

As described above, information from the instrument that created the array may be used as a guide such as spotter/genomic printer/arrayer layout files, spotter pin-head information, lithography masks, and mask generation files. In embodiments where output pattern is a representation of a capillary electrophoresis-based imaging array, the positioning, dimensions, and inter spacing of the capillary tubes, provide guiding information for downstream detection of post-hybridization intensity originating from a specific genomic element. Accordingly, prior to analysis, the pixels generally corresponding to objects of interest within the output pattern are identified through expected predetermined properties.

If it is determined that the output pattern does not have sufficient contrast to identify pixels associated with an object of interest, various types of filters may be applied to the image. Such contrast enhancement may be useful in defining boundaries for the various objects of interest, to distinguish them from the background, that may then be used for generating segmentation contours. One embodiment convolves the output pattern with a Gabor filter, and more specifically with a set of two-dimensional Gabor filters.

The output pattern $I_{spot}(x,y)$, $x, y \in \Omega$ where $\Omega$ denotes a set of image points is convolved with a two-dimensional Gabor function $$g(x,y), x,y \in \Omega.$$

to obtain a Gabor feature image r(x,y) as follows:

$$r(x, y) = \int\int_\Omega I(\xi, \eta)g(x-\xi, y-\eta)d\xi d\eta$$

One family of Gabor functions that may be used with the current invention is described below. The standard deviation σ of the Gaussian factor determines the effective size of the surrounding of a pixel in which weighted summation takes place. The eccentricity of the Gaussian and herewith the eccentricity of the convolution kernel g is determined by the parameter γ, called the spatial aspect ratio. Preferably, a value of γ=0.5 is used, although one of ordinary skill in the art will recognize that the spatial aspect ratio may be modified pursuant to the output pattern being characterized.

Pixels within the resulting convolved output pattern associated with an object of interest may then be extracted with a standard kernel convolution process. The extraction of such pixels progresses until a pre-defined condition is met indicating that the extraction is complete for a particular object of interest (i.e. a boundary condition). A standard edge detect kernel such as sobel operator may be used to generate edges that demarcate the pixels associated with an object of interest from pixels associated with the background. With some output patterns, it may be desirable to enhance the contrast therein. Alternative filtering techniques to Gabor filters that may be used with the current invention include: (i) low-pass/high-pass, band-pass filters; (ii) predetermined operators such as edge detection operators; (iii) Laplacian filters; and (iv) gradient-focusing filters.

Once the objects of interest are located, the current invention then optimally associates pixels with each object of interest to define an "extraction core" or "core". For gene hybridization analysis the extraction core denotes the pixels that will be associated with an object of interest (i.e., a specific gene for genomic microarrays). All downstream decisions for detecting the absence or presence of an object of interest (e.g., gene), will be made based on this information contained within the core pixels as a starting basis. The parameters for defining a core may be:

(i) supplied by the user as expectation parameters. For example, in some embodiments the user provides his expectation of spot geometry, inter-spot spacing, spot diameter explicitly in terms of images pixels; or (ii) provided by the instrumentation used to generate the array (i.e., spotter files, lithographic mask information). The resolution of the output pattern may also be utilized in combination with the spatial data to determine the optimal number of pixels to define the core. The scanning resolution (expressed in pixels terms—1 micron×1 micron pixel) is mapped to the feature size setting used by the spotter (expressed as 50 micron features or 18 micron features). This information is used to determine the number of pixels in the output image that capture an object of interest. Depending on the scanning resolution this may range from a single pixel to 10s or 1000s of pixels;

(iii) estimated using information-theoretic computations, if information regarding the core locations are unavailable. For example, an entropy map is generated based on intensity gradients computed over the entire image. A standard (3×3, 5×5, or N×N) sliding circular, polygonal or rectangular detection kernel is then applied to the entire image within the output pattern. The dimension N is so chosen to cover the largest expected spot or feature. The kernel application partitions or segments the image. An information entropy map is then computed based on the distance between extracted core geometry and the segmented feature. The arrayed image is then further segmented into regions with similar entropy distribution.

In some embodiments, a spatial filter is re-applied to the segmented objects (based on similar entropy measure), based on the array generation instrumentation configuration (i.e., spotter/pin head geometry) to then extract pixels associated with objects of interest. This arrangement requires an entropy map to be pre-computed for the objects of interest and then parameterized to accommodate variation due to artifacts and noise. This extraction process requires copying the core pixels (i.e., the pixels associated with a likely object of interest) to a data structure that can index to all the objects (denoting hybridized genes) associated with the array.

Once the core for each object of interest is identified, the segmented pixels associated with each such core are extracted. Once extracted, the segmented core pixels are used to populate a machine readable, data structure indexing the entire collection of objects of interest. Thereafter, the populated data structure is used to generate the modified output pattern comprising of the extracted pixels. The core extraction process is equivalent to deconstruction of the entire output array with m×n (denoted by $I_1$) pixels into a data structure that captures only the spatial intensities of the relevant objects and has pixels totaling $$I_2 = j \sum_k \sum_i I_{ik}$$

where j denotes the total number of objects of interest (e.g., pre-synthesized probes) on the array, and $l_{ik}$ denotes the number of extracted pixels associate with the k-th feature of each object of interest. Also, k denotes the number of features encoding for object of interest i.

Also, $I_2 > I_1$.

Figure 4:
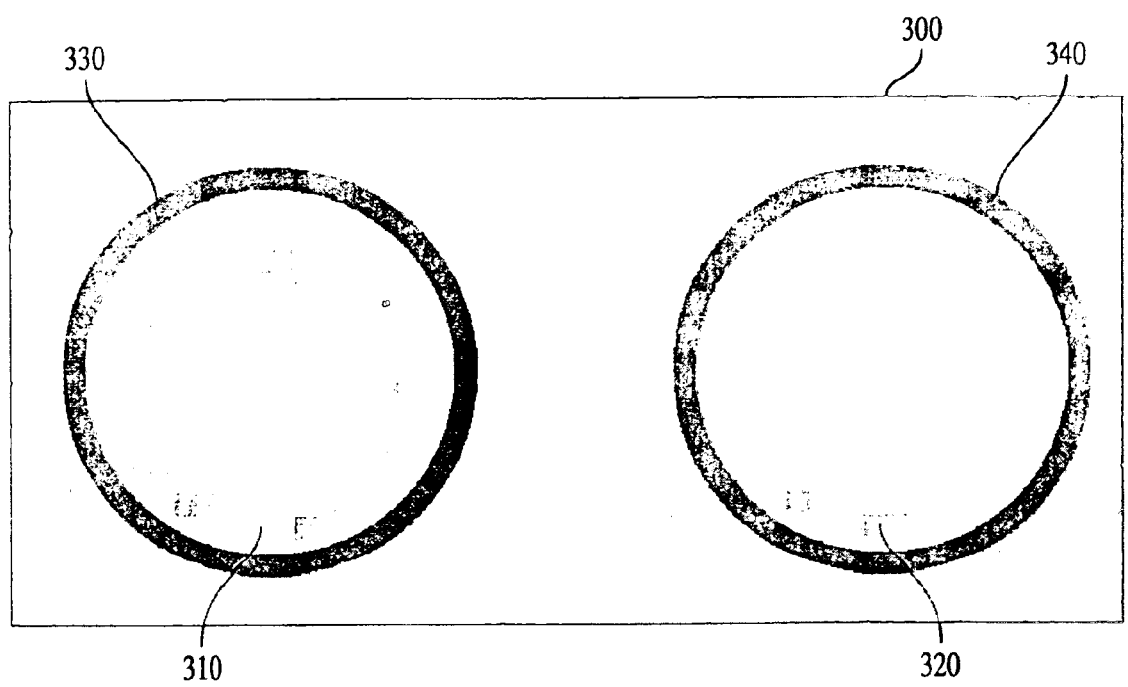
FIG. 4 illustrates a circular segmentation of the output pattern of FIG. 3.

The current invention utilizes customized sophisticated traversal to compensate for sources of errors described above, all of which tend to reduce the signal ultimately present in the output pattern and/or increase the background noise or blur the boundary between the object of interest and background. As used herein, the term traversal refers to the process of how the segmented pixels associated with an object of interest are scanned by the algorithm for purposes of extracting and analyzing the core pixels (i.e., a hybridized spot). It is assumed that in images with low signal-to-noise (SNR) and signal-to-clutter ratio (SCR), or poor contrast, or saturation effects, segmentation will be imprecise and will necessarily include background pixels or exclude core pixels. As it is often difficult to predetermine the SNR or SCR without analyzing the entire image, or to identify those spots that have been degraded, the current invention assumes all images and all spots to be susceptible to suboptimal segmentation (as show in FIG. 4 where objects of interest 310 and 320 are respectively segmented by circles 330 and 340 which include both pixels associated with the objects of interest and with the background and do not encircle all pixels associated with the objects of interest). Further, core extraction and an advanced adaptive core extraction are used to compensate for limited segmentation.

Figure 5:
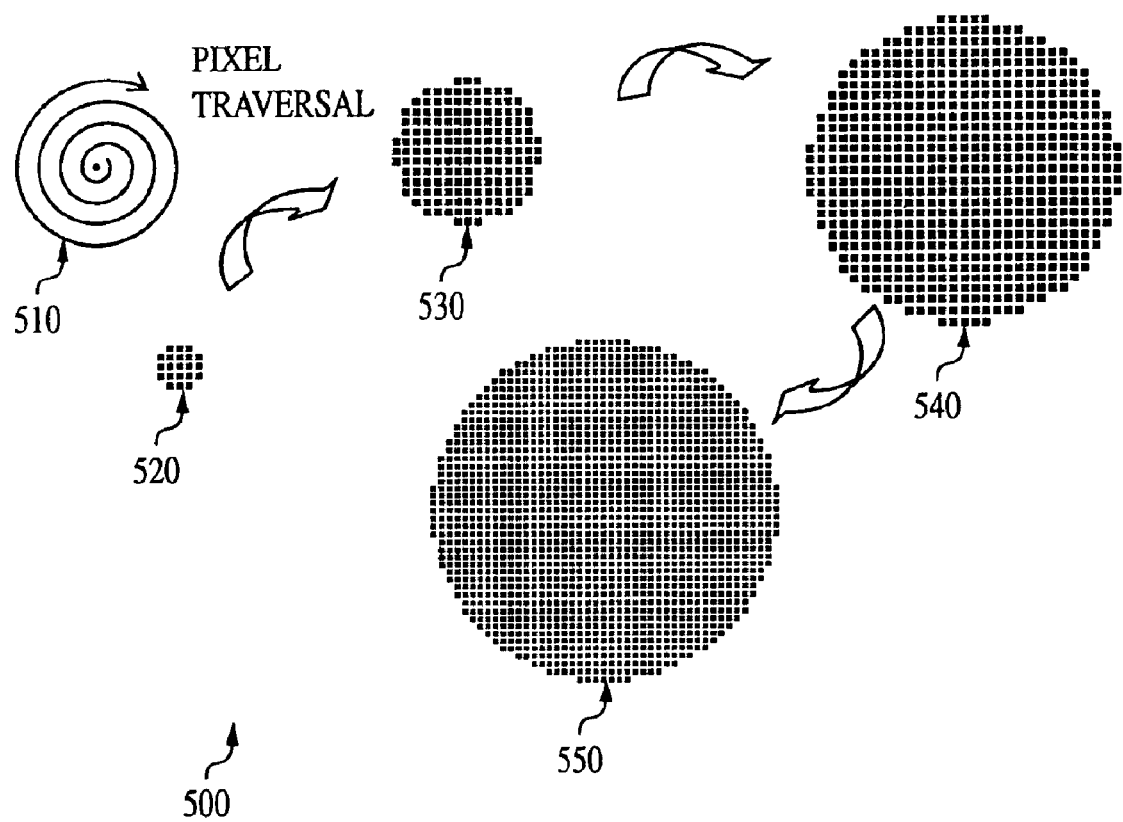
FIG. 5 illustrates an exemplary extraction technique based on spiral unwrapping.

In contrast to conventional microarray output analysis techniques, the pixels (which may be segmented) associated with the object of interest within the output pattern are spirally extracted to create a modified output pattern that primarily consists of those extracted pixels relating to objects of interest. For example, see FIG. 5 which illustrates 500 a spiral extraction 510 which as it traverses outwardly, increases the number of extracted pixels 520, 530, 540, 550. Unlike circular and rectilinear extraction techniques that limit the core size, spiral extraction is inherently adaptive and can accommodate varying core sizes (as shown in FIGS. 5 and 6).

Figure 6A:
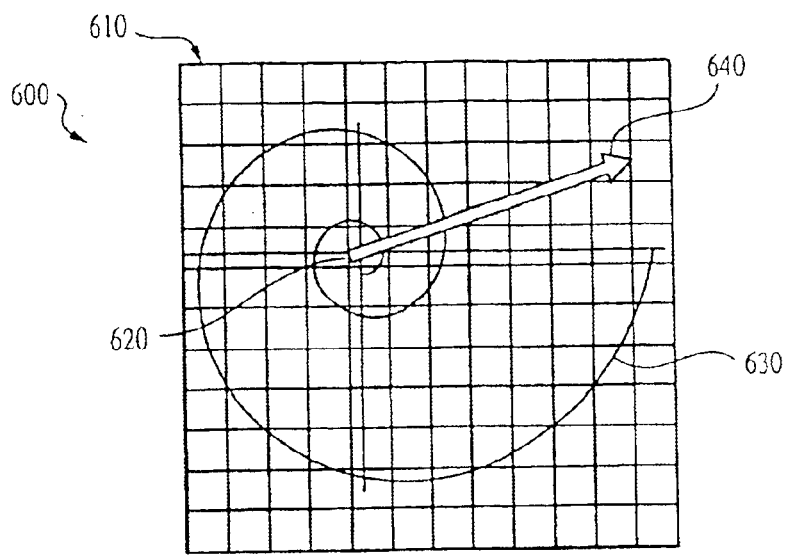
FIG. 6($a$) illustrates an exemplary logarithmic spiral trajectory overlaid on a pixellated grid.
Figure 6B:
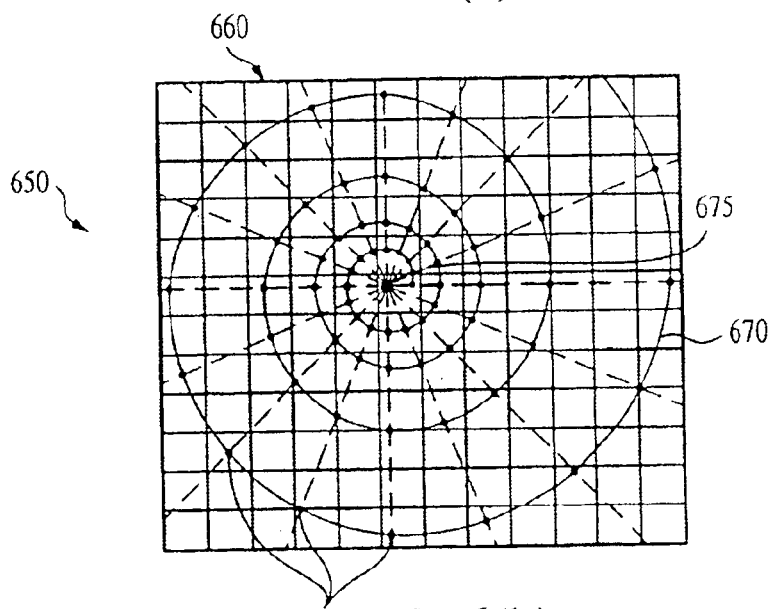

In some embodiments, as illustrated in FIGS. 6(a), the spiral extraction preferably uses spiral traversal 620 originating at center of the object of interest 620 (when known) which traverses outwardly 640 (as overlaid on grid 610), and in other embodiments an inward radial spiral traversal is utilized. As a further example, as illustrated in FIG. 6(b), a spiral transversal 670 overlaid on a grid 660 traverses outwardly from a centroid 675 to generate a sequence of extracted pixels 680. Spiral extractions are further illustrated in FIG. 7 which demonstrates a progression of an outward spiral transversal 700, to computationally generate a series of segments 720 between extracted pixels. In addition, other variations of spiral extraction may be utilized such as outward and inward polygonal spiral transversals. The preferred method of extraction is logarithmic spiral extraction.

Figure 8A:
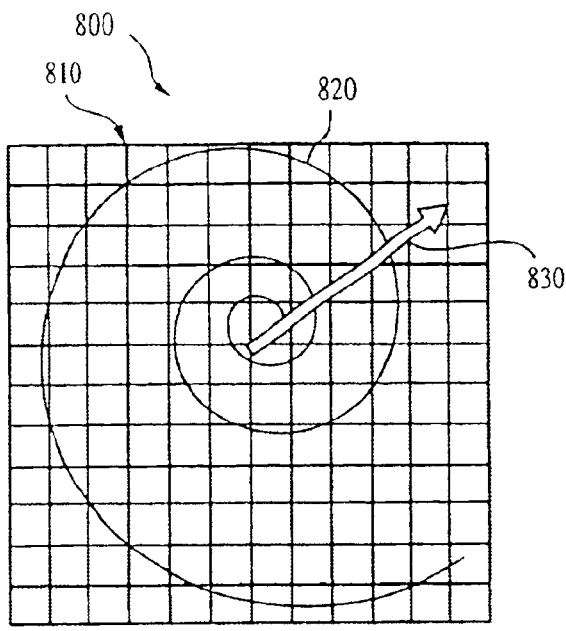
FIG. 8($a$) illustrates a sample logarithmic spiral with a pre-defined parametric constant a having a value of 0.15.
Figure 8B:
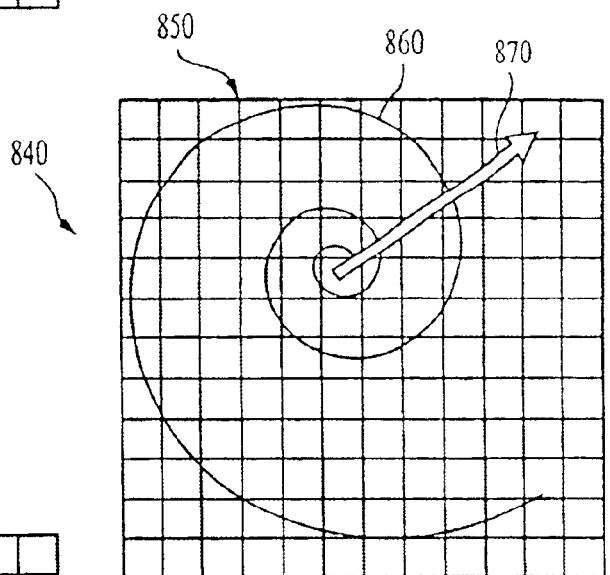
Figure 8C:
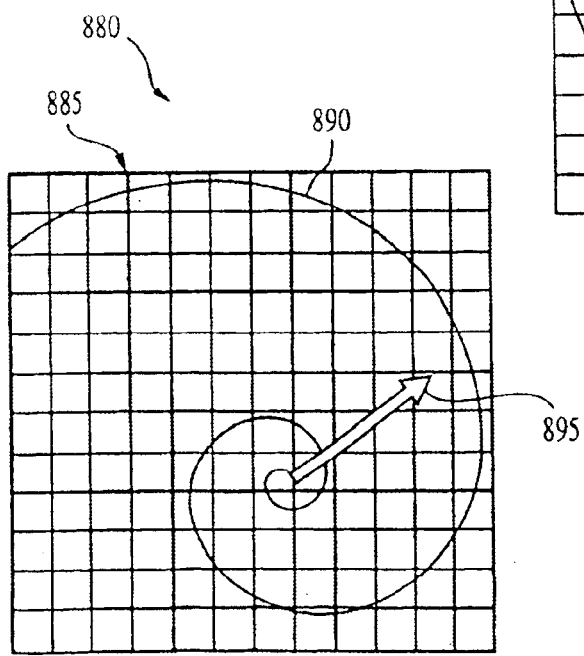

With reference to FIGS. 8(a)–8(c), examples of outward logarithmic spiral traversals for extraction of images with varying parametric constants are illustrated. Each logarithmic spiral example 800, 840, 880 includes a spiral 820, 860, 890 overlaid on a grid 810, 840, 885 that traverses outwardly 830, 870, 895. The equation for the logarithmic spiral curve in polar coordinates is given by $$R = ae^{b\theta}$$

where r is the distance from the centroid, θ is the angle from the x-axis, and a and b are arbitrary parametric constants spiral curvature and modulation (as show in FIGS. 8(a)–8(c)). The logarithmic spiral family is also known as the growth spiral, equiangular spiral, and spiral mirabilis, and can be expressed parametrically as $$x = r\cos\theta = a\cos\theta e^{b\theta}$$

$$y = r\sin\theta = a\sin\theta e^{b\theta}.$$

Figure 7:
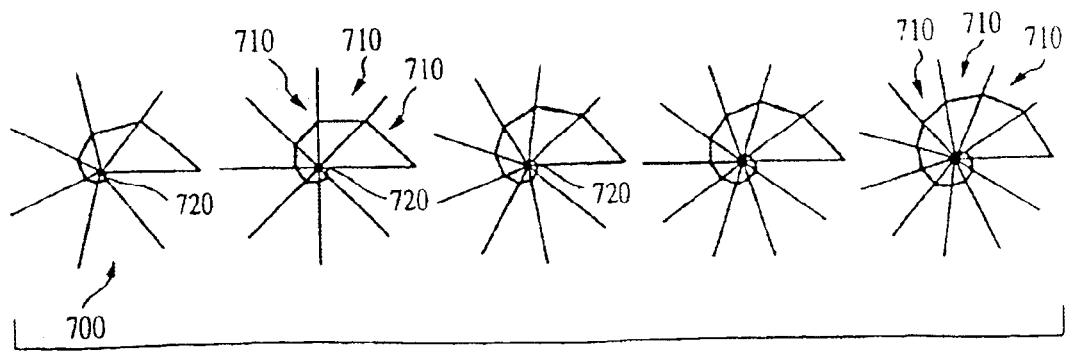
FIG. 7 illustrates the segmented progression of a spiral trajectory.

With reference to FIGS. 6(a) and 7 a graphical representation of an exemplary logarithmic spiral is illustrated. The logarithmic spiral may be constructed from equally spaced rays (straight lines intersecting two predetermined Cartesian coordinates) by starting at a point along one ray, and drawing the next ray perpendicular to a neighboring ray. As the number of rays approach infinity, the sequence of segments approaches a logarithmic spiral. Therefore a logarithmic spiral (also referred to as an equiangular spiral) is defined as a spiral that forms a constant angle between a line from the origin to any point on the curve and the angle of the tangent line at that point and its tangent is equal to the original angle. The family of equiangular spirals (including the Bernoulli spiral and logistique) are defined as spirals with a monotonic curve that cuts all radii vectors at a constant angle. The inverse of these spirals is also the same spiral. So the inverse spiral of an equiangular spiral defines an extraction trajectory to be implemented for adaptively extracting the segmented object of interest.

One equation for the rate of change of radius, for a spiral described by $$\boxed{r = e^{a\phi}}$$

is given by $$\frac{dr}{d\theta} = abe^{b\theta} = br,$$

and the angle between the tangent and radial line at the point $(r, \theta)$ is computed using:

$$\psi = \tan^{-1}\left(\frac{r}{\frac{dr}{d\theta}}\right) = \tan^{-1}\left(\frac{1}{b}\right) = \cot^{-1} b.$$

So, as b→0, $\psi \to \pi/2$ the spiral approaches a circle. A circle is also represented as a spiral for which the radius grows exponentially with the angle in the case of logarithmic spirals. The distances where a radius from the origin meets the curve are in geometric progression.

The arc length (s), curvature (κ), and tangential angle (φ) of the logarithmic spiral are computed using $$s = \frac{a\sqrt{1+b^2}}{b}(e^{b\theta} - 1)$$

$$\kappa = \frac{e^{-b\theta}}{a\sqrt{1+b^2}}$$

$$\phi = \theta.$$

With reference to FIG. 6(b), the morphing of a spiral trajectory to a circular trajectory as defined above is illustrated. At any extraction point the spiral and circular extractions are interchangeable. This is particularly important for implementing the extraction trajectory using a computer. Also, this behavior in the limit condition provides a mechanism for accurately extracting perfect or near-perfect circular cores using spiral extraction algorithms.

The parametric equations of a curve (f(t), g(t)) with radial point $(x_0, y_0)$ and parameterized by a variable t are given by $$x = x_0 - \frac{g'(f'^2 + g'^2)}{f'g'' - f''g'}$$

$$y = y_0 + \frac{f'(f'^2 + g'^2)}{f'g'' - f''g'}.$$

Derivatives are then taken with respect to the parameter t. The software code stub in C++ language for implementing the procedure for extracting a logarithmic spiral is provided in the Software Appendix.

The current invention accommodates the extraction of objects of interest that are distributed geometrically irregular on the array. The output image deconstruction step, implemented via core extraction obviates the requirement for image geometry or distribution patterns. For example, when the boundaries of the objects of interest to be extracted have been pre-segmented, and the segmented objects have been registered and enumerated explicitly, the extraction algorithm traverses the object of interest in a spiral trajectory (outward logarithmic spiral or inward). This results in a linear vector of extracted pixels. As illustrated in FIGS.

9–37, cores may be designed to be mapped to numerous types of spirals with differing geometric properties. Different spirals can encode for different spatial statistics of the core. Also, each core could be extracted using a different type of spiral. Each of such spirals has an equation driving its creation (as exemplified in computer modeling applications). The inverse spiral then defines the extraction trajectory for core extraction in this method. The generator equation of the inverse spiral provides the trajectory to be traversed. Traversing a spiral trajectory implies the process of computationally traversing the object pixels to copy them to an object centric data structure for subsequent computational analysis.

Figure 9A:
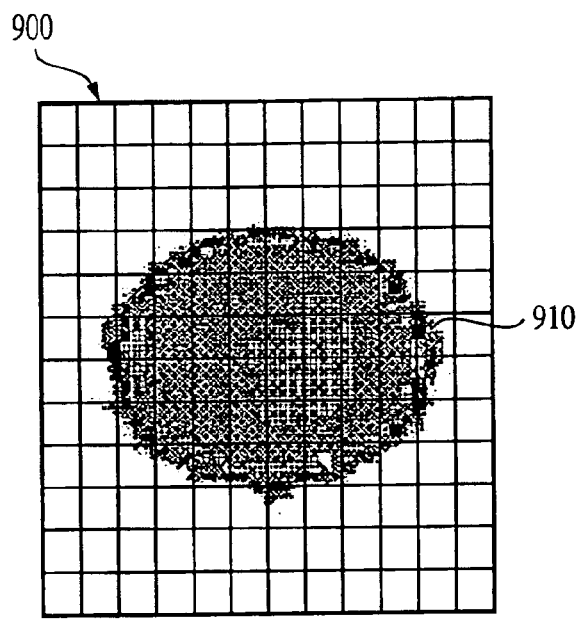
FIG. 9($a$) illustrates a single object of interest overlaid on a grid.
Figure 9B:
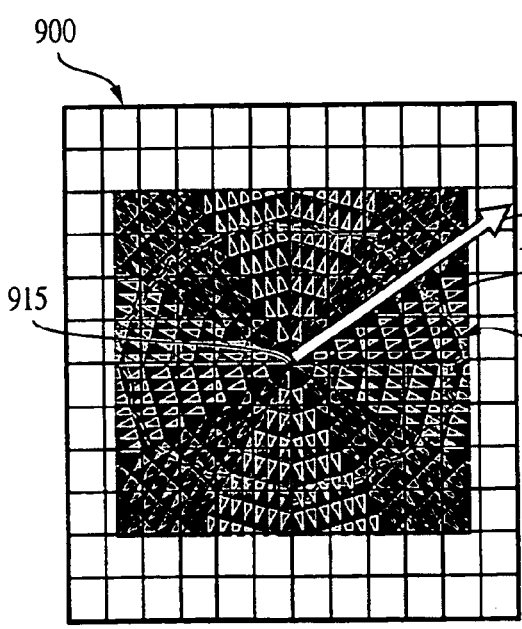
Figure 9C:
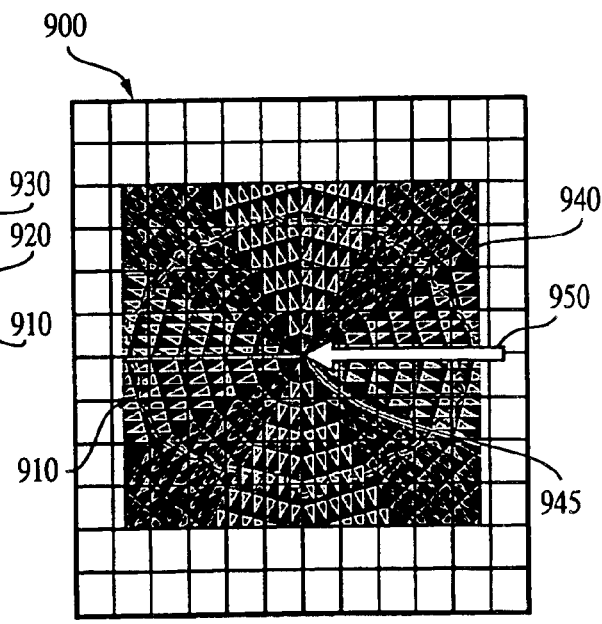

With reference to FIGS. 9(a)–9(c), an embodiment of a spiral extraction is illustrated with radial tilings. FIG. 9(a) illustrates an object of interest 910 overlaid on a pixellated grid 910 within a section of fluorescently labeled hybridized image obtained from a microarray output pattern generated using a confocal laser scanner operating at a specific wavelength and photomultiplier tube setting. The object of interest in the foreground of the output pattern can be extracted, as shown in FIG. 9(b) using an outward radial spiral extraction mask 920 with sectors of tessellated triangles converging at the centroid of the object of interest that traverse outwardly 930. FIG. 9(c) illustrates the extraction of the same segmented core extraction using the same radial spiral extraction mask 940 with inward progression that commences at any point on the segmented boundary or at the spiral mask template that traverses inwardly 950. All the sector extractions can be used for further processing or a plurality of sectors may be used.

Figure 10A:
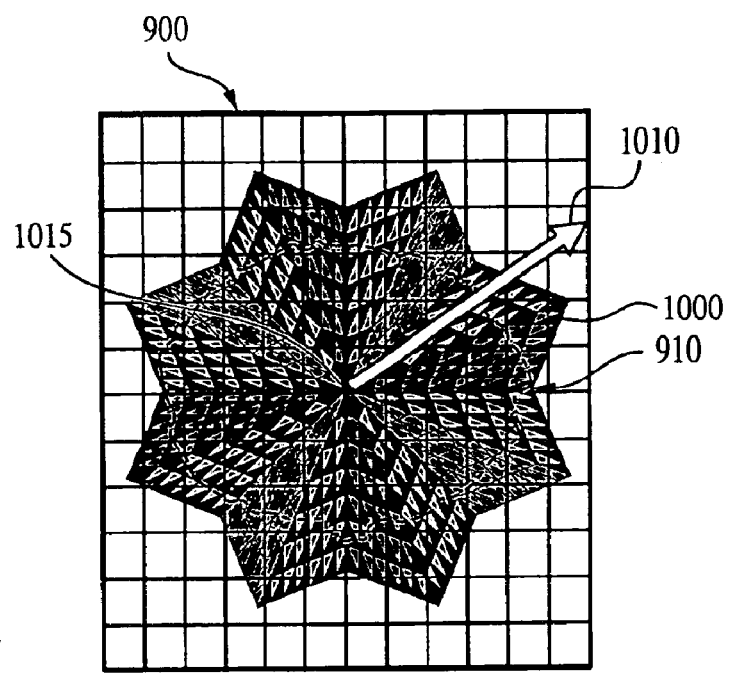
FIG. 10($a$) illustrates a second embodiment of a tessellated spiral extraction mask overlaying an object of interest with outward radial progression commencing from the centroid of the object of interest.
Figure 10B:
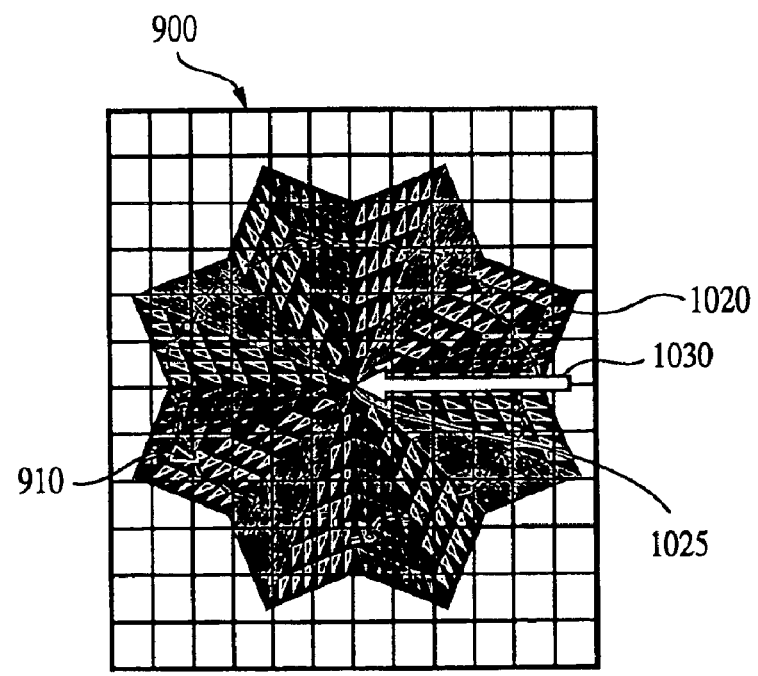

With reference to FIGS. 10(a)–10(b), a variation of spiral extraction is illustrated where the tessellated triangles in a spiral mask template are not isosceles, and a radial layout is formed with a pair of adjacent sectors that are interlaid as mirror-images of each other. An extraction mask 1000, overlaid on object of interest 910 (and interposed on grid 900), is derived from a radial spiral that traverses outwardly 1010 originating at the centroid 1015 of the object of interest (see FIG. 10(a)). In addition, an extraction mask 1020, overlaid on object of interest 910 (and interposed on grid 900), is derived from a radial spiral progression that originates at any point on the boundary of the object of interest (see FIG. 10(b)) and traverses inwardly 1030 towards the centroid 1025 of the object of interest.

Figure 11A:
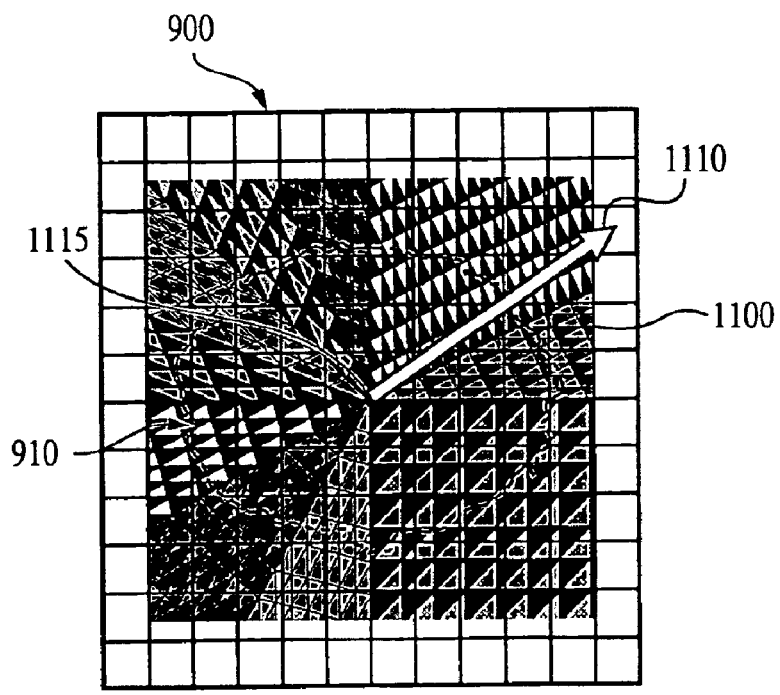
FIG. 11($a$) illustrates a third embodiment of a tessellated spiral extraction mask overlaying an object of interest with outward radial progression commencing from the centroid of the object of interest.
Figure 11B:
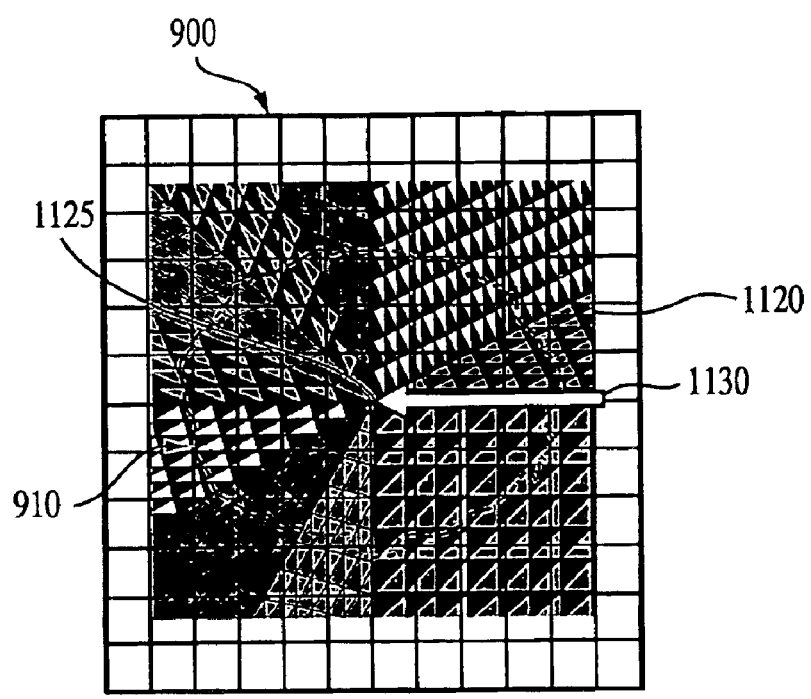

With reference to FIGS. 11(a)–11(b), another variation of spiral extraction is illustrated where the triangular wedges have varying angles, which do not always meet edge-to-edge, to generate a asymmetrical tessellation. An extraction mask 1100, overlaid on object of interest 910 (and interposed on grid 900), is derived from a radial spiral that traverses outwardly 1110 originating at the centroid 1115 of the object of interest (see FIG. 11(a)). In addition, an extraction mask 1120, overlaid on object of interest 910 (and interposed on grid 900), is derived from a radial spiral progression that originates at any point on the boundary of the object of interest (see FIG. 11(b)) and traverses inwardly 1130 towards the centroid 1125 of the object of interest.

Figure 12A:
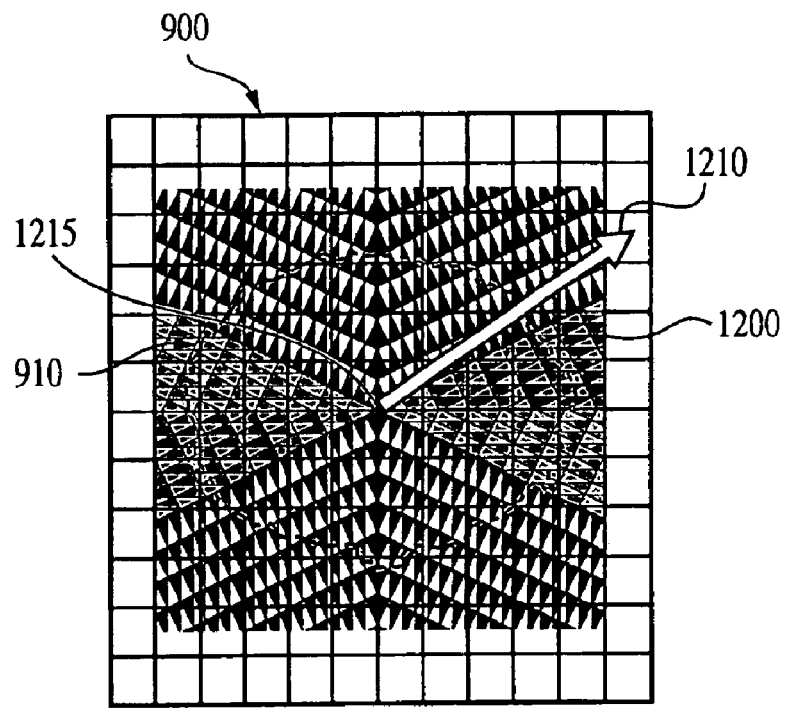
FIG. 12($a$) illustrates a fourth embodiment of a tessellated spiral extraction mask overlaying an object of interest with outward radial progression commencing from the centroid of the object of interest.
Figure 12B:
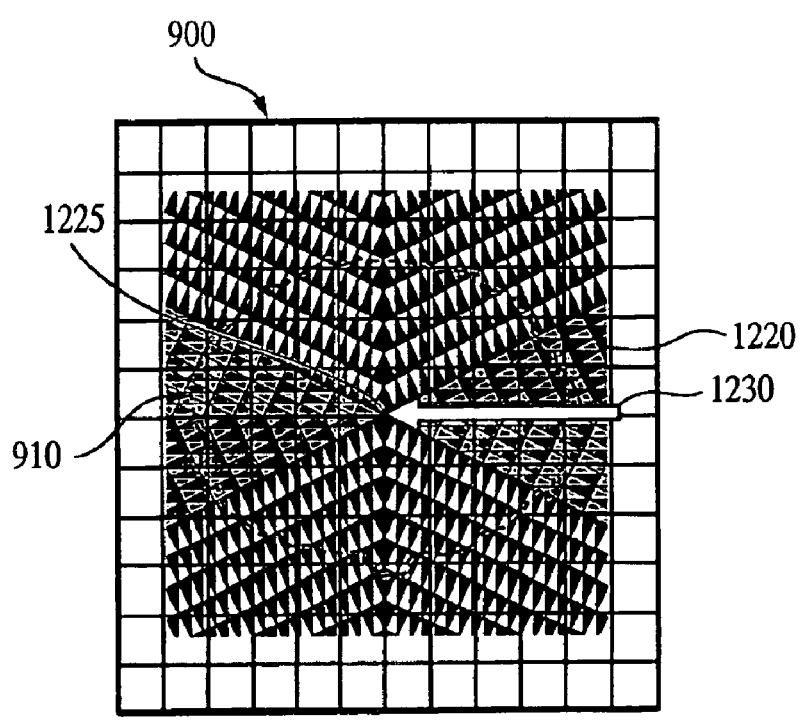

With reference to FIGS. 12(a)–12(b), another embodiment of spiral extraction is illustrated where the tiling of 1×2 right triangles is not edge-to-edge (as compared to FIG. 11(a)) or made of equal sectors (as shown in FIG. 10(a)). An extraction mask 1200, overlaid on object of interest 910 (and interposed on grid 900), is derived from a radial spiral that traverses outwardly 1210 originating at the centroid 1215 of the object of interest (see FIG. 12(a)). In addition, an extraction mask 1220, overlaid on object of interest 910 (and interposed on grid 900), is derived from a radial spiral progression that originates at any point on the boundary of the object of interest (see FIG. 12(b)) and traverses inwardly 1230 towards the centroid 1225 of the object of interest.

Figure 13A:
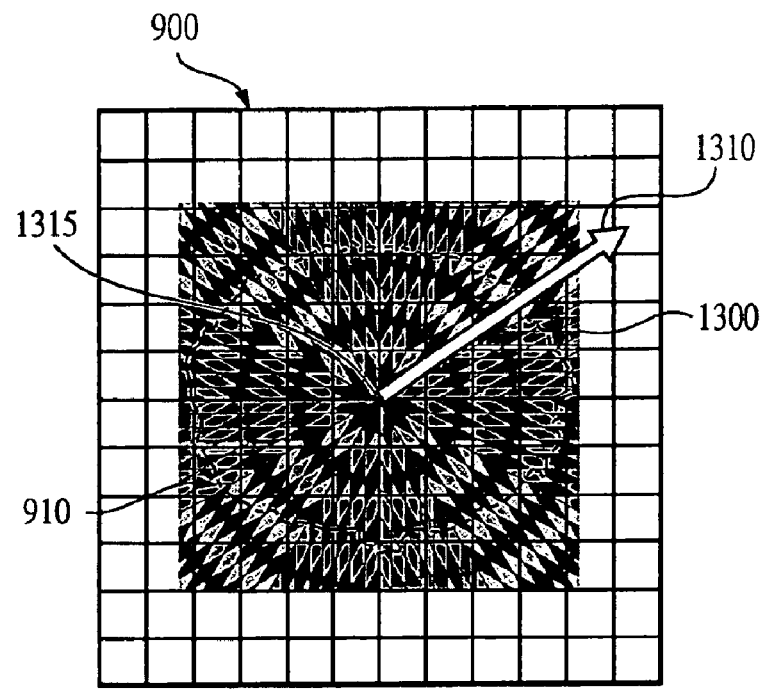
FIG. 13($a$) illustrates a fifth embodiment of a tessellated spiral extraction mask overlaying an object of interest with outward radial progression commencing from the centroid of the object of interest.
Figure 13B:
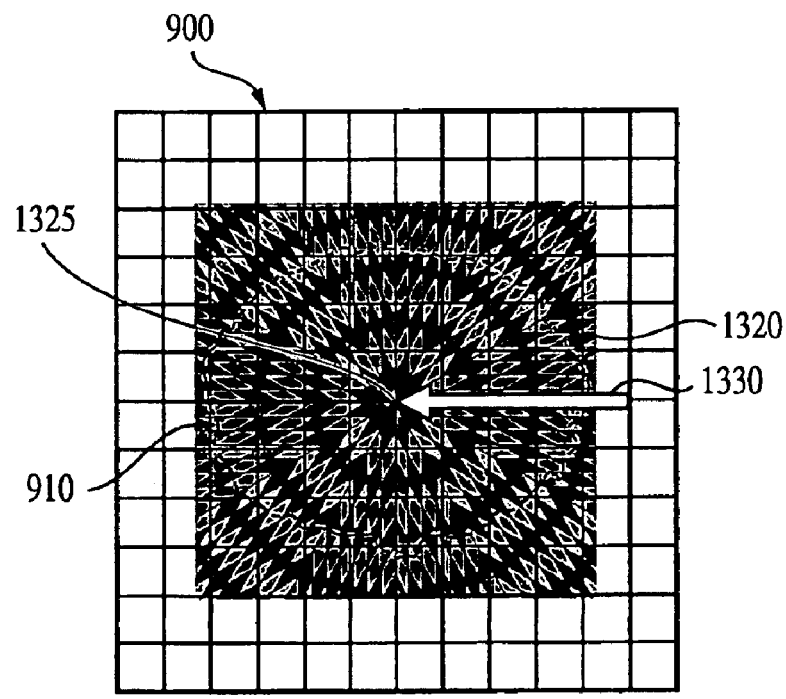

With reference to FIGS. 13(a)–13(b), in some embodiments, the spiral extraction uses joining or modifying triangles which form rhombuses with radial tessellations. An extraction mask 1300, overlaid on object of interest 910 (and interposed on grid 900), is derived from a radial spiral that traverses outwardly 1310 originating at the centroid 1315 of the object of interest (see FIG. 13(a)). In addition, an extraction mask 1320, overlaid on object of interest 910 (and interposed on grid 900), is derived from a radial spiral progression that originates at any point on the boundary of the object of interest (see FIG. 13(b)) and traverses inwardly 1330 towards the centroid 1325 of the object of interest.

Figure 14A:
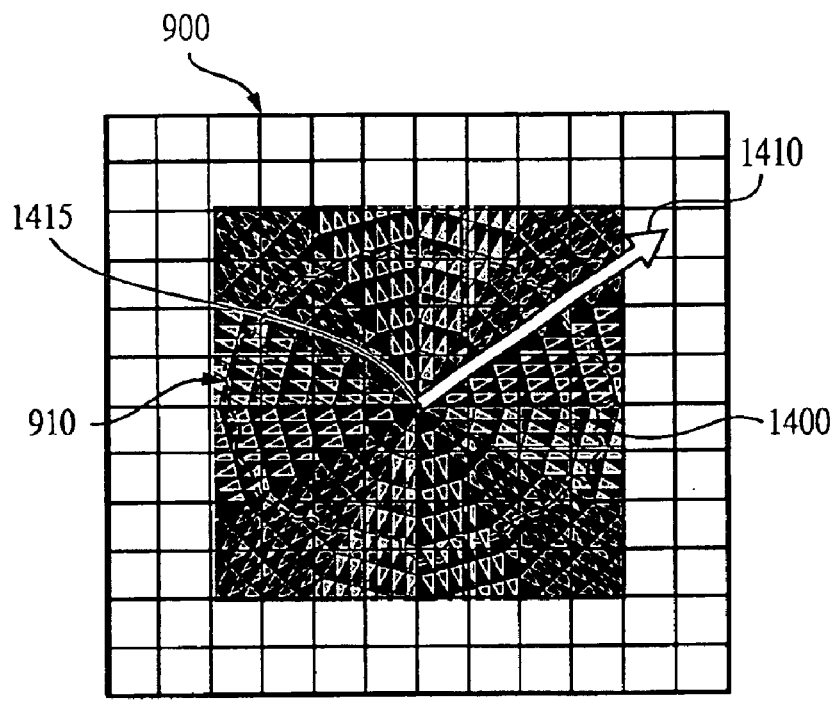
FIG. 14($a$) illustrates a sixth embodiment of a tessellated spiral extraction mask overlaying an object of interest with outward radial progression commencing from the centroid of the object of interest.
FIG. 14(b) illustrates a sixth embodiment of a tessellated spiral extraction mask overlaying an object of interest with inward radial progression commencing from a boundary point of the object of interest.
Figure 14B:
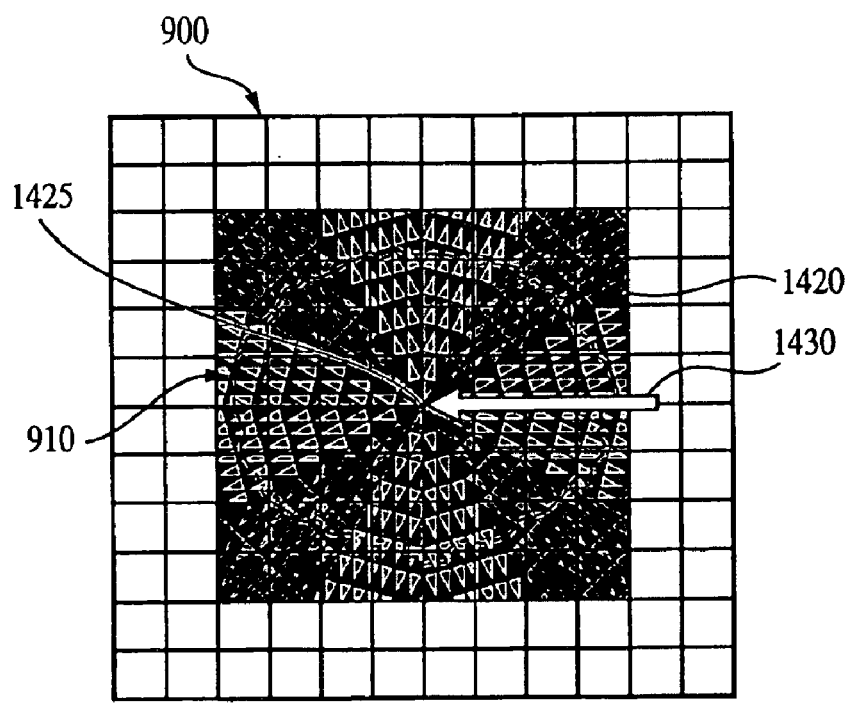

With reference to FIGS. 14(a)–14(b), a spiral extraction is illustrated that incorporates spiral tiling. This embodiment incorporates radial triangular tessellations with an even number of sectors that are bisected by straight lines. An extraction mask 1400, overlaid on object of interest 910 (and interposed on grid 900), is derived from a radial spiral that traverses outwardly 1410 originating at the centroid 1415 of the object of interest (see FIG. 14(a)). In addition, an extraction mask 1420, overlaid on object of interest 910 (and interposed on grid 900), is derived from a radial spiral progression that originates at any point on the boundary of the object of interest (see FIG. 14(b)) and traverses inwardly 1430 towards the centroid 1425 of the object of interest.

Figure 15A:
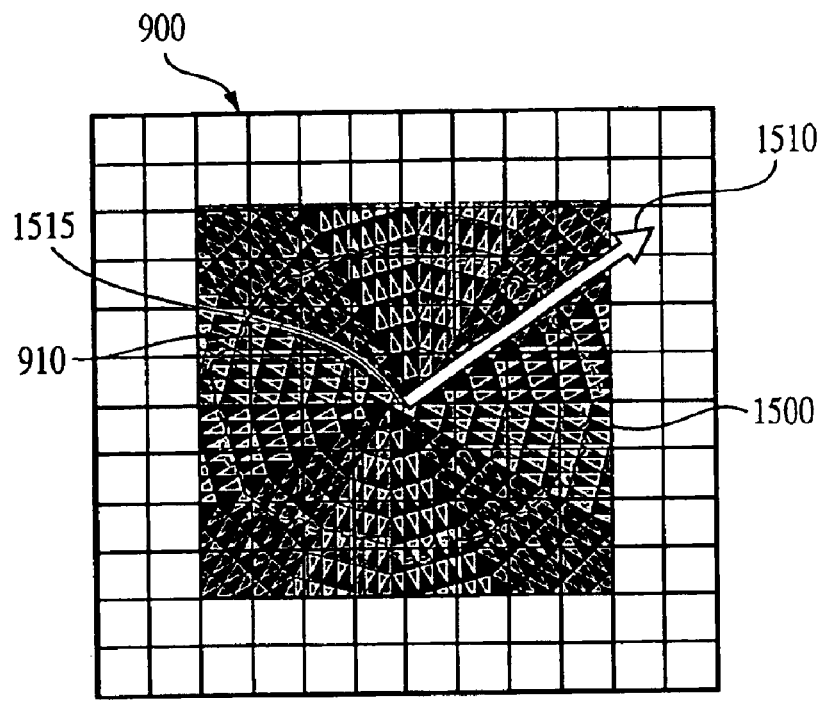
FIG. 15(a) illustrates a seventh embodiment of a tessellated spiral extraction mask overlaying an object of interest with outward radial progression commencing from the centroid of the object of interest.
Figure 15B:
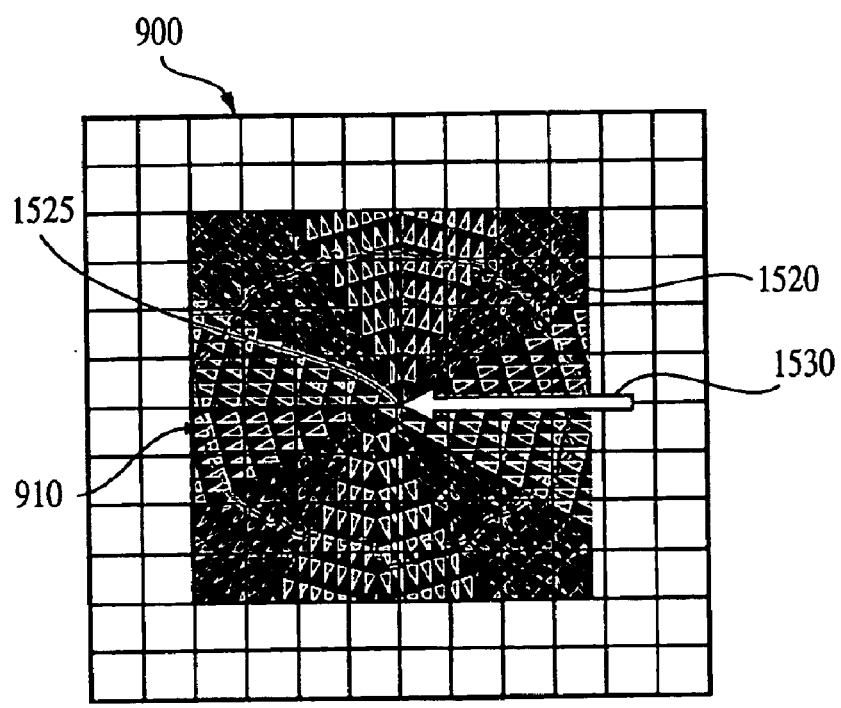
FIG. 15(b) illustrates a seventh embodiment of a tessellated spiral extraction mask overlaying an object of interest with inward radial progression commencing from a boundary point of the object of interest.

With reference to FIGS. 15(a)–15(b), another variation of a spiral extraction that utilizes spiral tiling is pictured. In this arrangement, two halves of a radial tiling on straight lines generate the spiral tiling. This form results in an offset among two sectors of identically-oriented triangles and creates a continuous "lane" of triangles. An extraction mask 1500, overlaid on object of interest 910 (and interposed on grid 900), is derived from a radial spiral that traverses outwardly 1510 originating at the centroid 1515 of the object of interest (see FIG. 15(a)). In addition, an extraction mask 1520, overlaid on object of interest 910 (and interposed on grid 900), is derived from a radial spiral progression that originates at any point on the boundary of the object of interest (see FIG. 15(b)) and traverses inwardly 1530 towards the centroid 1525 of the object of interest.

Figure 16A:
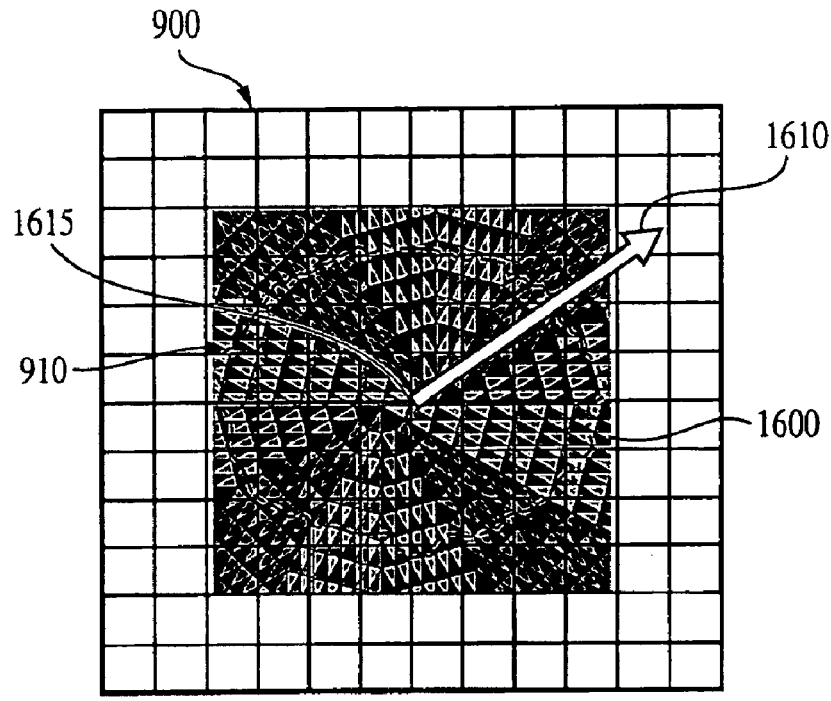
FIG. 16(a) illustrates an eighth embodiment of a tessellated spiral extraction mask overlaying an object of interest with outward radial progression commencing from the centroid of the object of interest.
Figure 16B:
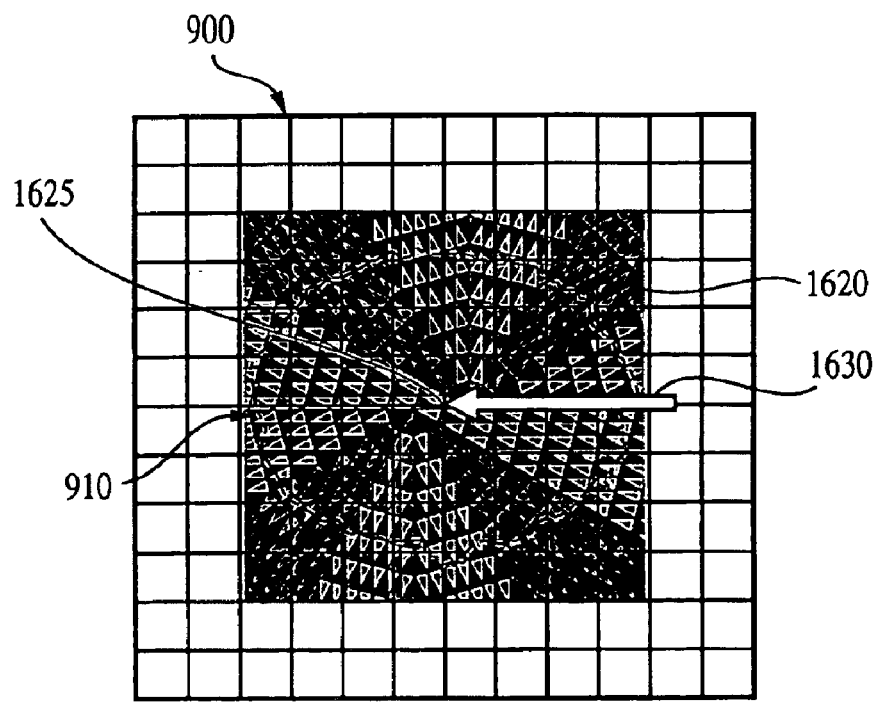
FIG. 16(b) illustrates an eighth embodiment of a tessellated spiral extraction mask overlaying an object of interest with inward radial progression commencing from a boundary point of the object of interest.

With reference to FIGS. 16(a)–16(b), an embodiment is disclosed where the tiling is offset by two cells where the lane of sectored triangles is wider than the previous embodiments. This type of tiling is useful for spots that exhibit local photobleaching artifacts and irregular probe distribution as they cannot be eliminated from the output pattern. If the artifacts are removed two other sectors of identically-oriented triangles are juxtaposed to create a new lane with different orientation. An extraction mask 1600, overlaid on object of interest 910 (and interposed on grid 900), is derived from a radial spiral that traverses outwardly 1610 originating at the centroid 1615 of the object of interest (see FIG. 16(a)). In addition, an extraction mask 1620, overlaid on object of interest 910 (and interposed on grid 900), is derived from a radial spiral progression that originates at any point on the boundary of the object of interest (see FIG. 16(b)) and traverses inwardly 1630 towards the centroid 1625 of the object of interest.

The extraction tilings discussed below with regard to FIGS. 17–28 are applicable to segmented core geometries that exhibit local morphological artifacts resulting from substrate imperfections, hybridization assay induced degradation or hybridization biasing effects due to environmental conditions (with respect to microarray output patterns). These tilings are particularly applicable as an extraction step for cores that are computationally resampled to a 10-fold–1000-fold higher spatial resolution (as discussed below). These tilings help suppress intraspot artifacts that are amplified due to the scaling process in the synthetic resampling.

Figure 17A:
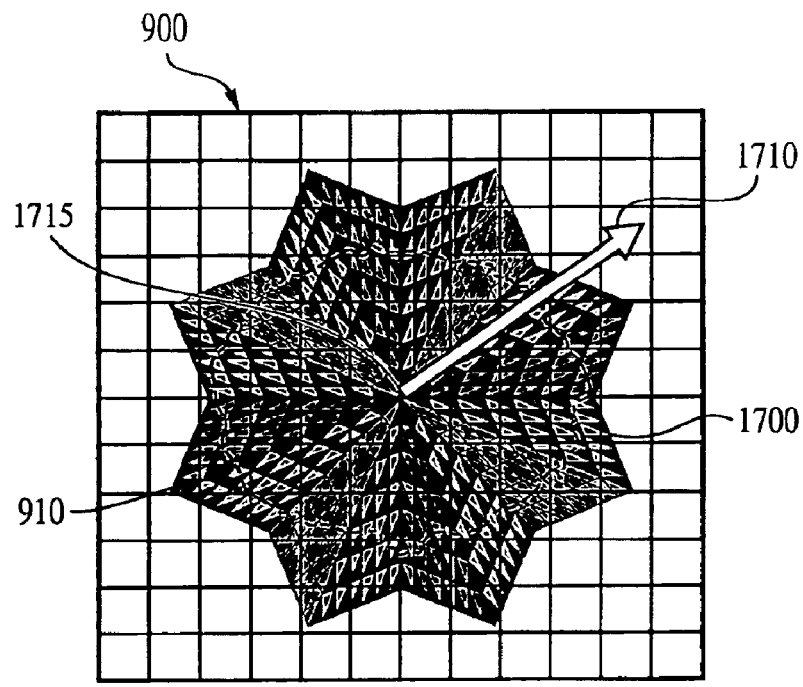
FIG. 17(a) illustrates a ninth embodiment of a tessellated spiral extraction mask overlaying an object of interest with outward radial progression commencing from the centroid of the object of interest.
Figure 17B:
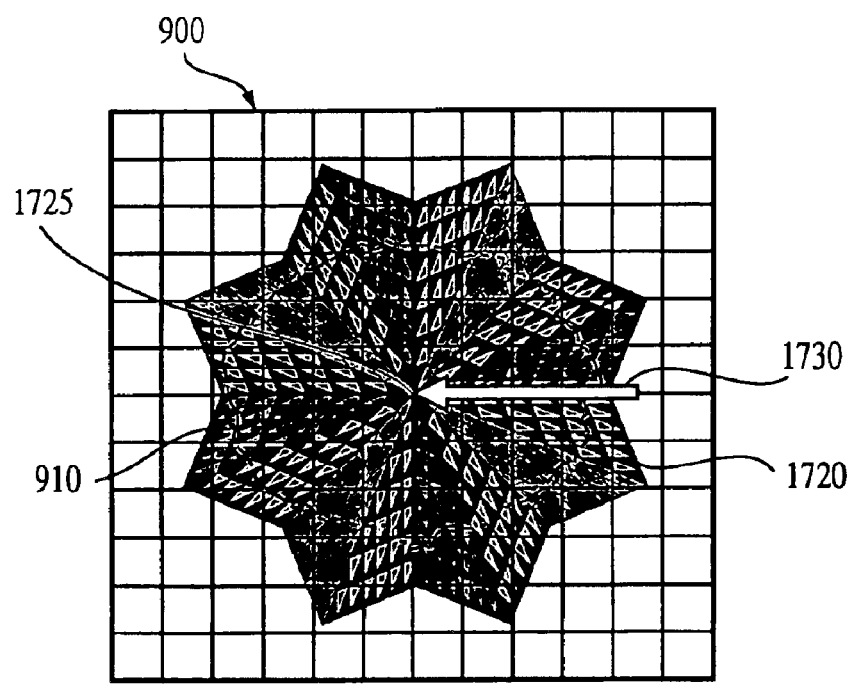
FIG. 17(b) illustrates a ninth embodiment of a tessellated spiral extraction mask overlaying an object of interest with inward radial progression commencing from a boundary point of the object of interest.

With reference to FIGS. 17(a)–17(b), an embodiment is shown with spiral tilings of non-isosceles triangle tiles. An extraction mask 1700, overlaid on object of interest 910 (and interposed on grid 900), is derived from a radial spiral that traverses outwardly 1710 originating at the centroid 1715 of the object of interest (see FIG. 17(a)). In addition, an extraction mask 1720, overlaid on object of interest 910 (and interposed on grid 900), is derived from a radial spiral progression that originates at any point on the boundary of the object of interest (see FIG. 17(b)) and traverses inwardly 1730 towards the centroid 1725 of the object of interest.

Figure 18A:
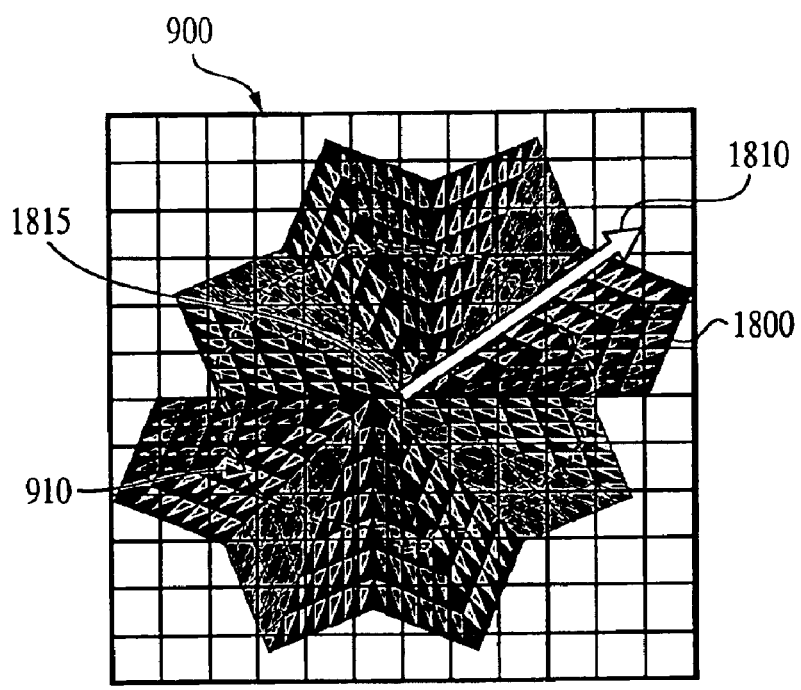
FIG. 18(a) illustrates a tenth embodiment of a tessellated spiral extraction mask overlaying an object of interest with outward radial progression commencing from the centroid of the object of interest.
Figure 18B:
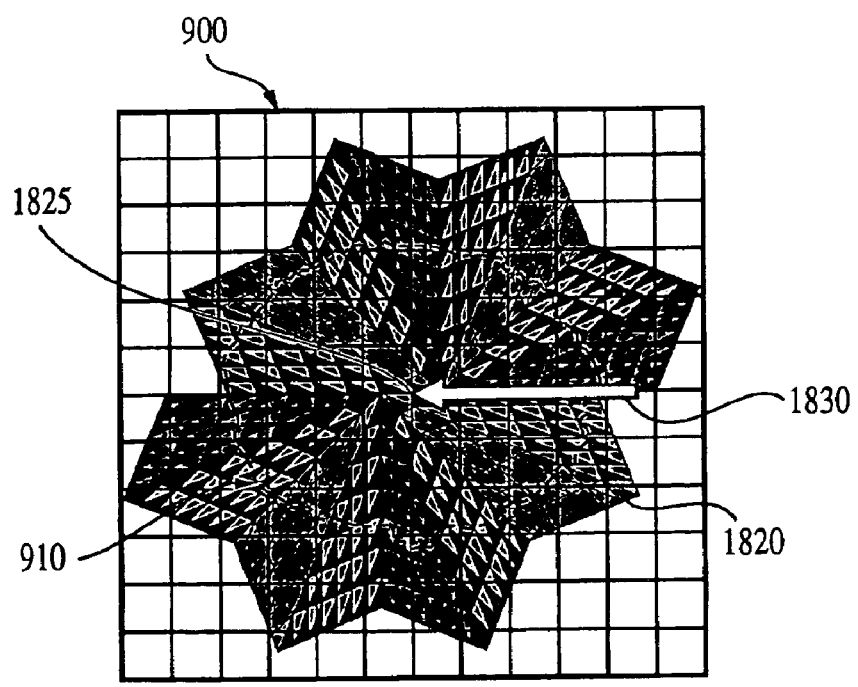
FIG. 18(b) illustrates a tenth embodiment of a tessellated spiral extraction mask overlaying an object of interest with inward radial progression commencing from a boundary point of the object of interest.

With reference to FIGS. 18(a)–18(b), an embodiment is disclosed where two triangular halves are offset to obtain a spiral tiling with kinked spirals. An extraction mask 1800, overlaid on object of interest 910 (and interposed on grid 900), is derived from a radial spiral that traverses outwardly 1810 originating at the centroid 1815 of the object of interest (see FIG. 18(a)). In addition, an extraction mask 1820, overlaid on object of interest 910 (and interposed on grid 900), is derived from a radial spiral progression that originates at any point on the boundary of the object of interest (see FIG. 18(b)) and traverses inwardly 1830 towards the centroid 1825 of the object of interest.

Figure 19A:
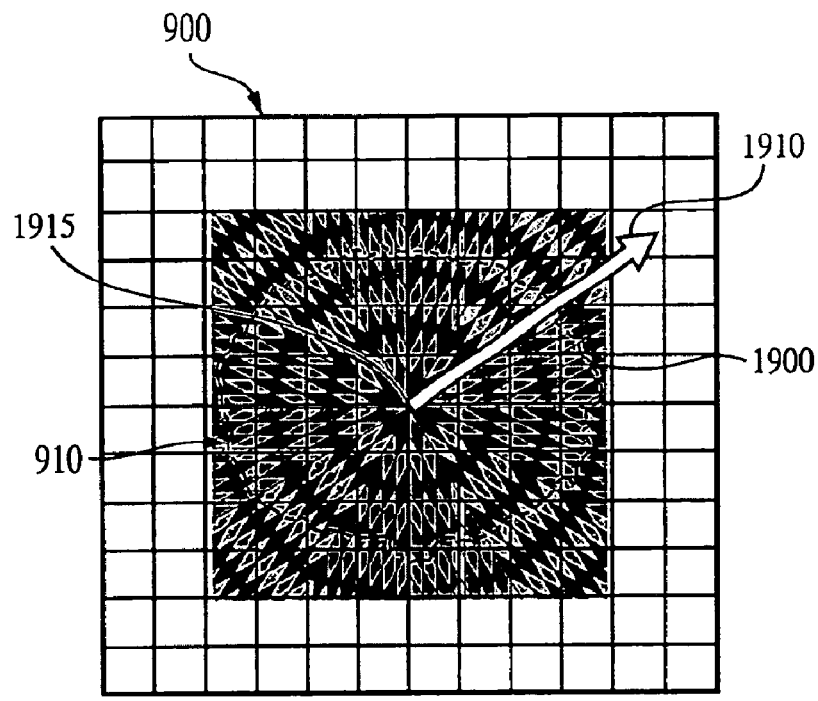
FIG. 19(a) illustrates an eleventh embodiment of a tessellated spiral extraction mask overlaying an object of interest with outward radial progression commencing from the centroid of the object of interest.
Figure 19B:
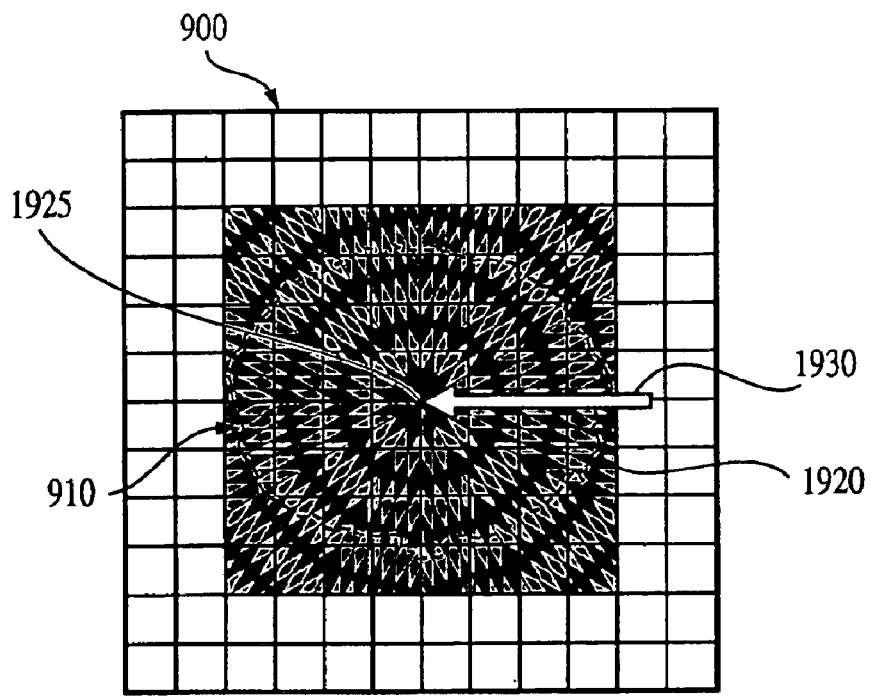
FIG. 19(b) illustrates a eleventh embodiment of a tessellated spiral extraction mask overlaying an object of interest with inward radial progression commencing from a boundary point of the object of interest.

With reference to FIGS. 19(a)–19(b), an embodiment is disclosed where the tiling is offset by two cells. An extraction mask 1900, overlaid on object of interest 910 (and interposed on grid 900), is derived from a radial spiral that traverses outwardly 1910 originating at the centroid 1915 of the object of interest (see FIG. 19(a)). In addition, an extraction mask 1920, overlaid on object of interest 910 (and interposed on grid 900), is derived from a radial spiral progression that originates at any point on the boundary of the object of interest (see FIG. 19(b)) and traverses inwardly 1230 towards the centroid 1925 of the object of interest.

Figure 20A:
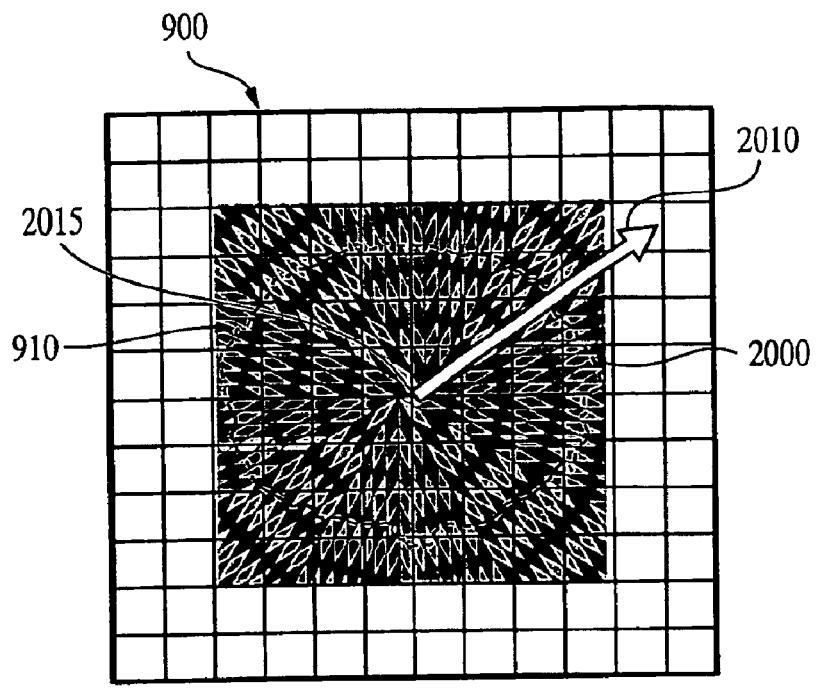
FIG. 20(a) illustrates a twelfth embodiment of a tessellated spiral extraction mask overlaying an object of interest with outward radial progression commencing from the centroid of the object of interest.
Figure 20B:
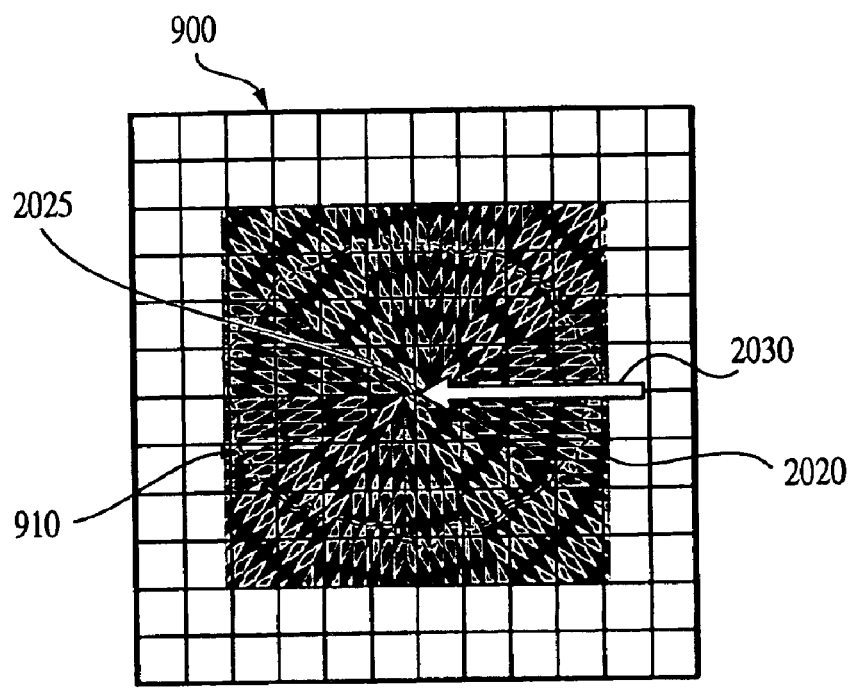
FIG. 20(b) illustrates a twelfth embodiment of a tessellated spiral extraction mask overlaying an object of interest with inward radial progression commencing from a boundary point of the object of interest.

With reference to FIGS. 20(a)–20(b), an embodiment is disclosed where spiral tilings are formed from other radial tessellations with an even number of sectors. This embodiment commences with a rhomboidal tiling. An extraction mask 2000, overlaid on object of interest 910 (and interposed on grid 900), is derived from a radial spiral that traverses outwardly 2010 originating at the centroid 2015 of the object of interest (see FIG. 20(a)). In addition, an extraction mask 2020, overlaid on object of interest 910 (and interposed on grid 900), is derived from a radial spiral progression that originates at any point on the boundary of the object of interest (see FIG. 20(b)) and traverses inwardly 2030 towards the centroid 2025 of the object of interest.

Figure 21A:
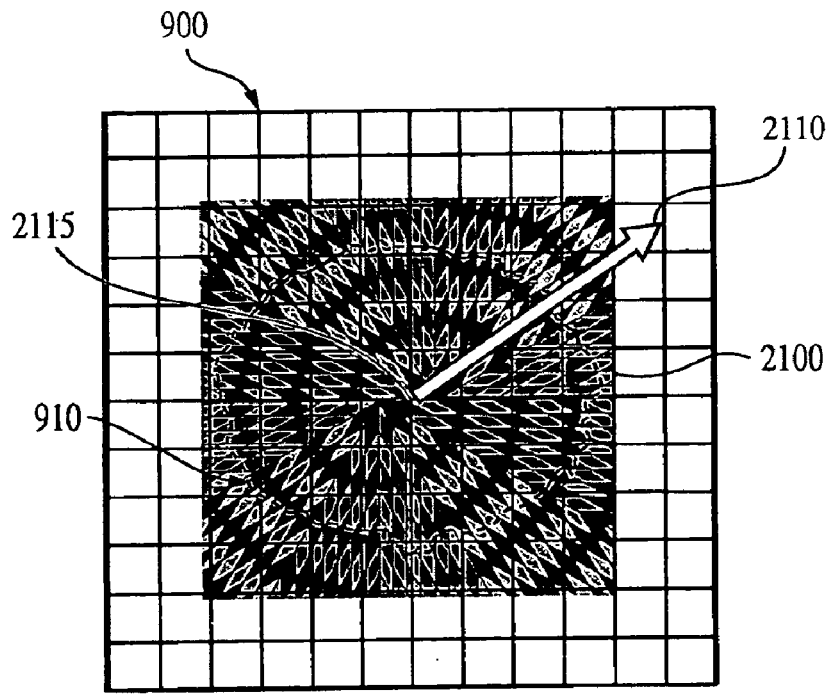
FIG. 21(a) illustrates a thirteenth embodiment of a tessellated spiral extraction mask overlaying an object of interest with outward radial progression commencing from the centroid of the object of interest.
Figure 21B:
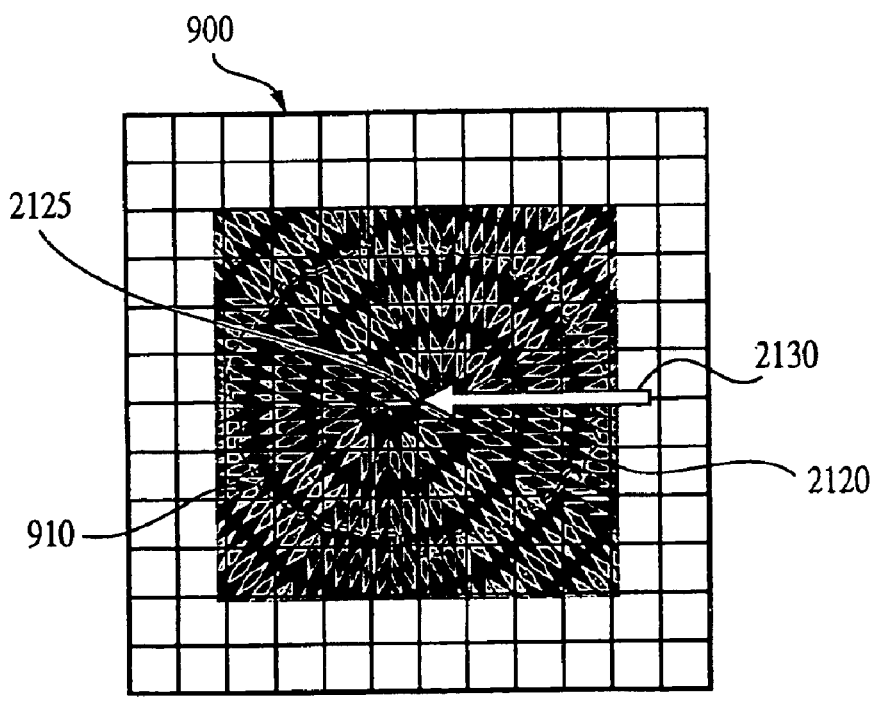
FIG. 21(b) illustrates a thirteenth embodiment of a tessellated spiral extraction mask overlaying an object of interest with inward radial progression commencing from a boundary point of the object of interest.

With reference to FIGS. 21(a)–21(b), an embodiment is disclosed where two halves of a rhombus tiling are offset to obtain a spiral tiling. With this arrangement, the offset tilings juxtapose two sectors of identically-oriented rhombuses to creates a continuous "lane". An extraction mask 2100, overlaid on object of interest 910 (and interposed on grid 900), is derived from a radial spiral that traverses outwardly 2110 originating at the centroid 2115 of the object of interest (see FIG. 21(a)). In addition, an extraction mask 2120, overlaid on object of interest 910 (and interposed on grid 900), is derived from a radial spiral progression that originates at any point on the boundary of the object of interest (see FIG. 21(b)) and traverses inwardly 2130 towards the centroid 2125 of the object of interest.

Figure 22A:
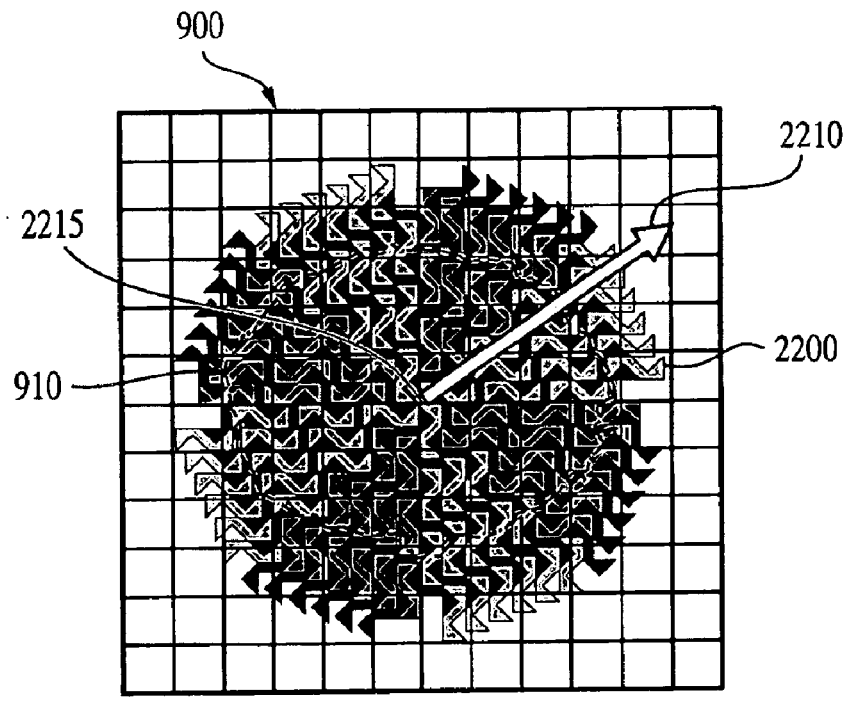
FIG. 22(a) illustrates a fourteenth embodiment of a tessellated spiral extraction mask overlaying an object of interest with outward radial progression commencing from the centroid of the object of interest.
Figure 22B:
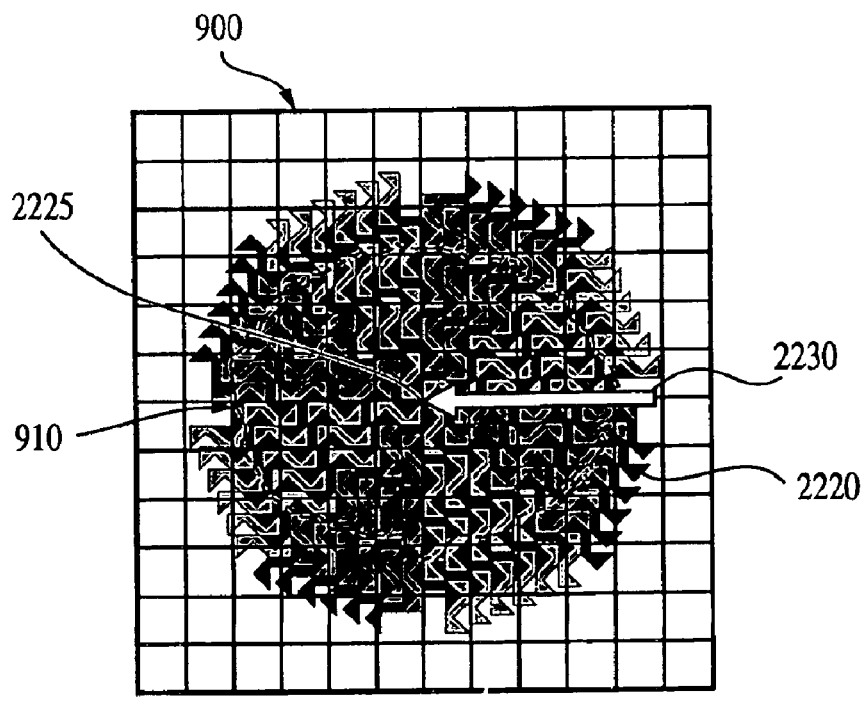
FIG. 22(b) illustrates a fourteenth embodiment of a tessellated spiral extraction mask overlaying an object of interest with inward radial progression commencing from a boundary point of the object of interest.

With reference to FIGS. 22(a)–22(b), an embodiment is disclosed with a tessellation comprised of deformed 45 degree triangles. As all the angles are 45 or 90 degrees, this tiling is especially well suited for segmented core with significant discontinuities. In this arrangement, the two alternating pairs of tiles are mirror images of interlaced pairs. An extraction mask 2200, overlaid on object of interest 910 (and interposed on grid 900), is derived from a radial spiral that traverses outwardly 2210 originating at the centroid 2215 of the object of interest (see FIG. 22(a)). In addition, an extraction mask 2220, overlaid on object of interest 910 (and interposed on grid 900), is derived from a radial spiral progression that originates at any point on the boundary of the object of interest (see FIG. 22(b)) and traverses inwardly 2230 towards the centroid 2225 of the object of interest.

Figure 23A:
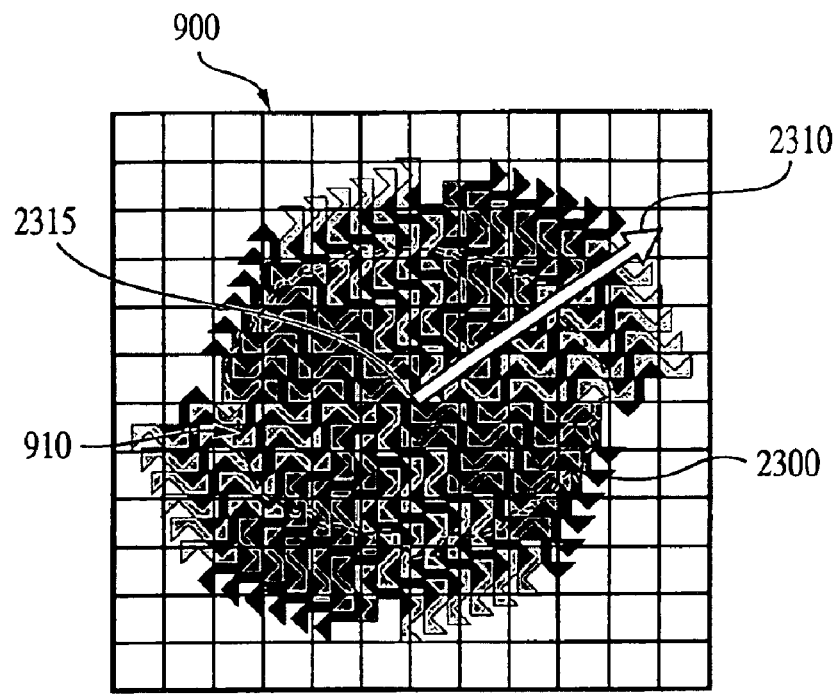
FIG. 23(a) illustrates a fifteenth embodiment of a tessellated spiral extraction mask overlaying an object of interest with outward radial progression commencing from the centroid of the object of interest.
Figure 23B:
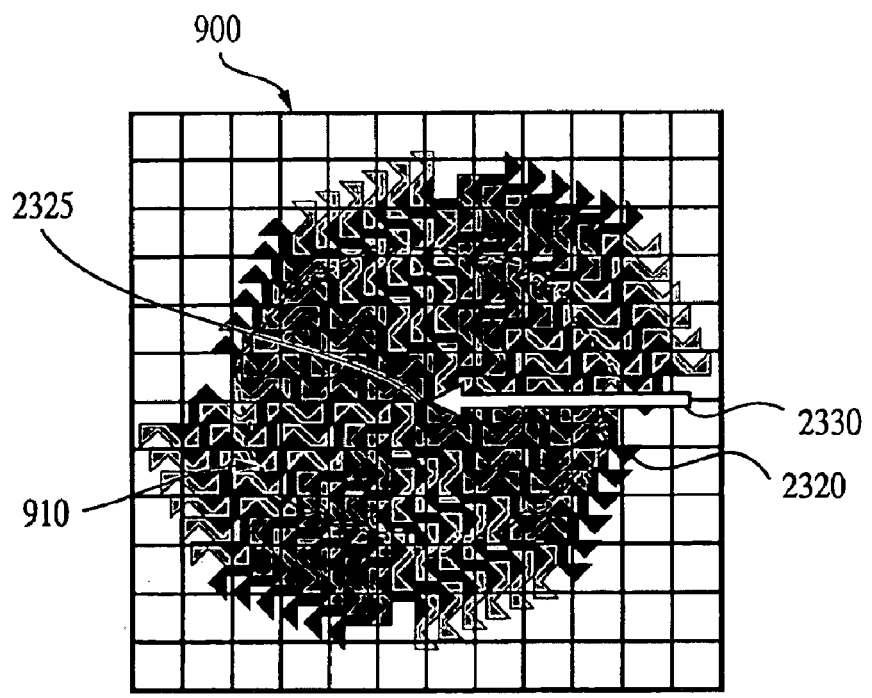
FIG. 23(b) illustrates a fifteenth embodiment of a tessellated spiral extraction mask overlaying an object of interest with inward radial progression commencing from a boundary point of the object of interest.

With reference to FIGS. 23(a)–23(b), an embodiment is shown which is a variation of the embodiment of FIGS. 22(a)–22(b) except that the tiling has been offset by one tile. An extraction mask 2300, overlaid on object of interest 910 (and interposed on grid 900), is derived from a radial spiral that traverses outwardly 2010 originating at the centroid 2315 of the object of interest (see FIG. 23(a)). In addition, an extraction mask 2320, overlaid on object of interest 910 (and interposed on grid 900), is derived from a radial spiral progression that originates at any point on the boundary of the object of interest (see FIG. 23(b)) and traverses inwardly 2330 towards the centroid 2325 of the object of interest.

Figure 24A:
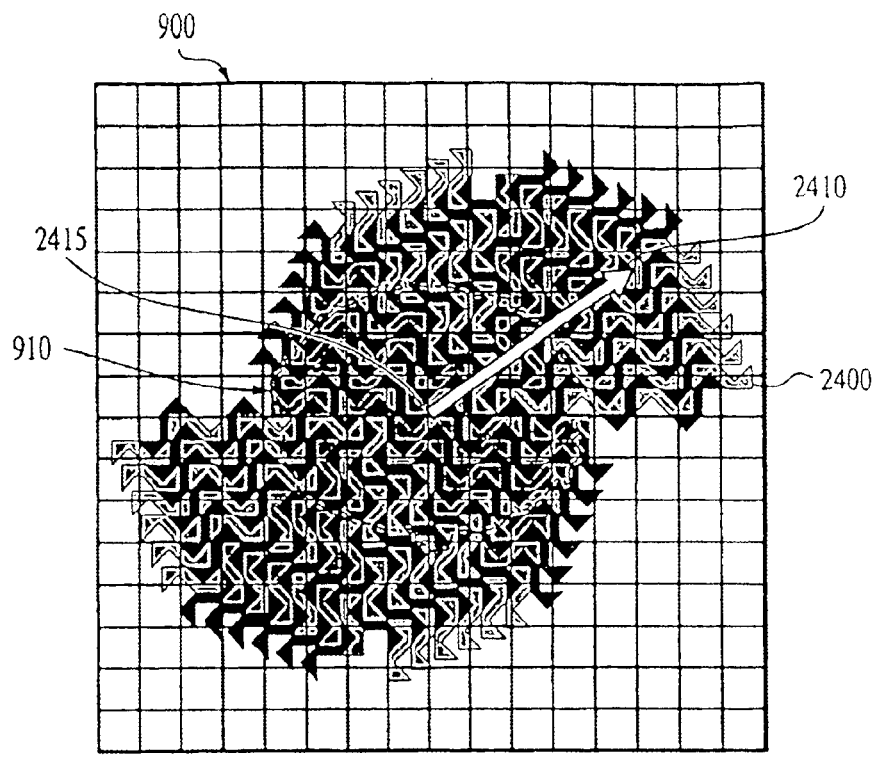
FIG. 24(a) illustrates a sixteenth embodiment of a tessellated spiral extraction mask overlaying an object of interest with outward radial progression commencing from the centroid of the object of interest.
Figure 24B:
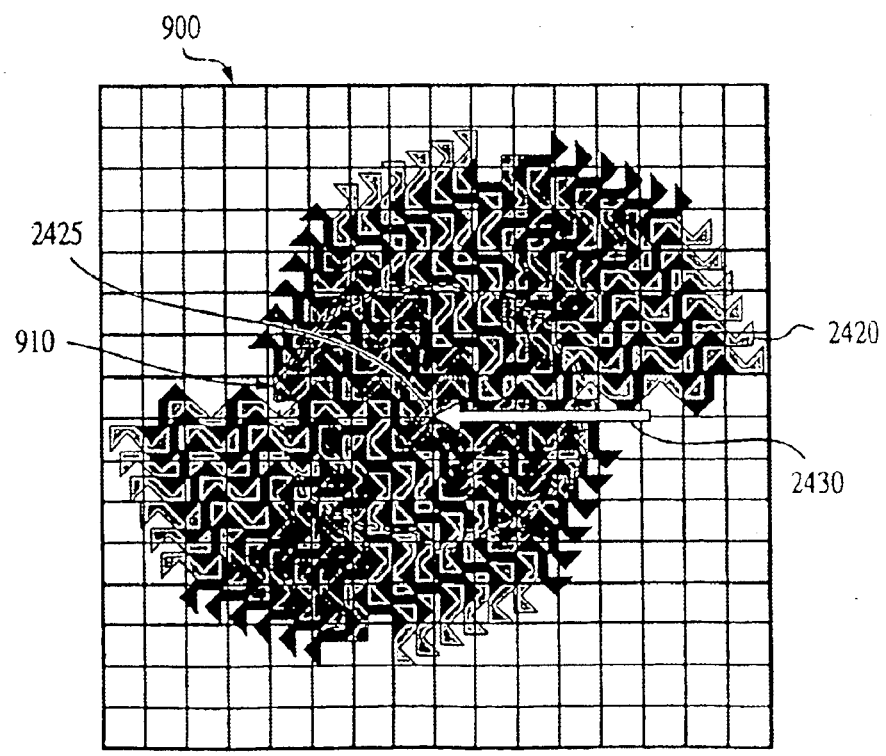
FIG. 24(b) illustrates a sixteenth embodiment of a tessellated spiral extraction mask overlaying an object of interest with inward radial progression commencing from a boundary point of the object of interest.

With reference to FIGS. 24(a)–24(b), an embodiment is disclosed where the tiling has been offset by two tiles to generate a "lane" of identically oriented tiles appears. An extraction mask 2400, overlaid on object of interest 910 (and interposed on grid 900), is derived from a radial spiral that traverses outwardly 2410 originating at the centroid 2415 of the object of interest (see FIG. 24(a)). In addition, an extraction mask 2420, overlaid on object of interest 910 (and interposed on grid 900), is derived from a radial spiral progression that originates at any point on the boundary of the object of interest (see FIG. 24(b)) and traverses inwardly 2430 towards the centroid 2425 of the object of interest.

Figure 25A:
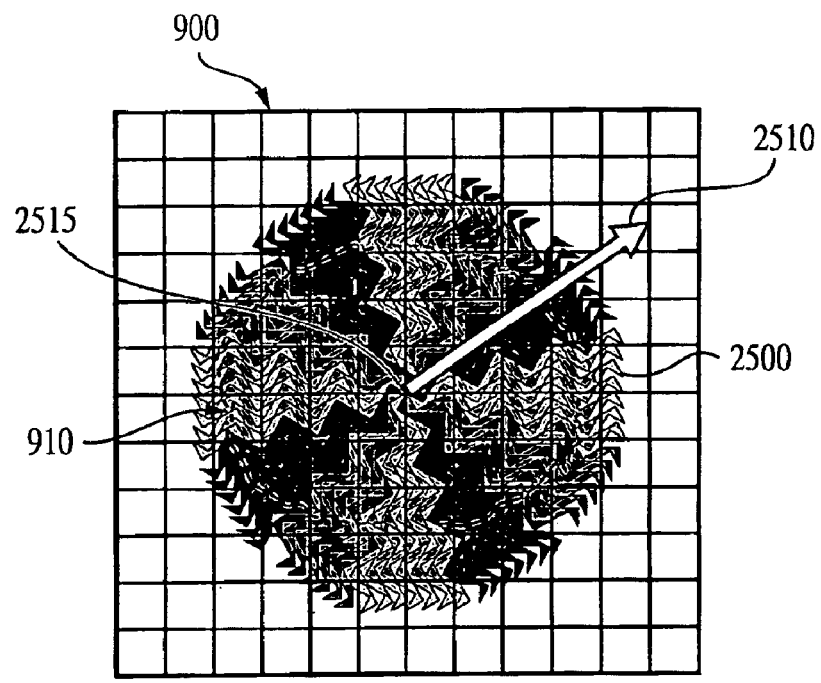
FIG. 25(a) illustrates a seventeenth embodiment of a tessellated spiral extraction mask overlaying an object of interest with outward radial progression commencing from the centroid of the object of interest.
Figure 25B:
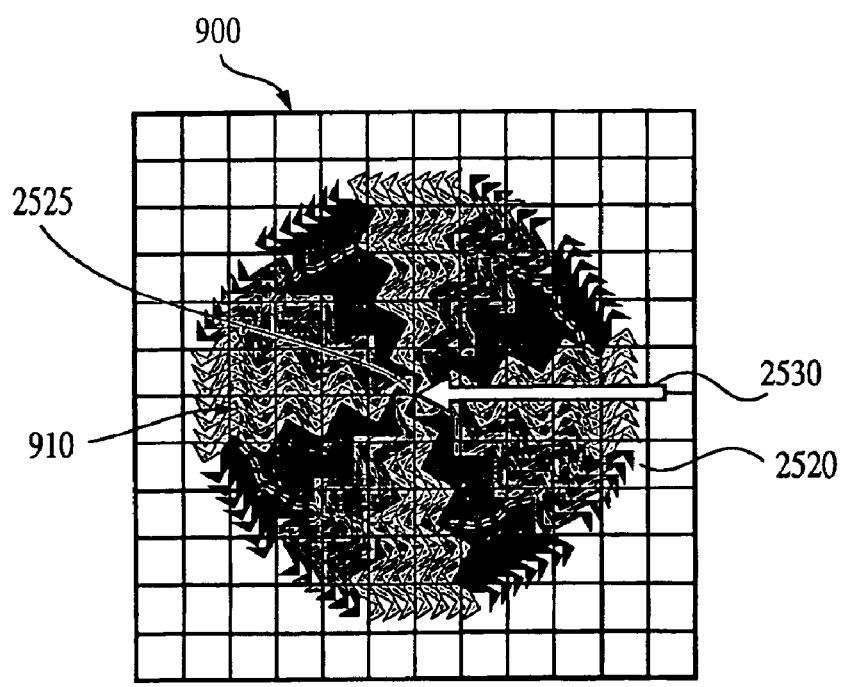
FIG. 25(b) illustrates a seventeenth embodiment of a tessellated spiral extraction mask overlaying an object of interest with inward radial progression commencing from a boundary point of the object of interest.

With reference to FIGS. 25(a)–25(b), an embodiment is disclosed with tiling analogous to the one shown in FIGS. 24(a)–24(b) except the tiles are based on 30-degree triangles. An extraction mask 2500, overlaid on object of interest 910 (and interposed on grid 900), is derived from a radial spiral that traverses outwardly 2510 originating at the centroid 2515 of the object of interest (see FIG. 25(a)). In addition, an extraction mask 2520, overlaid on object of interest 910 (and interposed on grid 900), is derived from a radial spiral progression that originates at any point on the boundary of the object of interest (see FIG. 25(b)) and traverses inwardly 2530 towards the centroid 2525 of the object of interest.

Figure 26A:
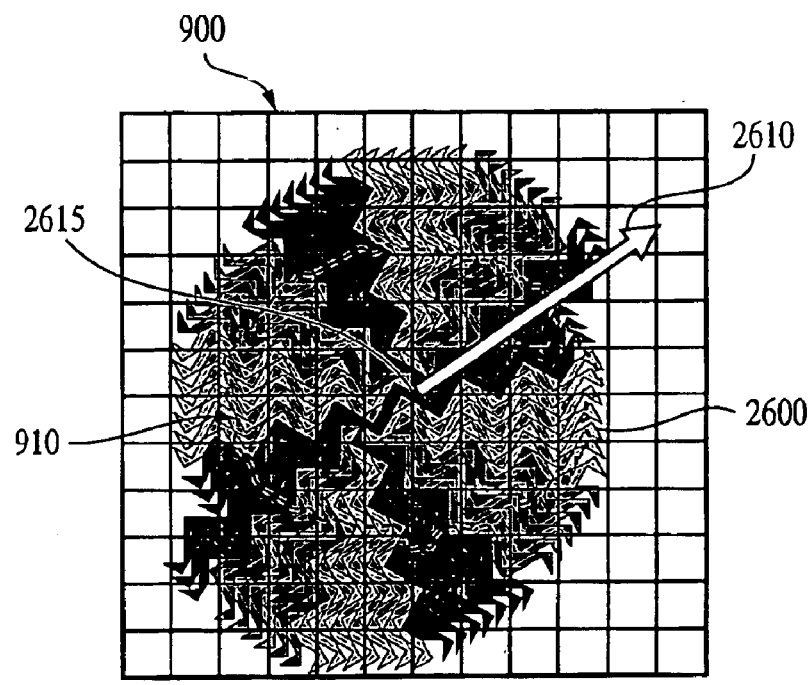
FIG. 26(a) illustrates an eighteenth embodiment of a tessellated spiral extraction mask overlaying an object of interest with outward radial progression commencing from the centroid of the object of interest.
Figure 26B:
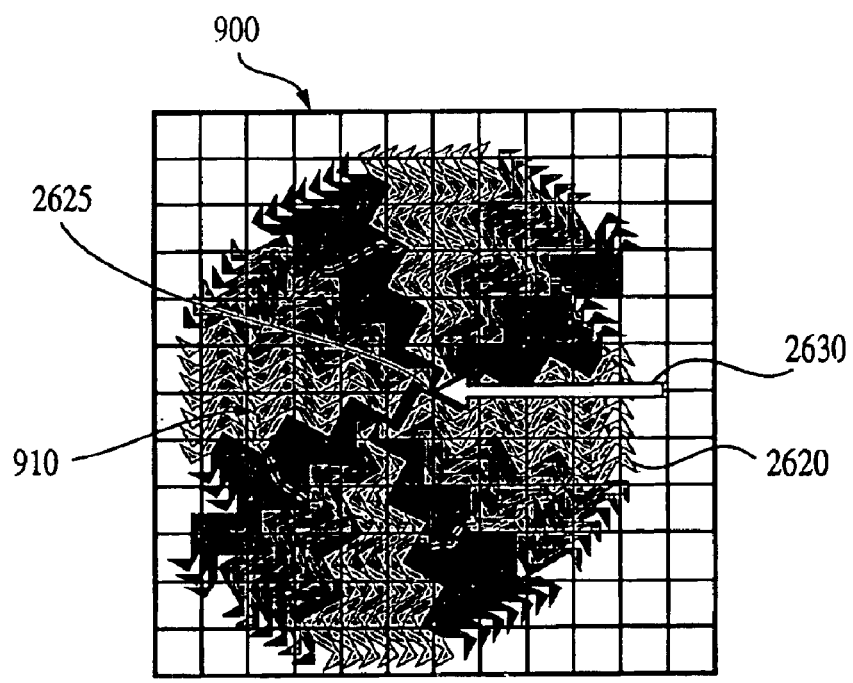
FIG. 26(b) illustrates an eighteenth embodiment of a tessellated spiral extraction mask overlaying an object of interest with inward radial progression commencing from a boundary point of the object of interest.

With reference to FIGS. 26(a)–26(b), an embodiment is disclosed where the tiling of FIGS. 25(a)–25(b) has been offset by one tile. An extraction mask 2600, overlaid on object of interest 910 (and interposed on grid 900), is derived from a radial spiral that traverses outwardly 2610 originating at the centroid 2615 of the object of interest (see FIG. 26(a)). In addition, an extraction mask 2620, overlaid on object of interest 910 (and interposed on grid 900), is derived from a radial spiral progression that originates at any point on the boundary of the object of interest (see FIG. 26(b)) and traverses inwardly 2630 towards the centroid 2625 of the object of interest.

Figure 27A:
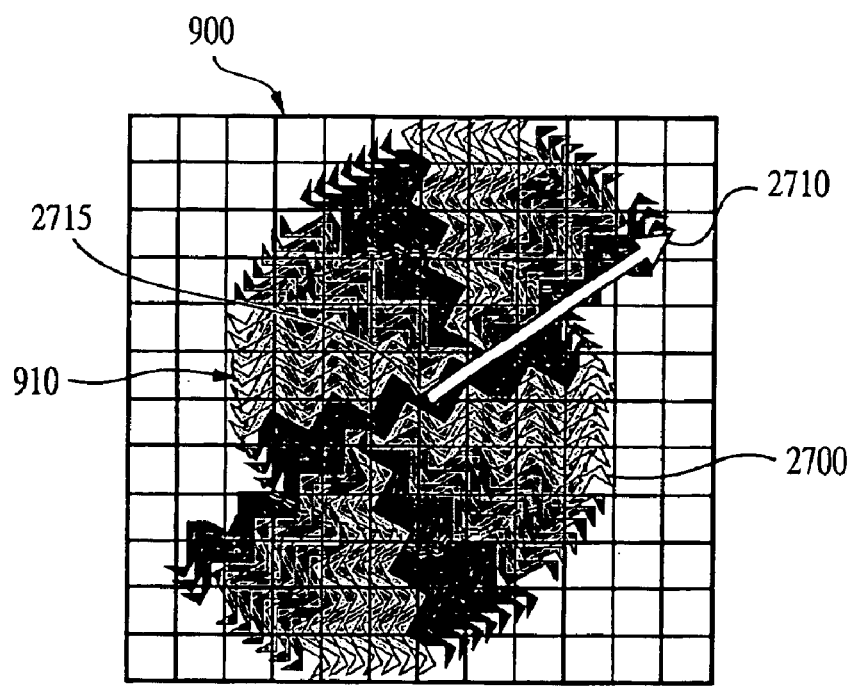
FIG. 27(a) illustrates a nineteenth embodiment of a tessellated spiral extraction mask overlaying an object of interest with outward radial progression commencing from the centroid of the object of interest.
Figure 27B:
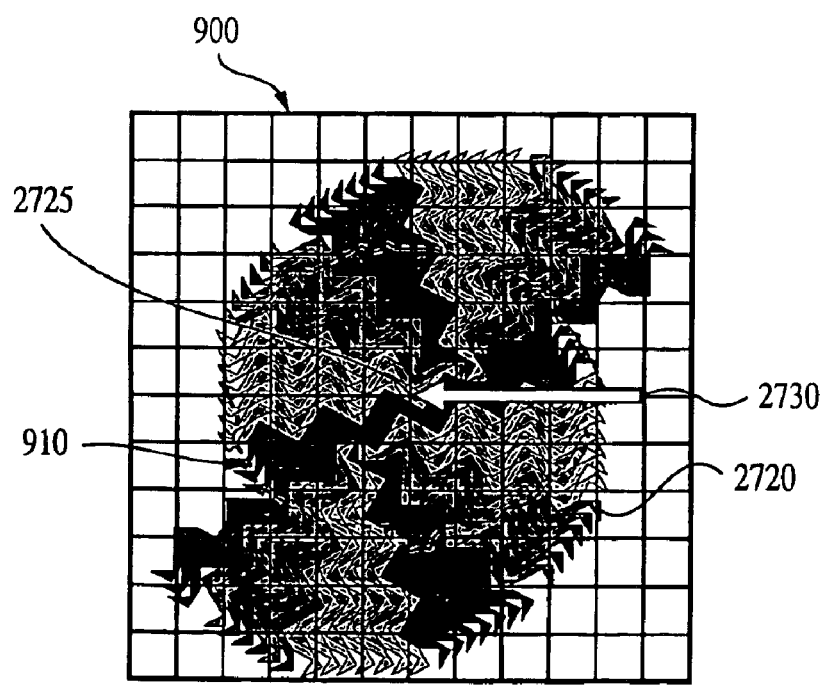
FIG. 27(b) illustrates a nineteenth embodiment of a tessellated spiral extraction mask overlaying an object of interest with inward radial progression commencing from a boundary point of the object of interest.

With reference to FIGS. 27(a)–27(b), an embodiment is disclosed where the tiling of FIGS. 26(a)–26(b) has been offset by two tiles. An extraction mask 2700, overlaid on object of interest 910 (and interposed on grid 900), is derived from a radial spiral that traverses outwardly 2710 originating at the centroid 2715 of the object of interest (see FIG. 27(a)). In addition, an extraction mask 2720, overlaid on object of interest 910 (and interposed on grid 900), is derived from a radial spiral progression that originates at any point on the boundary of the object of interest (see FIG. 27(b)) and traverses inwardly 2030 towards the centroid 2025 of the object of interest.

Figure 28A:
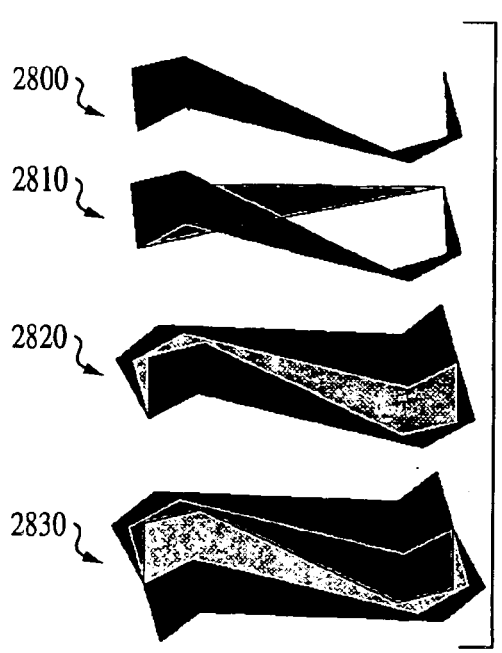
FIG. 28(a) illustrates an exemplary Voderberg spiral extraction mask.
Figure 28B:
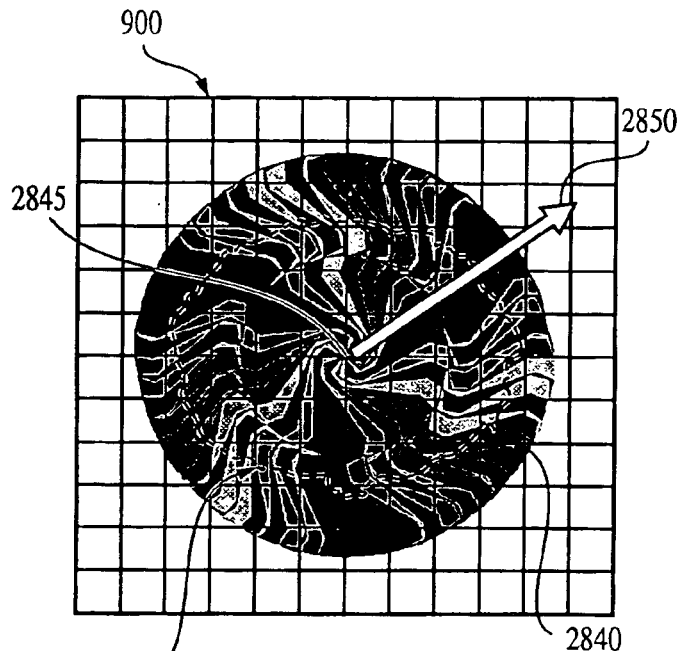
FIG. 28(b) illustrates a twentieth embodiment of a tessellated spiral extraction mask overlaying an object of interest with outward radial progression commencing from the centroid of the object of interest.
Figure 28C:
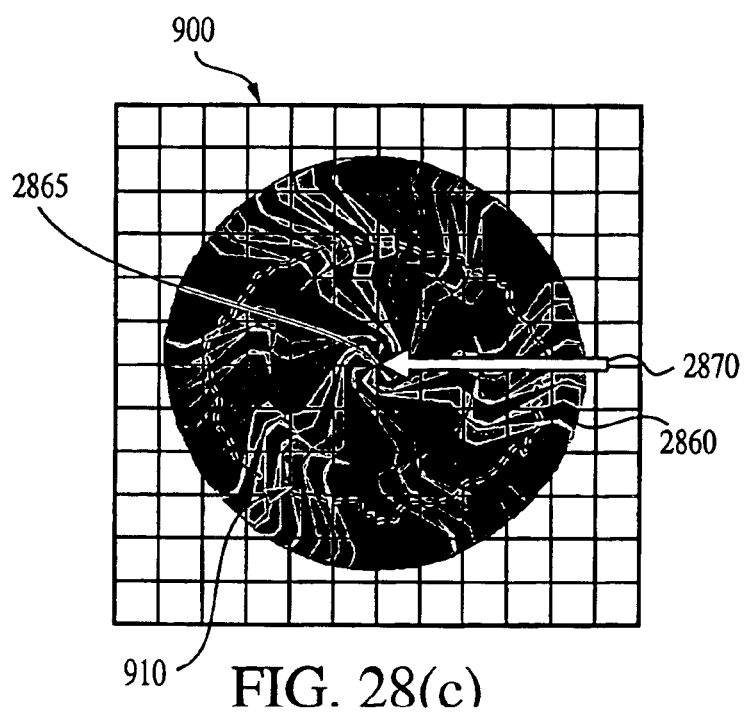
FIG. 28(c) illustrates a twentieth embodiment of a tessellated spiral extraction mask overlaying an object of interest with inward radial progression commencing from a boundary point of the object of interest.

With reference to FIGS. 28(a)–28(c), embodiments are illustrated that use a Voderberg spiral extraction tiling technique for segmented core extraction. The unit tile, as shown in FIG. 28(a) is a bent enneagon. All lettered edges are equal in length. As two tiles fit together with two-fold symmetry, AB is parallel to EF, and DE is parallel to BC. Like most radial tiles, this arrangement can also be derived by deforming a triangle, in this case an isosceles 12-degree triangle. With reference to FIGS. 28(b)–28(c), an embodiment is disclosed where a Voderberg tile is used to construct a simple radial tiling. An extraction mask 2840, overlaid on object of interest 910 (and interposed on grid 900), is derived from a radial spiral that traverses outwardly 2850 originating at the centroid 2845 of the object of interest (see FIG. 28(b)). In addition, an extraction mask 2860, overlaid on object of interest 910 (and interposed on grid 900), is derived from a radial spiral progression that originates at any point on the boundary of the object of interest (see FIG. 28(c)) and traverses inwardly 2870 towards the centroid 2865 of the object of interest.

Figure 29A:
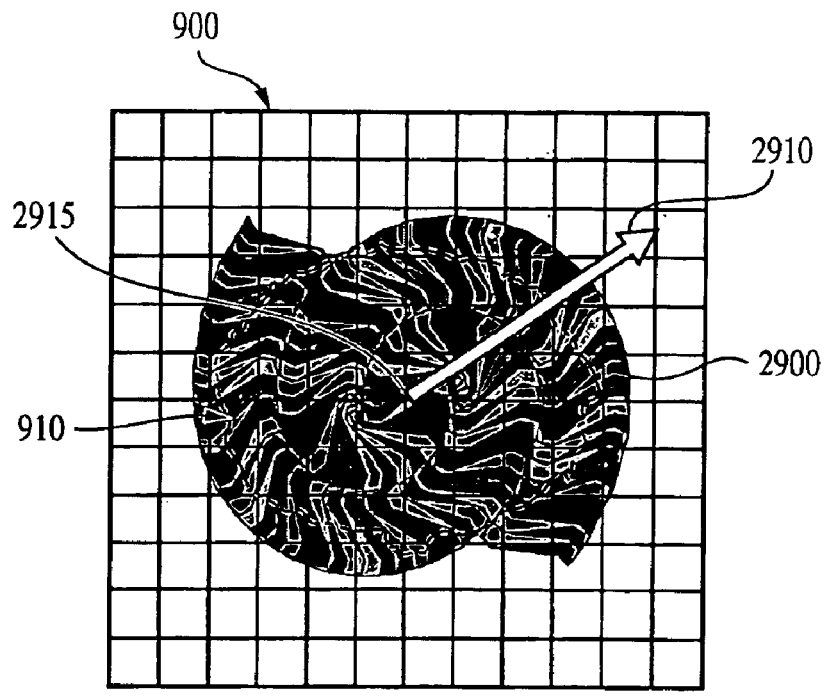
FIG. 29(a) illustrates a twenty-first embodiment of a tessellated spiral extraction mask overlaying an object of interest with outward radial progression commencing from the centroid of the object of interest.
Figure 29B:
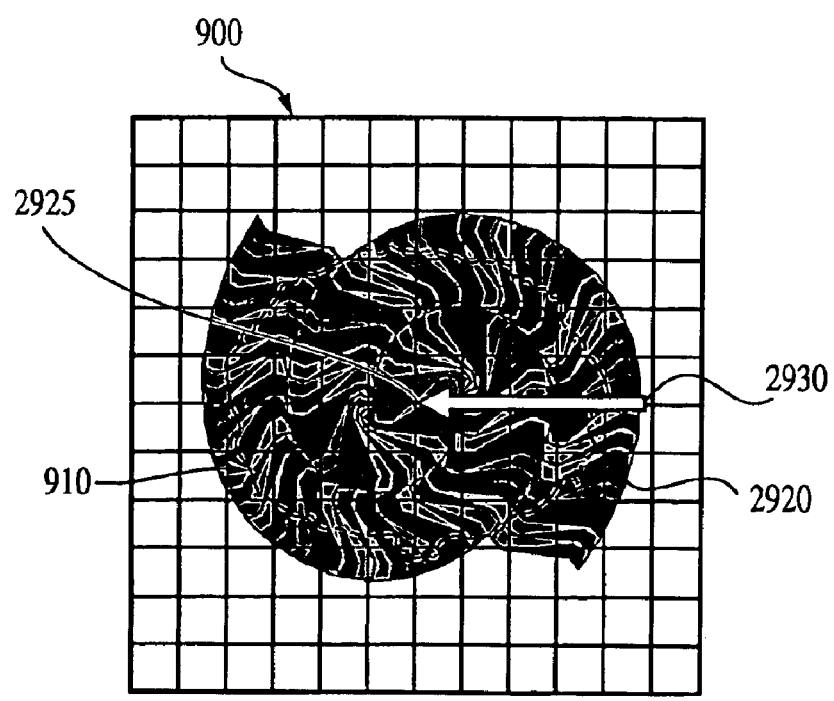
FIG. 29(b) illustrates a twenty-first embodiment of a tessellated spiral extraction mask overlaying an object of interest with inward radial progression commencing from a boundary point of the object of interest.

With reference to FIGS. 29(a)–29(b), an embodiment is shown which uses another variation of spiral Voderberg tilings. The pixellated hooks in the tiles enhance the spiral appearance and the small apical angle of the tiles makes for very smooth curves. This construct can be used to extract and preserve complex polygonal artifacts within segmented core or extracted and computational resampled cores. An extraction mask 2900, overlaid on object of interest 910 (and interposed on grid 900), is derived from a radial spiral that traverses outwardly 2910 originating at the centroid 2915 of the object of interest (see FIG. 29(a)). In addition, an extraction mask 2920, overlaid on object of interest 910 (and interposed on grid 900), is derived from a radial spiral progression that originates at any point on the boundary of the object of interest (see FIG. 29(b)) and traverses inwardly 2930 towards the centroid 2925 of the object of interest.

Figure 30A:
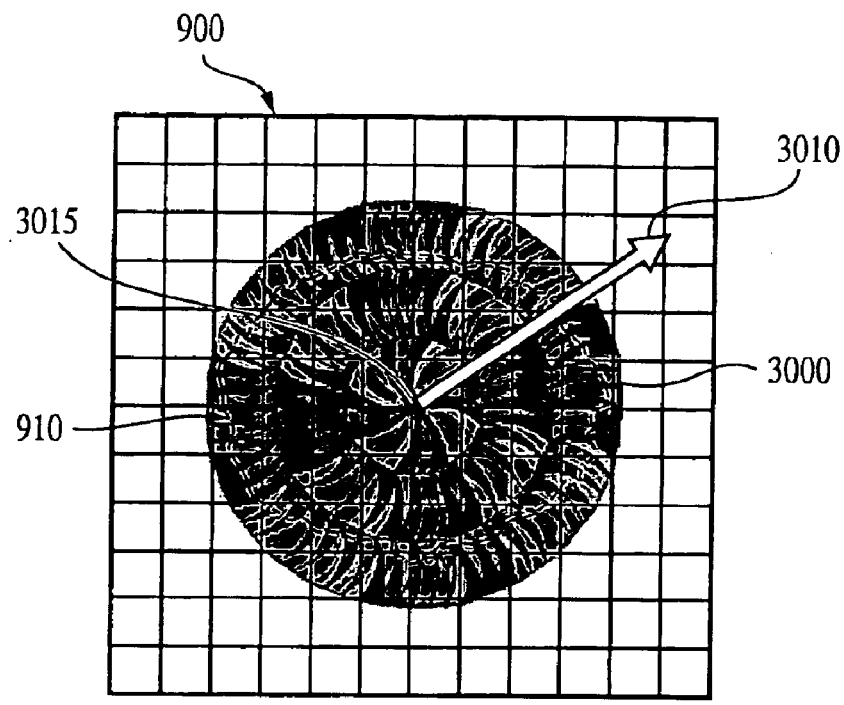
FIG. 30(a) illustrates a twenty-second embodiment of a tessellated spiral extraction mask overlaying an object of interest with outward radial progression commencing from the centroid of the object of interest.
Figure 30B:
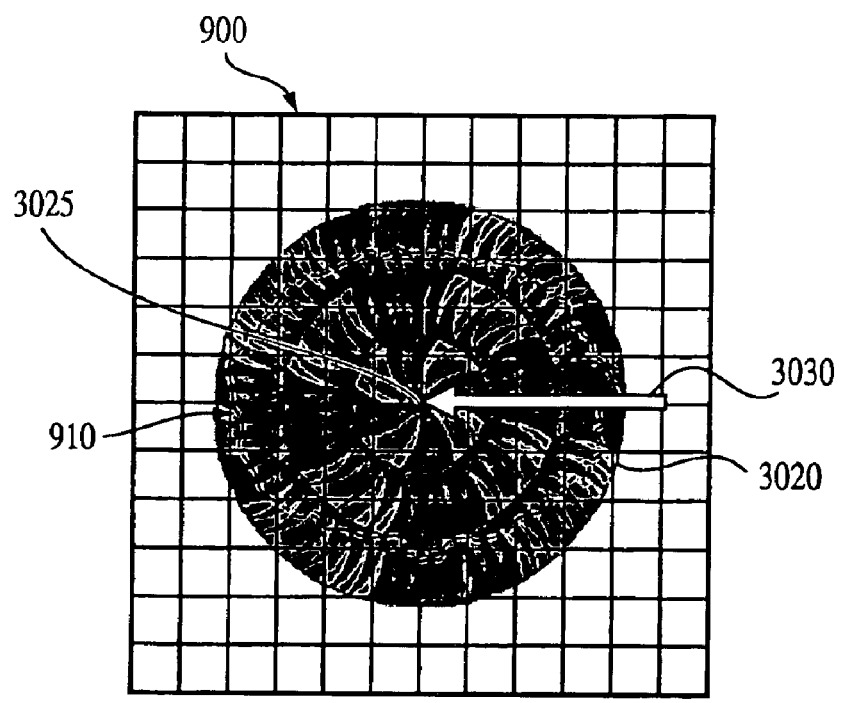
FIG. 30(b) illustrates a twenty-second embodiment of a tessellated spiral extraction mask overlaying an object of interest with inward radial progression commencing from a boundary point of the object of interest.

With reference to FIGS. 30(a)–30(b), a spiral extraction utilizing a bent wedge tiling is illustrated. This spiral extraction technique comprises an isosceles 15-degree triangle distorted into a curved enneagon. The apical angle is 15 degrees, the three successive angles on each side are 165 degrees, and the two end angles are 60 and 105 degrees. The 165 degree angles are also the interior angles of a 24-gon, meaning the intraspot tiles can fit together in a myriad of ways. As seen here, the tiles can form a simple radial pattern. As the tiles can curve in either direction within each annulus, this arrangement permits an infinite number of tilings. An extraction mask 3000, overlaid on object of interest 910 (and interposed on grid 900), is derived from a radial spiral that traverses outwardly 3010 originating at the centroid 3015 of the object of interest (see FIG. 30(a)). In addition, an extraction mask 3020, overlaid on object of interest 910 (and interposed on grid 900), is derived from a radial spiral progression that originates at any point on the boundary of the object of interest (see FIG. 30(b)) and traverses inwardly 3030 towards the centroid 3025 of the object of interest.

Figure 31A:
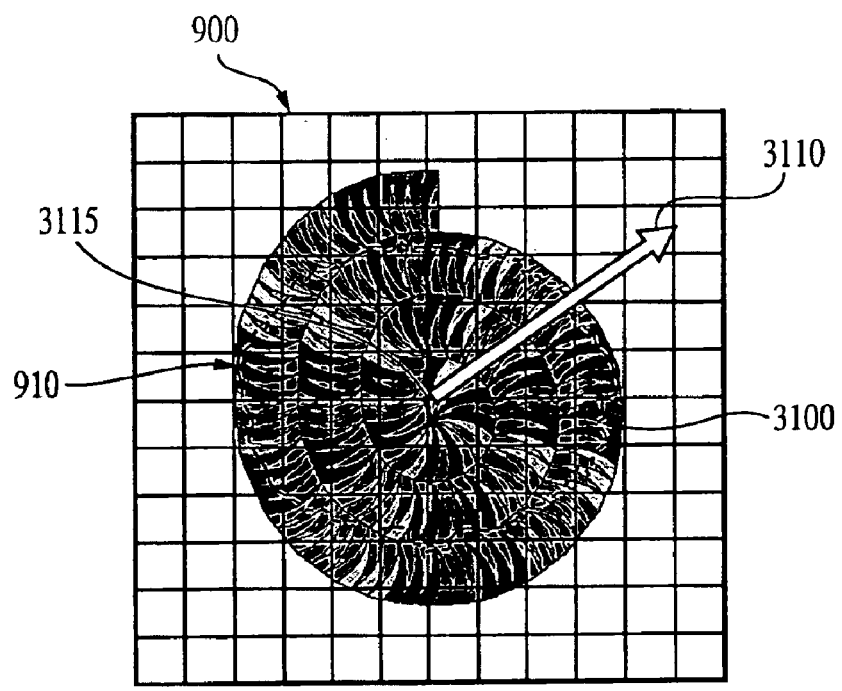
FIG. 31(a) illustrates a twenty-third embodiment of a tessellated spiral extraction mask overlaying an object of interest with outward radial progression commencing from the centroid of the object of interest.
Figure 31B:
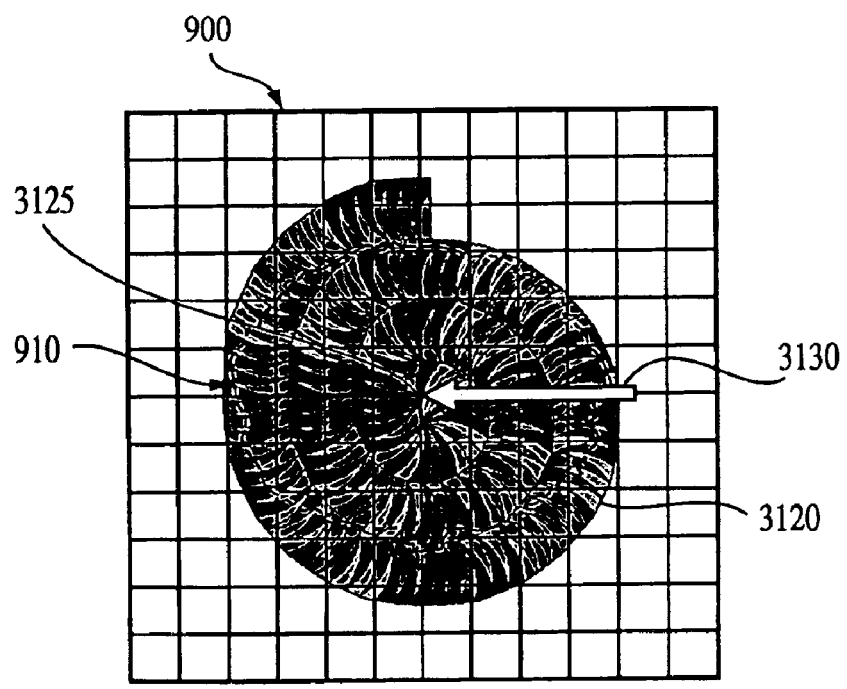
FIG. 31(b) illustrates a twenty-third embodiment of a tessellated spiral extraction mask overlaying an object of interest with inward radial progression commencing from a boundary point of the object of interest.

With reference to FIGS. 31(a)–31(b), an embodiment is disclosed where the bent-wedge tiling described above is offset in a variety of ways to create extraction spirals. In addition to the familiar ways of creating spirals, here, a 90-degree sector has been offset to make a spiral. An extraction mask 3100, overlaid on object of interest 910 (and interposed on grid 900), is derived from a radial spiral that traverses outwardly 3110 originating at the centroid 3115 of the object of interest (see FIG. 31(a)). In addition, an extraction mask 3120, overlaid on object of interest 910 (and interposed on grid 900), is derived from a radial spiral progression that originates at any point on the boundary of the object of interest (see FIG. 30(b)) and traverses inwardly 3130 towards the centroid 3125 of the object of interest.

Figure 32A:
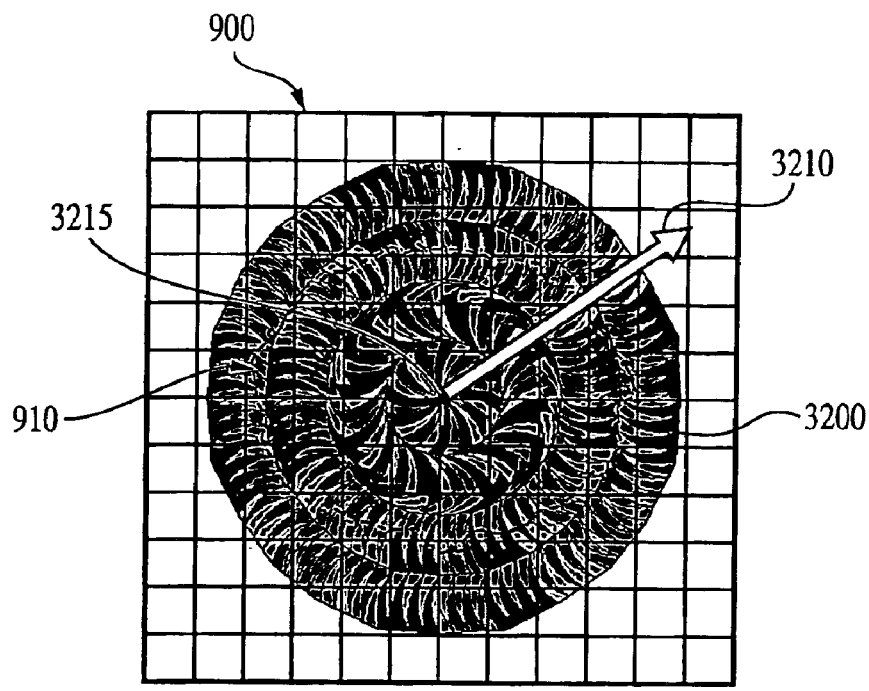
FIG. 32(a) illustrates a twenty-fourth embodiment of a tessellated spiral extraction mask overlaying an object of interest with outward radial progression commencing from the centroid of the object of interest.
Figure 32B:
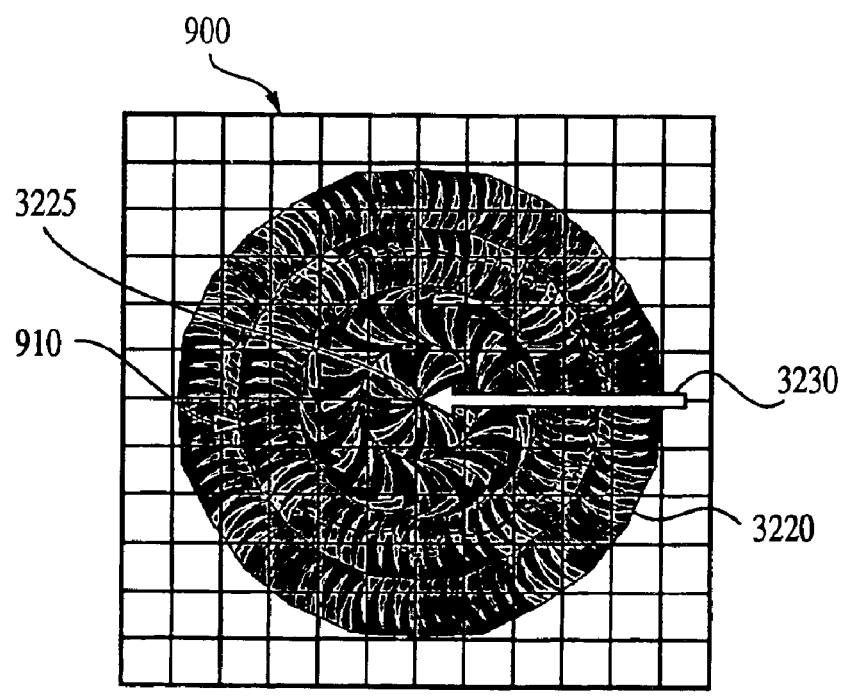
FIG. 32(b) illustrates a twenty-fourth embodiment of a tessellated spiral extraction mask overlaying an object of interest with inward radial progression commencing from a boundary point of the object of interest.

With reference to FIGS. 32(a)–32(b), an extraction mask 3200, overlaid on object of interest 910 (and interposed on grid 900), is derived from a radial spiral that traverses outwardly 3210 originating at the centroid 3215 of the object of interest (see FIG. 32(a)). In addition, an extraction mask 3220, overlaid on object of interest 910 (and interposed on grid 900), is derived from a radial spiral progression that originates at any point on the boundary of the object of interest (see FIG. 32(b)) and traverses inwardly 3230 towards the centroid 3225 of the object of interest.

Figure 33A:
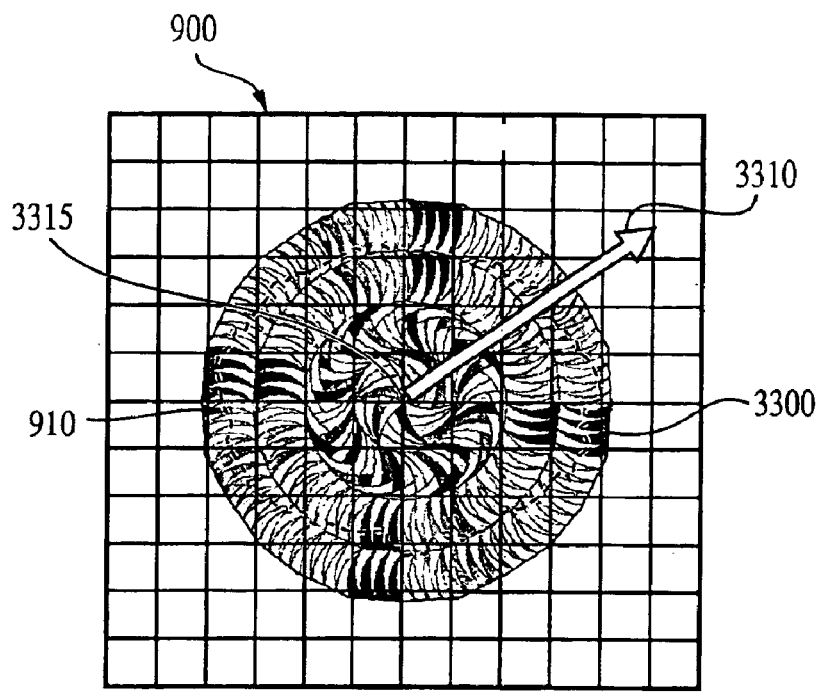
FIG. 33(a) illustrates a twenty-fifth embodiment of a tessellated spiral extraction mask overlaying an object of interest with outward radial progression commencing from the centroid of the object of interest.
Figure 33B:
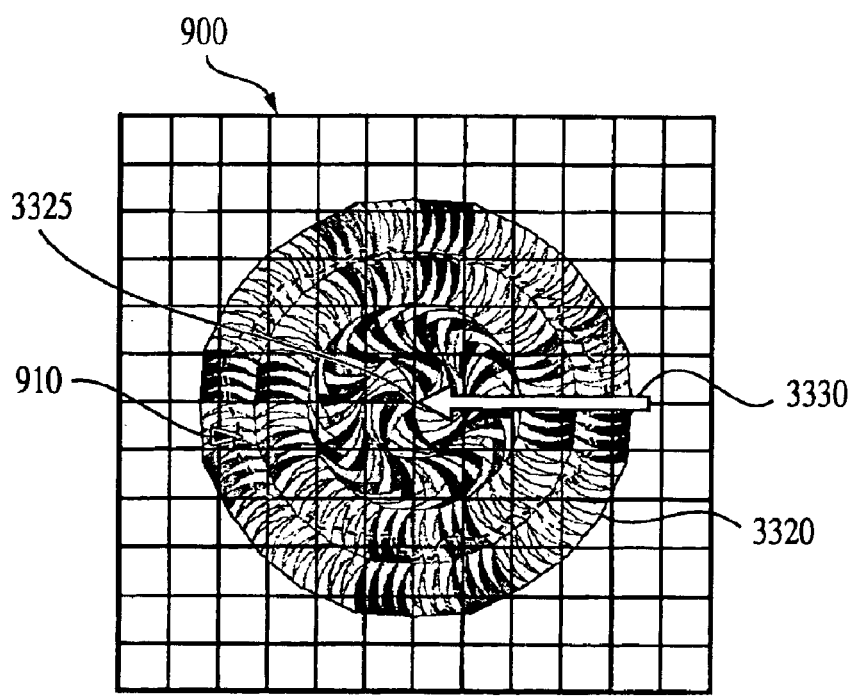
FIG. 33(b) illustrates a twenty-fifth embodiment of a tessellated spiral extraction mask overlaying an object of interest with inward radial progression commencing from a boundary point of the object of interest.

With reference to FIGS. 33(a)–33(b), an embodiment of an offset variation of the Hirschorn tiling of FIGS. 32(a)–32(b) is disclosed. An extraction mask 3300, overlaid on object of interest 910 (and interposed on grid 900), is derived from a radial spiral that traverses outwardly 3310 originating at the centroid 3315 of the object of interest (see FIG. 33(a)). In addition, an extraction mask 3320, overlaid on object of interest 910 (and interposed on grid 900), is derived from a radial spiral progression that originates at any point on the boundary of the object of interest (see FIG. 33(b)) and traverses inwardly 3330 towards the centroid 3325 of the object of interest.

Figure 34A:
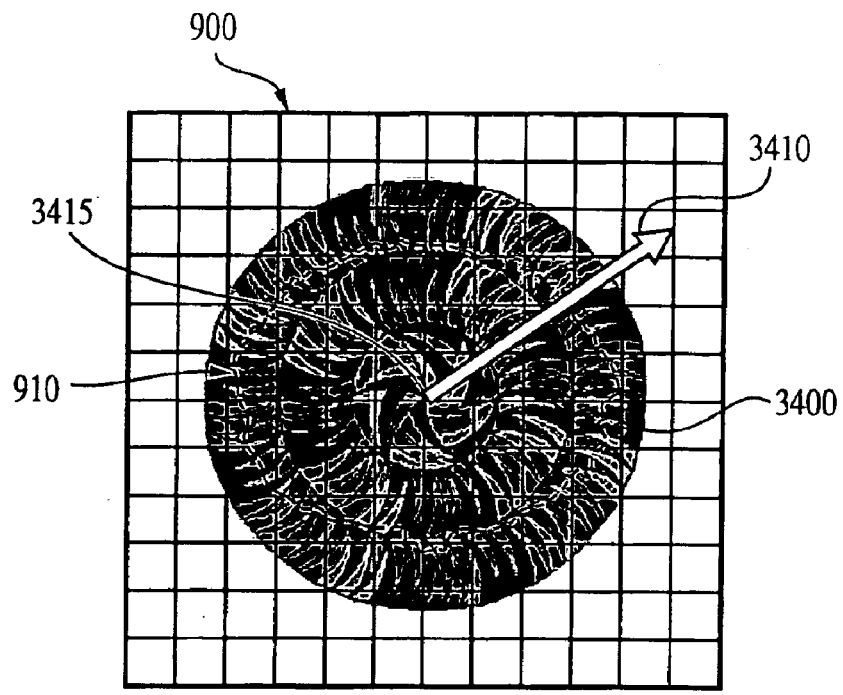
FIG. 34(a) illustrates a twenty-sixth embodiment of a tessellated spiral extraction mask overlaying an object of interest with outward radial progression commencing from the centroid of the object of interest.
Figure 34B:
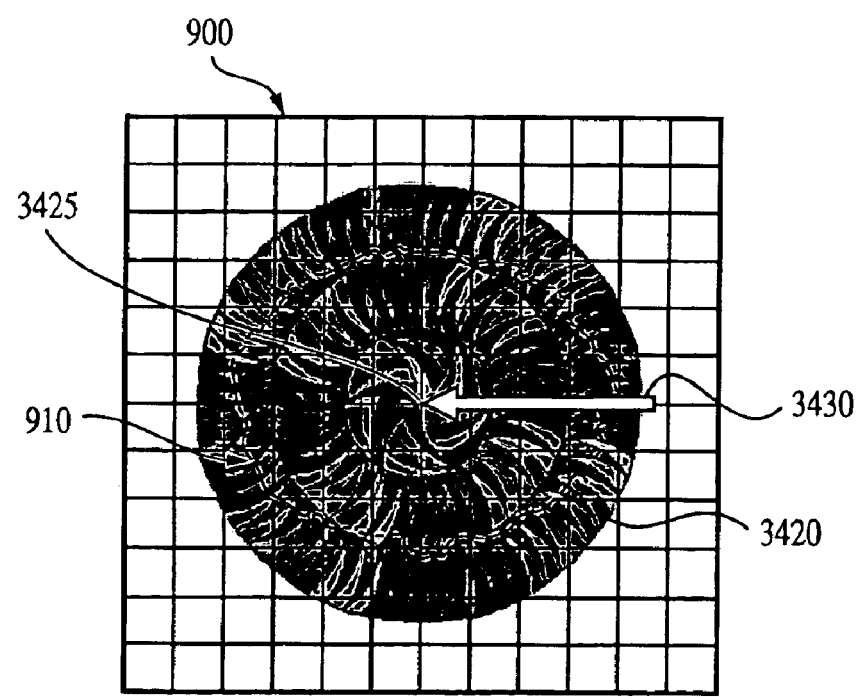
FIG. 34(b) illustrates a twenty-sixth embodiment of a tessellated spiral extraction mask overlaying an object of interest with inward radial progression commencing from a boundary point of the object of interest.

With reference to FIGS. 34(a)–34(b), an embodiment is disclosed where the handedness of the central rosette and the next annulus of the tiling have been reversed and the radial angle is biased in the clockwise direction compared to the embodiment of FIGS. 33(a)–33(b). An extraction mask 3400, overlaid on object of interest 910 (and interposed on grid 900), is derived from a radial spiral that traverses outwardly 3410 originating at the centroid 3415 of the object of interest (see FIG. 34(a)). In addition, an extraction mask 3420, overlaid on object of interest 910 (and interposed on grid 900), is derived from a radial spiral progression that originates at any point on the boundary of the object of interest (see FIG. 34(b)) and traverses inwardly 3430 towards the centroid 3425 of the object of interest.

Figure 35A:
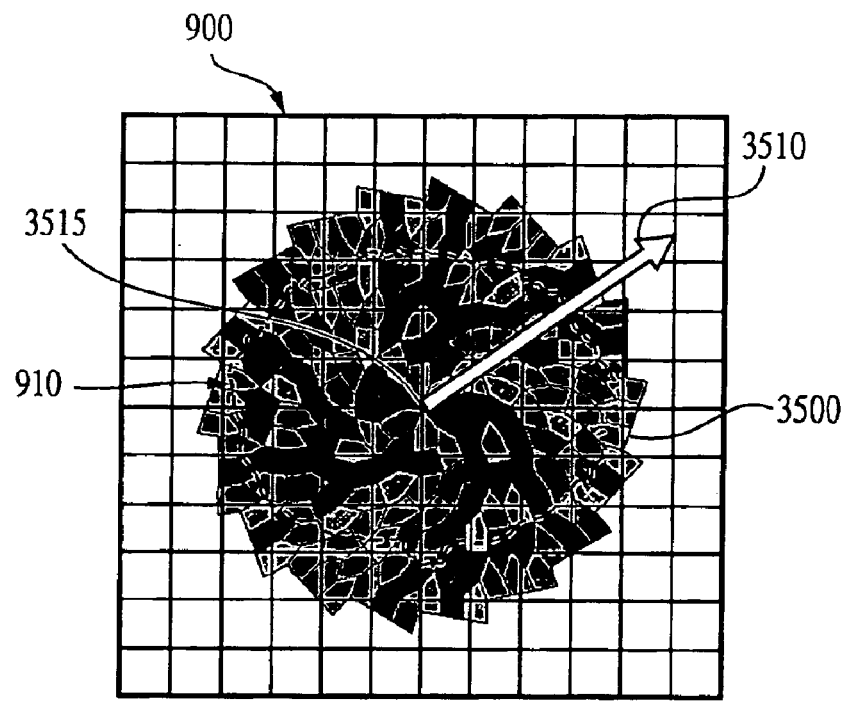
FIG. 35(a) illustrates a twenty-seventh embodiment of a tessellated spiral extraction mask overlaying an object of interest with outward radial progression commencing from the centroid of the object of interest.
Figure 35B:
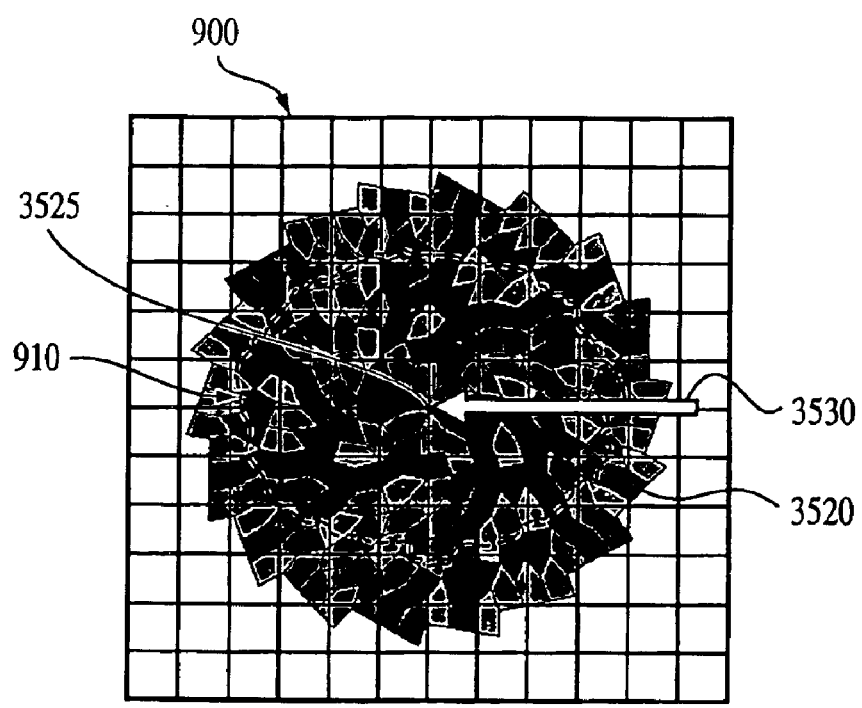
FIG. 35(b) illustrates a twenty-seventh embodiment of a tessellated spiral extraction mask overlaying an object of interest with inward radial progression commencing from a boundary point of the object of interest.

With reference to FIGS. 35(a)–35(b), a spiral extraction utilizing Hirschorn tiling is disclosed. This tiling consists of equilateral pentagons. In order, the vertex angles are 60, 160, 80, 100 and 140 degrees. The pentagon can be considered an equilateral triangle attached to a rhombus with 80-degree acute angles. Beyond the initial rosette, the tiling consists of radial sectors made up of pairs of mirror-image pentagons. The pairs stack in the usual triangular stacking pattern.. An extraction mask 3500, overlaid on object of interest 910 (and interposed on grid 900), is derived from a radial spiral that traverses outwardly 3010 originating at the centroid 3515 of the object of interest (see FIG. 35(a)). In addition, an extraction mask 3520, overlaid on object of interest 910 (and interposed on grid 900), is derived from a radial spiral progression that originates at any point on the boundary of the object of interest (see FIG. 35(b)) and traverses inwardly 3530 towards the centroid 3525 of the object of interest.

Figure 36A:
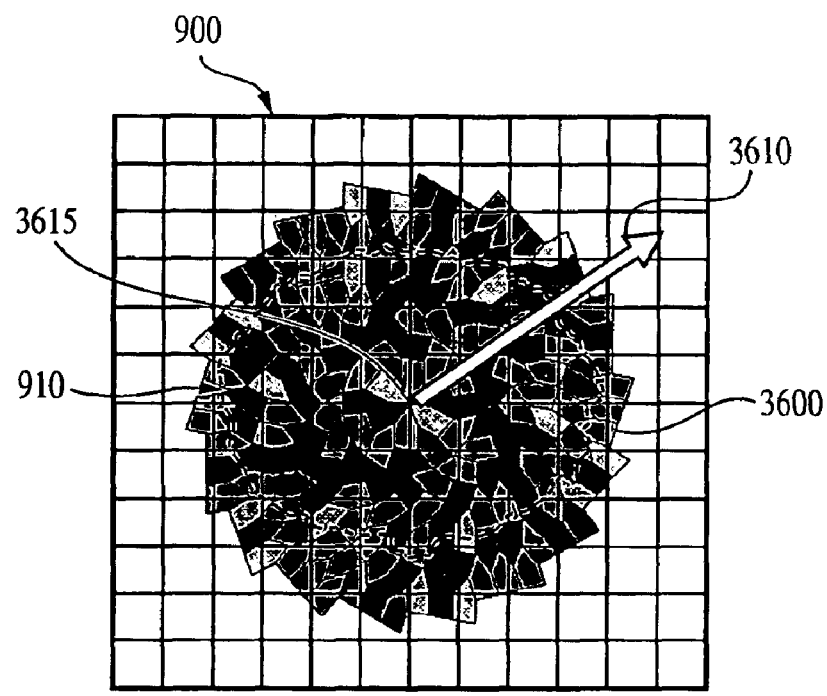
FIG. 36(a) illustrates a twenty-eighth embodiment of a tessellated spiral extraction mask overlaying an object of interest with outward radial progression commencing from the centroid of the object of interest.
Figure 36B:
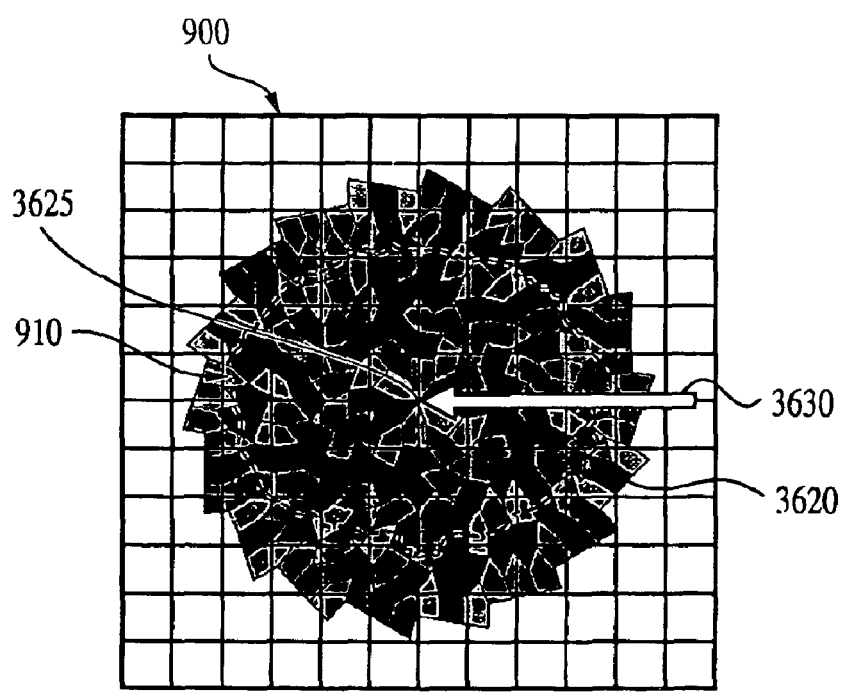
FIG. 36(b) illustrates a twenty-eighth embodiment of a tessellated spiral extraction mask overlaying an object of interest with inward radial progression commencing from a boundary point of the object of interest.

With reference to FIGS. 36(a)–36(b), an embodiment is disclosed where the handedness of the central rosette and the next annulus of the tiling have been reversed as compared to FIGS. 35(a)–35(b). An extraction mask 3600, overlaid on object of interest 910 (and interposed on grid 900), is derived from a radial spiral that traverses outwardly 3010 originating at the centroid 3615 of the object of interest (see FIG. 36(a)). In addition, an extraction mask 3620, overlaid on object of interest 910 (and interposed on grid 900), is derived from a radial spiral progression that originates at any point on the boundary of the object of interest (see FIG. 36(b)) and traverses inwardly 3630 towards the centroid 3625 of the object of interest.

In some embodiments, the objects of interest are distributed geometrically irregular on the array. With these types of arrangements, the boundary of each object of interest is identified and the extraction algorithm traverses the object of interest in a spiral trajectory (outward logarithmic spiral or inward). This results in a linear vector of extracted pixels. As illustrated in FIGS. 8–36 above, cores can be mapped to numerous types of spirals. Each of such spirals has an equation driving its creation (in modeling). The generator equation corresponding to a specific spiral extraction type provides the trajectory to be traversed. Traversing a spiral trajectory implies the process of computationally traversing the pixels in the segmented object.

The following steps describe how a spiral extraction is configured to extract spatial intensity data from objects of interests having varying geometric sizes and distributed geometrically irregularly on the arrayed output image.

The arc length s, or a spiral, can be described in polar coordinates as $$(\delta s)^2 = (\delta r)^2 + r^2(\delta j)^2.$$

$$s = \frac{a\sqrt{1+b^2}}{b}(e^{b\theta} - 1)$$

Depending upon the core size, one can calculate the spiral extraction length size by solving the differential equation, which results out of the relation y'=tan(b+F):

$$y' = \frac{\tan b + \frac{y}{x}}{1 - \frac{y}{x}\tan b}$$

Substituting y=x·z and rewriting in polar coordinates gives the spiral's extraction equation.

Outward spiral traversals are accomplished by setting the segmented core centroid in center of the synthesis region to serve as a "seed" pixel. The spiral traverses from the centroid to segmented boundaries in an outward spiral using the equations described above for a logarithmic spiral.

Inward spiral transversals are accomplished by starting at the boundaries of the segmented core, traverse from the boundaries to the centroid in an inward spiral using the inverse spiral equations described above. Any point on the boundary of the segmented core can be used as "seed" pixel for the traversal. During extraction traversal, the spatial vector of pixels, in the order, in which they are traversed are copied to a linear array computer data structure. This is exemplified in the code provided in the Appendix.

The process of spiral extraction for outward radial spiral traversals includes the steps of marking the object centroid as the seed. Radially traversing outwards until all of the segment boundary pixels have been traversed and their outward neighboring pixels have also been traversed. Each traversed pixel is marked as traversed and its address is stored in a linear array along with the corresponding pixel intensity. Centroid coordinates mark the first address in the linear array data structure. This step ceases when the outward traversal is completed.

The process of spiral extraction for inward radial spiral traversal commences by marking the object centroid as a termination point. Extraction starts at any segment boundary pixel as the seed. The spiral traverses along the circumference of the object of interest in the anticlockwise or clockwise direction, until the entire object of interest is engulfed. The inward traversal can now be initiated using any segment pixel as the extraction seed. Once the extraction seed pixel is chosen, the linear array provides the pre-stored coordinates and spatial intensity corresponding to that pixel. Once the seed pixel has been found, the entire array of pixels down to the centroid, in the reverse order are stored within a newly created linear vector that will contain the extracted object of interest.

Similarly, for an outward radial spiral traversal, the centroid for the object of interest is marked as the seed pixel. The spiral radially traverses outwards until all the segment boundary pixels have been traversed and the outwardly adjacent pixels have also been traversed. Each traversed pixel is marked as traversed and its address is stored in a linear array along with the corresponding pixel intensity. The centroid coordinates mark the first address in the linear array data structure. The process ceases when the outward traversal is completed.

In most embodiments, a gradient measurement is utilized to determine how many pixels are required to adequately characterize an object of interest within the output pattern. A spatial gradient is computed in x and y directions from the core centroid. The second derivative of the spatial gradient is then computed to find hard discontinuities and boundary of the core to define the pixels associated with each core.

After the extraction of the pixels associated with an object of interest is completed, the extracted pixels are then transformed into the spectral domain to increase resolution. In some embodiments, the step of transforming the extracted pixels into the spectral domain commences with the step of computationally re-sampling the extracted pixels to increase the spatial resolution of the pixellated object. A two-dimensional surface interpolating using a set of scattered spatial data points is generated using either the method of Renka and Cline or a modification of Shepard's method.

Computational resealing provides increased spatial resolution and fine-grained morphologically for images that have limited dynamic range and/or high background noise. Computational resealing amplifies morphological artifacts thereby increasing opportunity for feature detection. This provides an opportunity for ultra-sensitive hybridization detection in genomic microarrays, when using very small amounts of starting material.

In the exemplary embodiment, an interpolating surface F(x, y) is constructed thromgh a set of m scattered data points $(x_r, y_r, f_r)$, for r=1, 2, . . . , m. Also, in the (x, y) plane, the extracted pixels, corresponding to an object of interest, must be distinct. The constructed surface is continuous and has continuous first derivatives. Synthetic resampling involves firstly creating a triangulation with all the (x, y) data points as nodes, the triangulation being as nearly equiangular as possible. Then gradients in the x- and y-directions are estimated at node r, for r=1, 2, . . . , m, as the partial derivatives of a quadratic function of x and y which interpolates the data value $f_r$, and which fits the data values at nearby nodes (those within a fixed distance provided as an input to the algorithm) in a weighted least-squares sense. The weights are chosen such that closer nodes have more influence than more distant nodes on derivative estimates at node r.

The computed partial derivatives, with the $f_r$ values, at the three nodes of each triangle define a piecewise polynomial surface of a certain form which is the interpolant on that triangle. The interpolant F(x, y) can subsequently be evaluated at n points $(x_k, y_k)$, for k=1, 2, ..., n, inside or outside the domain of the data by points outside the domain are evaluated by extrapolation.

An alternate technique that can be used for synthetic resampling is based on modification of Shepard's method. The basic Shepard method, interpolates the input data with the weighted mean. The basic method is global in that the interpolated value at any point depends on all the data. The method is made local by adjusting each $w_r(x, y)$ to be zero outside a circle with centre $(x_r, y_r)$ and some radius $R_w$. Also, to improve the performance of the basic method, each $f_r$ above is replaced by a function $f_r(x, y)$, which is a quadratic fitted by weighted least-squares to data local to $(x_r, y_r)$ and forced to interpolate $(x_r, y_r, f_r)$. In this context, a point (x, y) is defined to be local to another point if it lies within some distance $R_q$ of it. Computation of this quadratic constitutes the bulk of computational effort. If there are less than 5 other points within distance $R_q$ from $(x_r, y_r)$, the quadratic is replaced by a linear function. In cases of rank-deficiency, the minimum norm solution is computed.

The interpolant F(x, y) can subsequently be evaluated at any point (x, y) inside or outside the domain of the data. Points outside the domain are evaluated by extrapolation. Traditionally this method has been used in adapting grid size in adaptive finite element (FEM) analysis and computer graphics. Use to microarray resampling is new.

Figure 37:
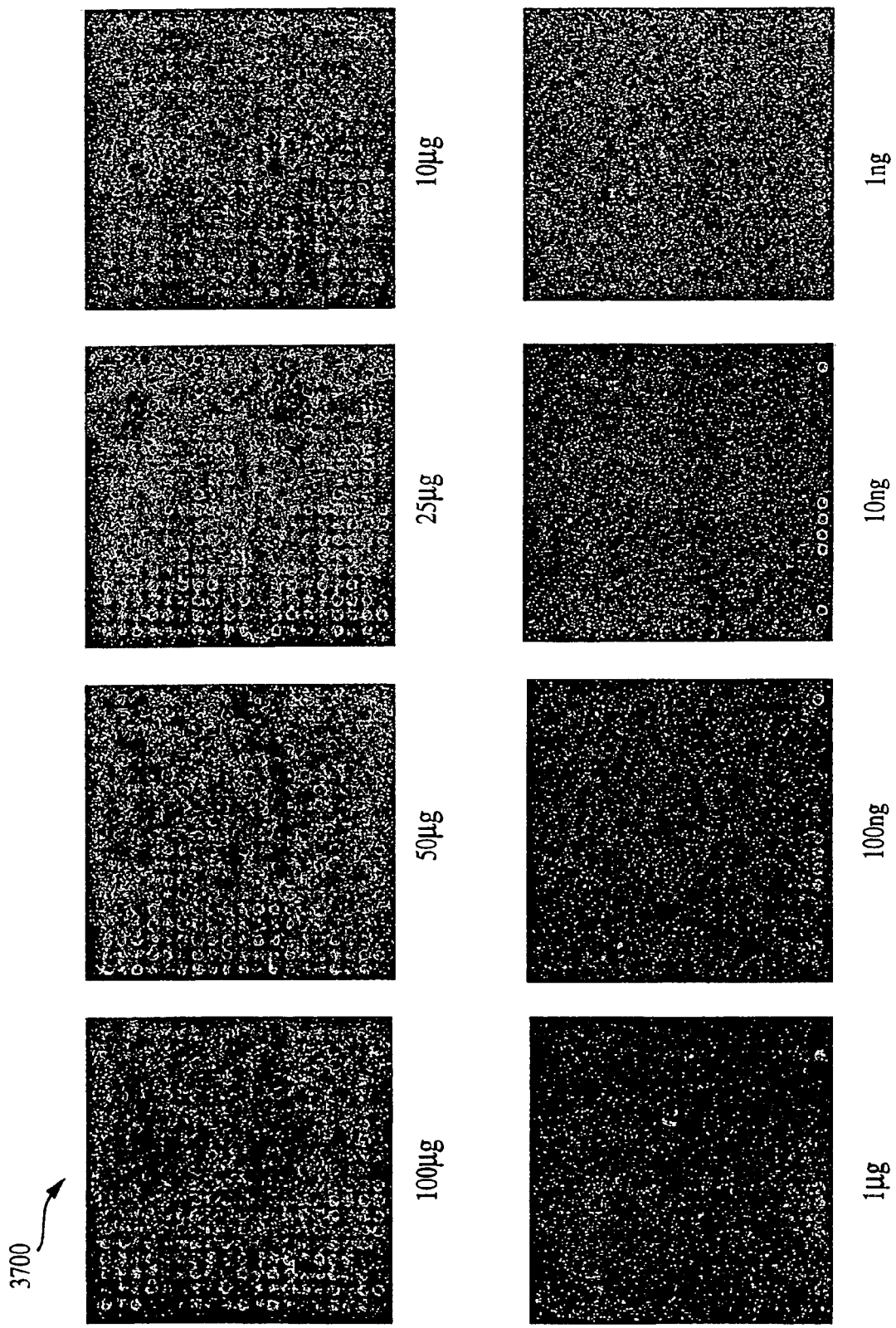
FIG. 37 illustrates signal degradation across multiple fluorescence-based output patterns of identical cDNA arrays hybridized with a serially diluted sample.
Figure 38A:
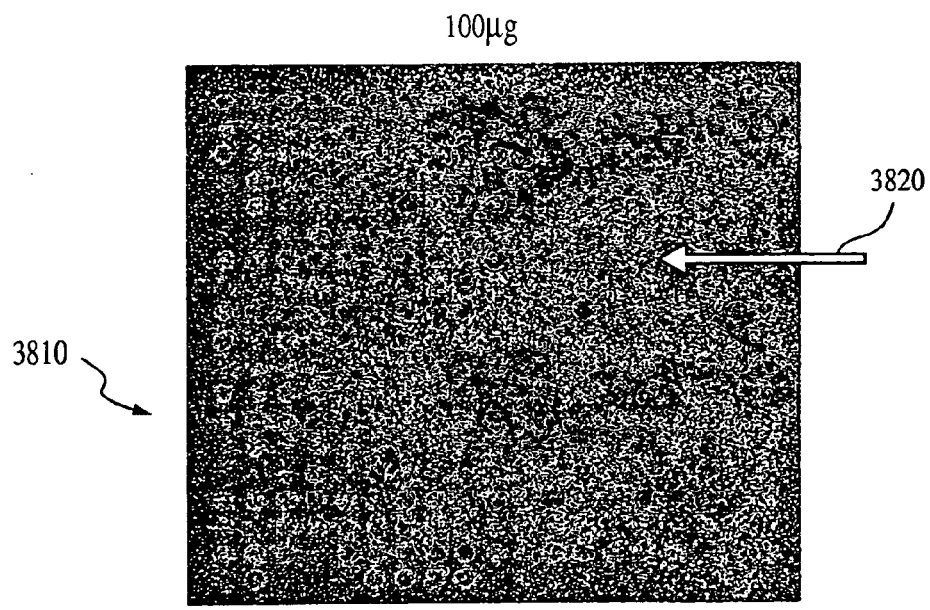
FIG. 38 illustrates an array from FIG. 37 where the sample applied to the cDNA has a concentration of 100 $\mu$g, an enlargement of an object of interest from the array, a re-sampled representation of the object of interest; and a three-dimensional intensity representation of the re-sampled object of interest.
Figure 38B:
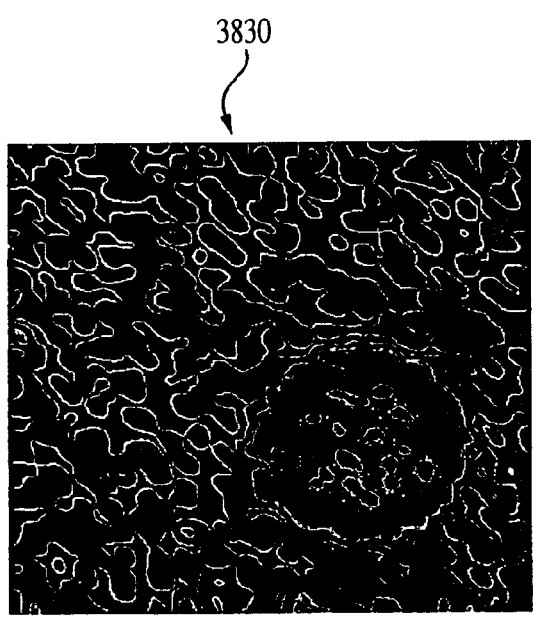
Figure 38C:
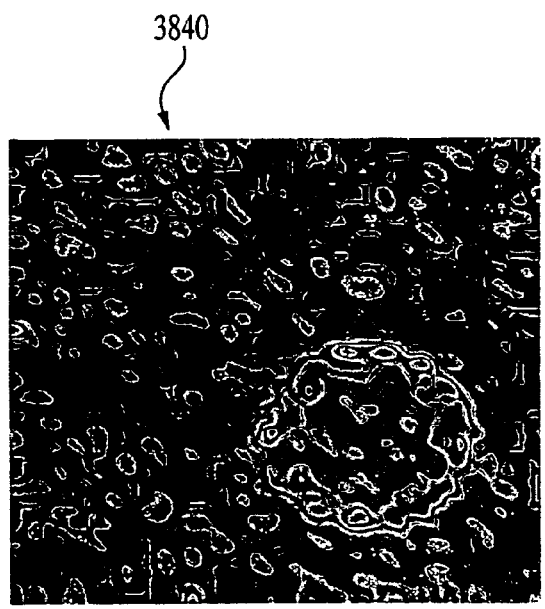
Figure 38D:
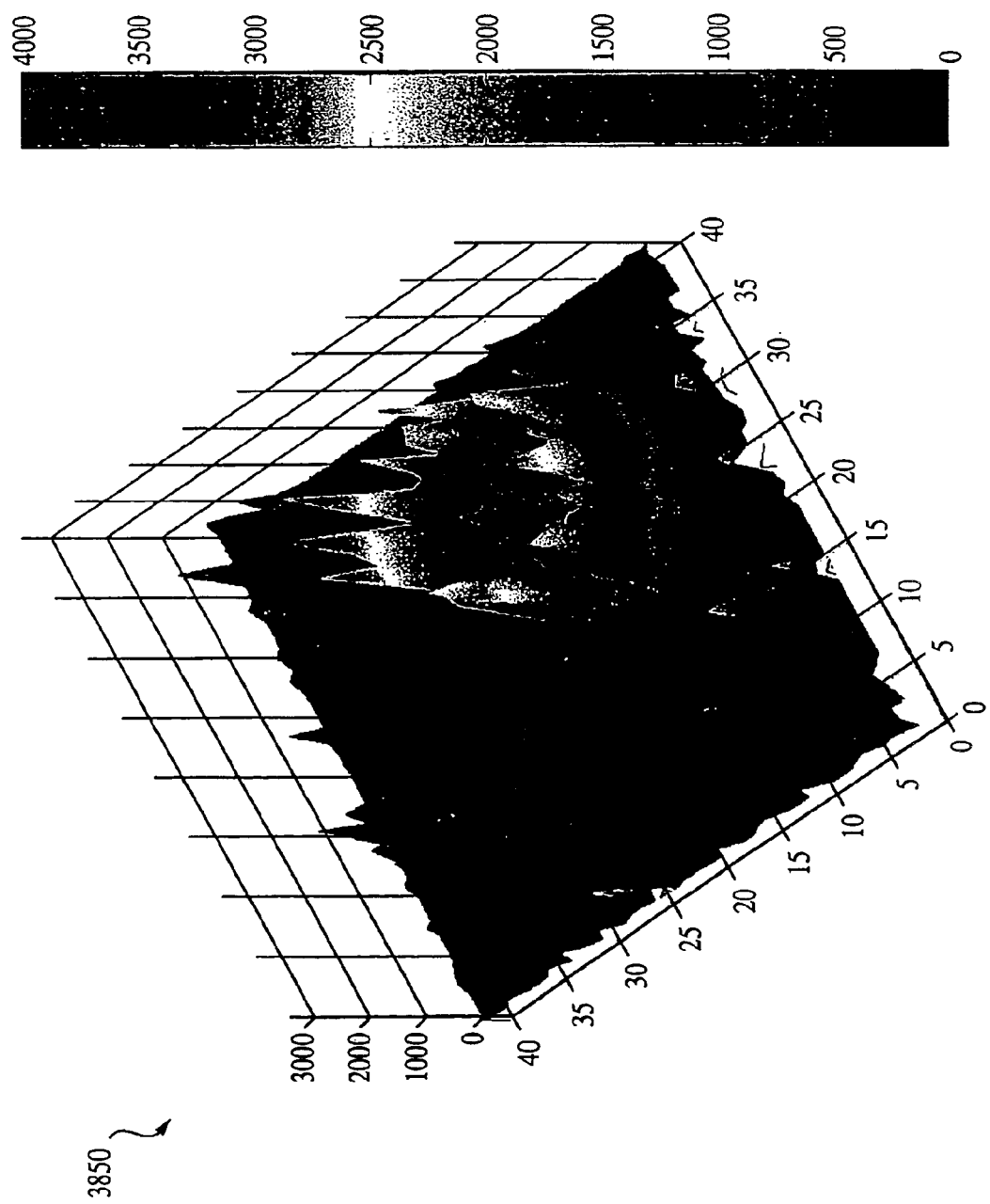
Figure 39A:
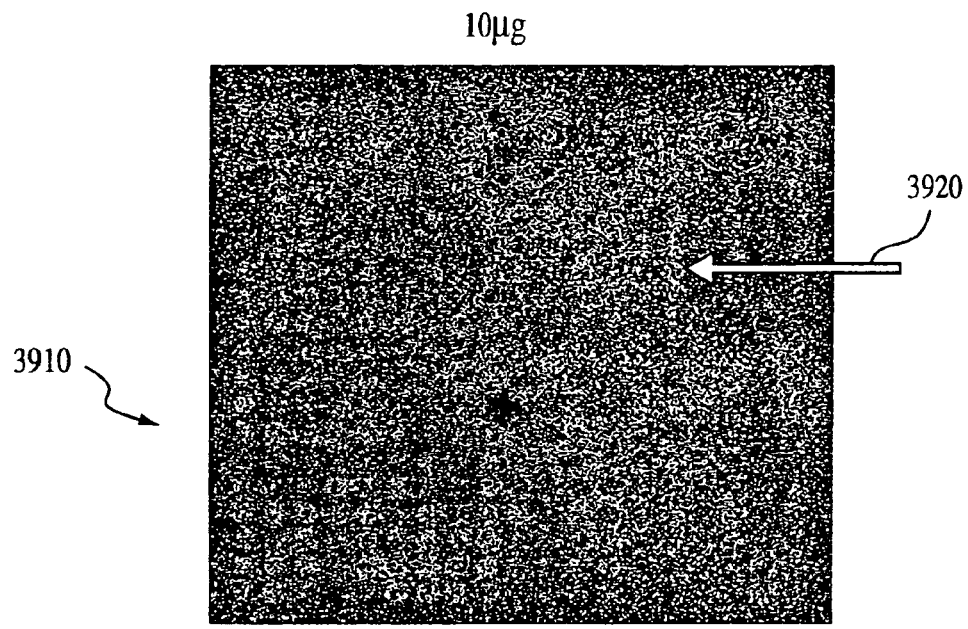
FIG. 39 illustrates an array from FIG. 37 where the sample applied to the cDNA has a concentration of 10 $\mu$g, an enlargement of an object of interest from the array, a re-sampled representation of the object of interest; and a three-dimensional intensity representation of the re-sampled object of interest.
Figures 39B, 39C:
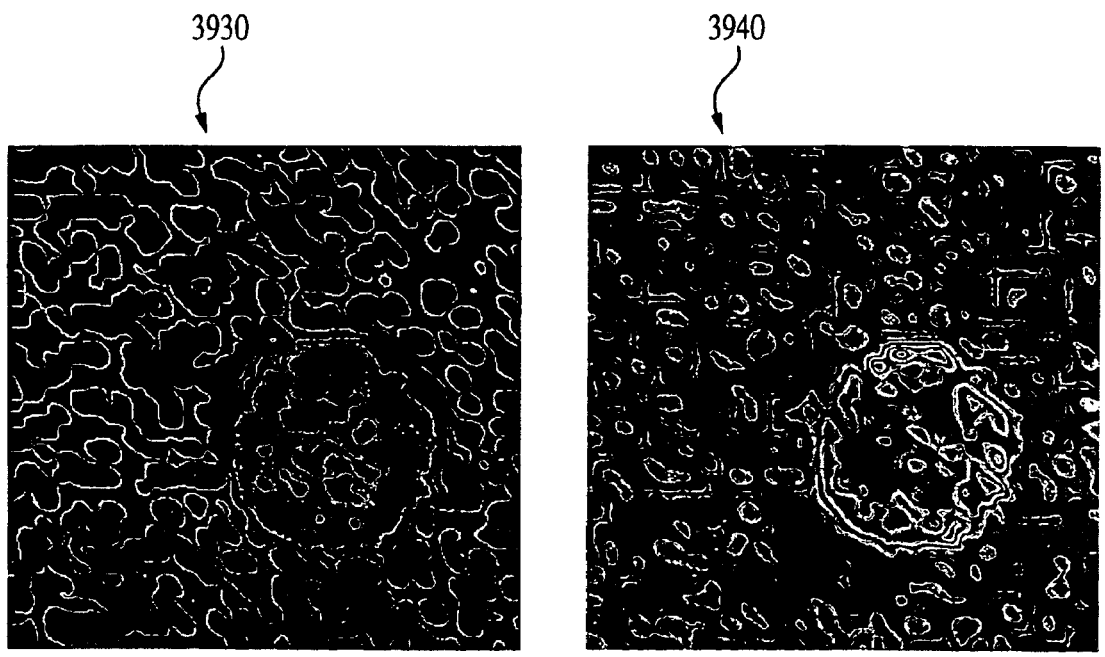
Figure 39D:
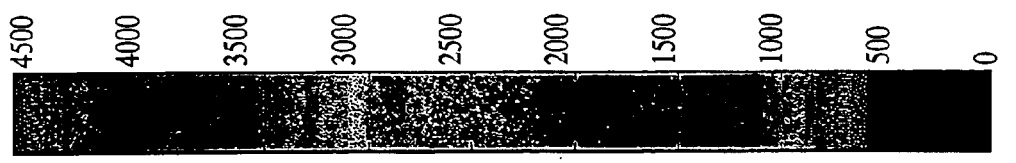
Figure 39D:
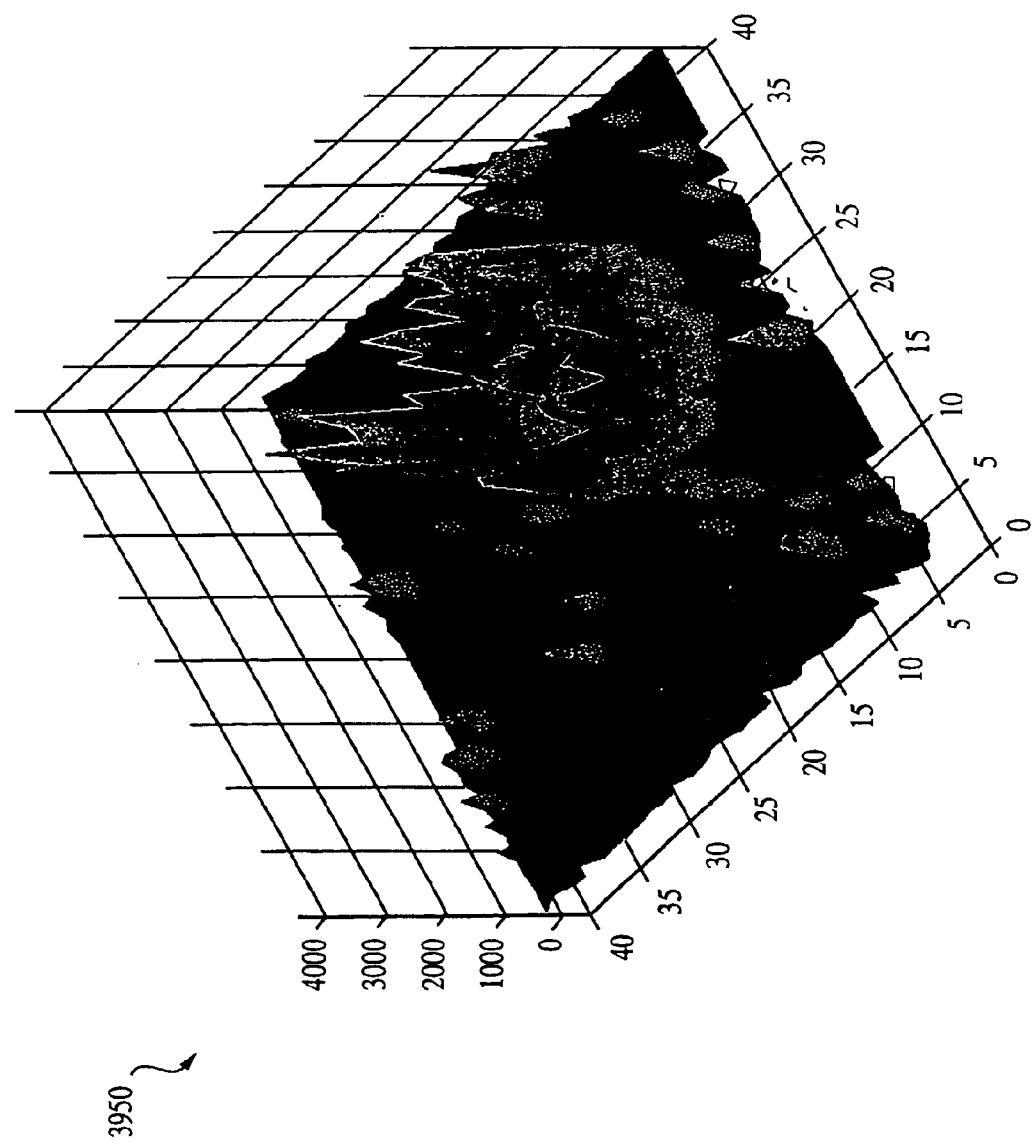
Figure 40A:
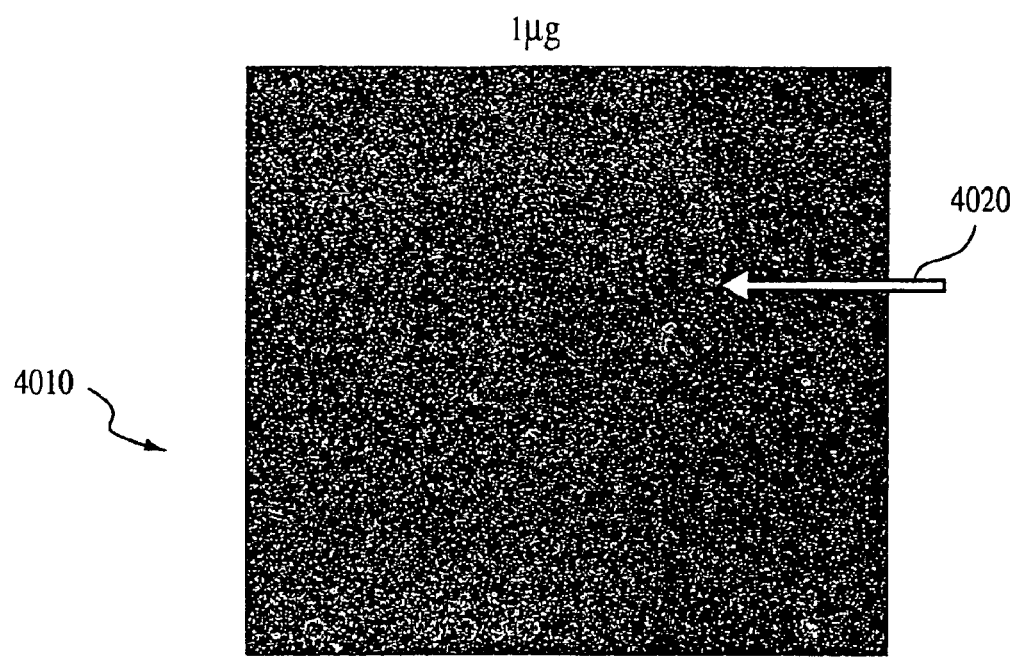
FIG. 40 illustrates an array from FIG. 37 where the sample applied to the cDNA has a concentration of 1 $\mu$g, an enlargement of an object of interest from the array, a re-sampled representation of the object of interest; and a three-dimensional intensity representation of the re-sampled object of interest.
Figure 40B:
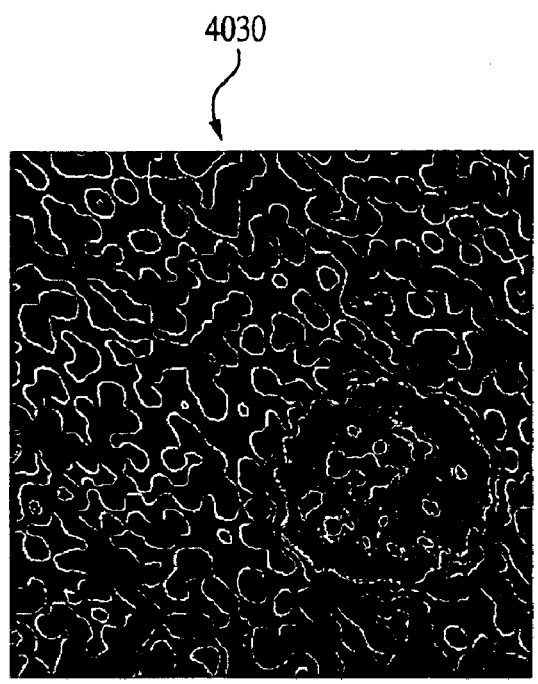
Figure 40C:
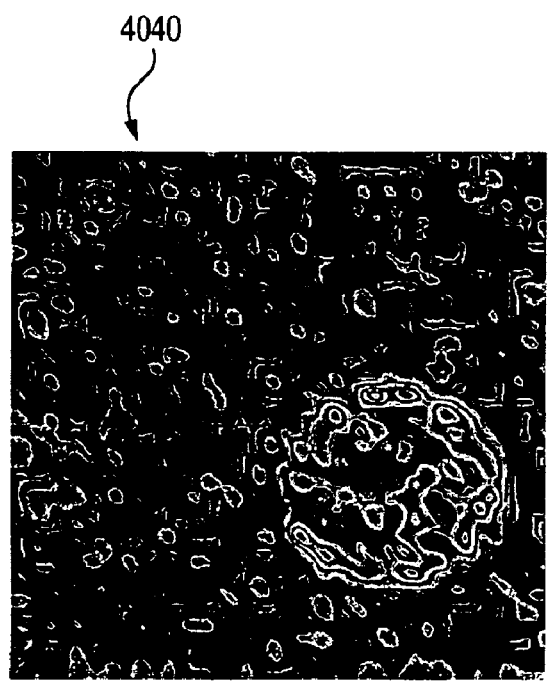
Figure 40D:
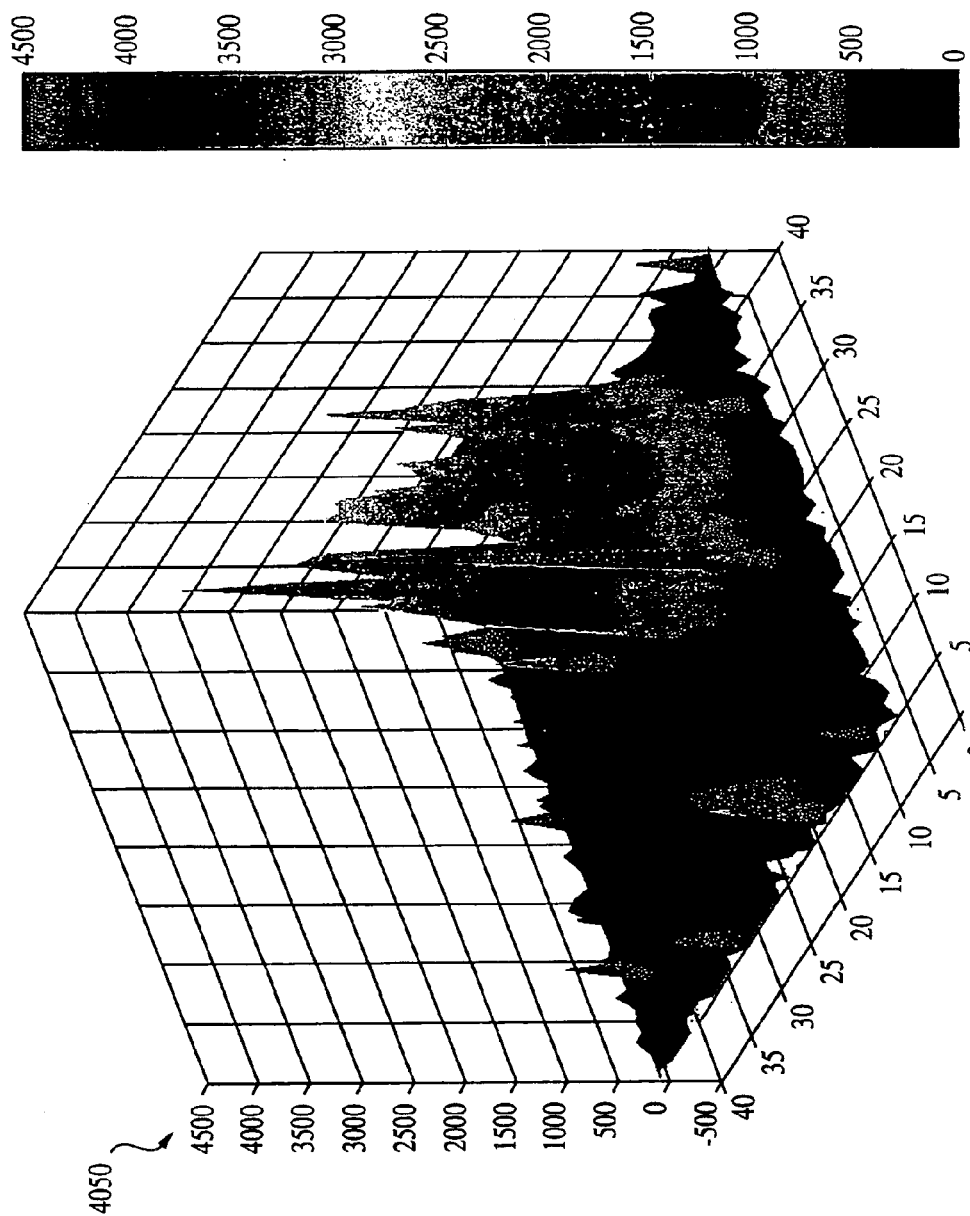
Figure 41A:
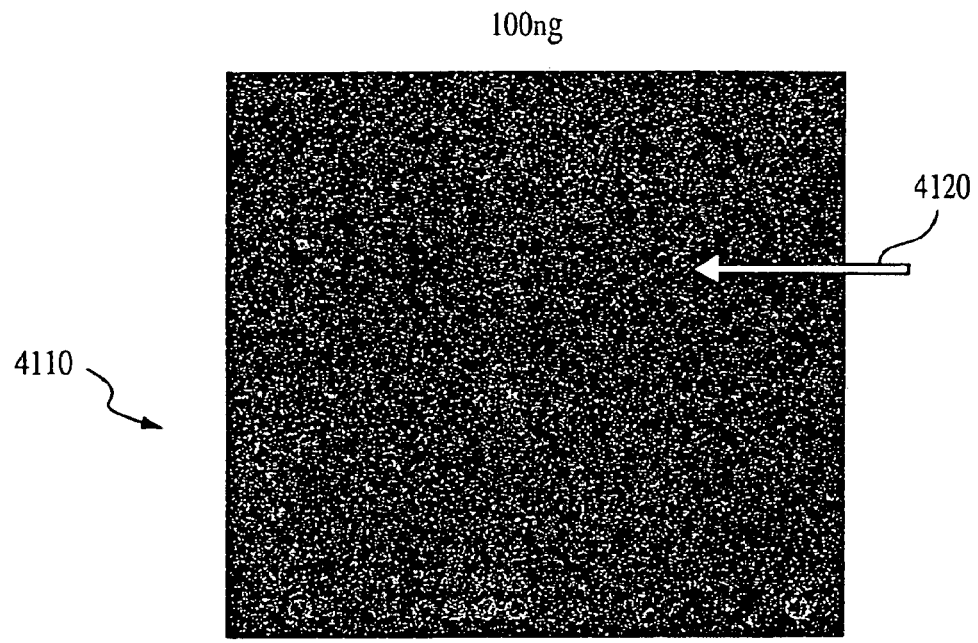
FIG. 41 illustrates an array from FIG. 37 where the sample applied to the cDNA has a concentration of 100 ng, an enlargement of an object of interest from the array, a re-sampled representation of the object of interest; and a three-dimensional intensity representation of the re-sampled object of interest.
Figure 41B:
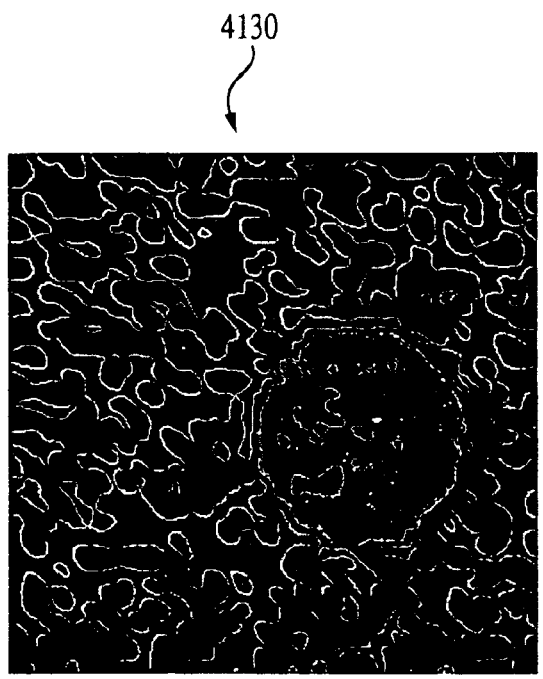
Figure 41C:
Figure 41D:
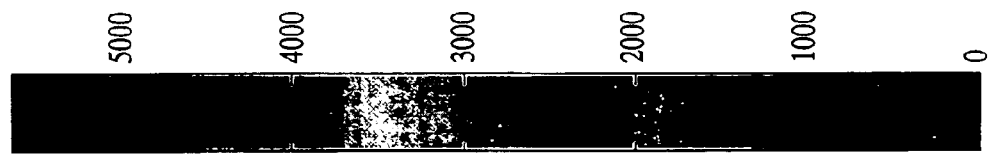
Figure 41D:
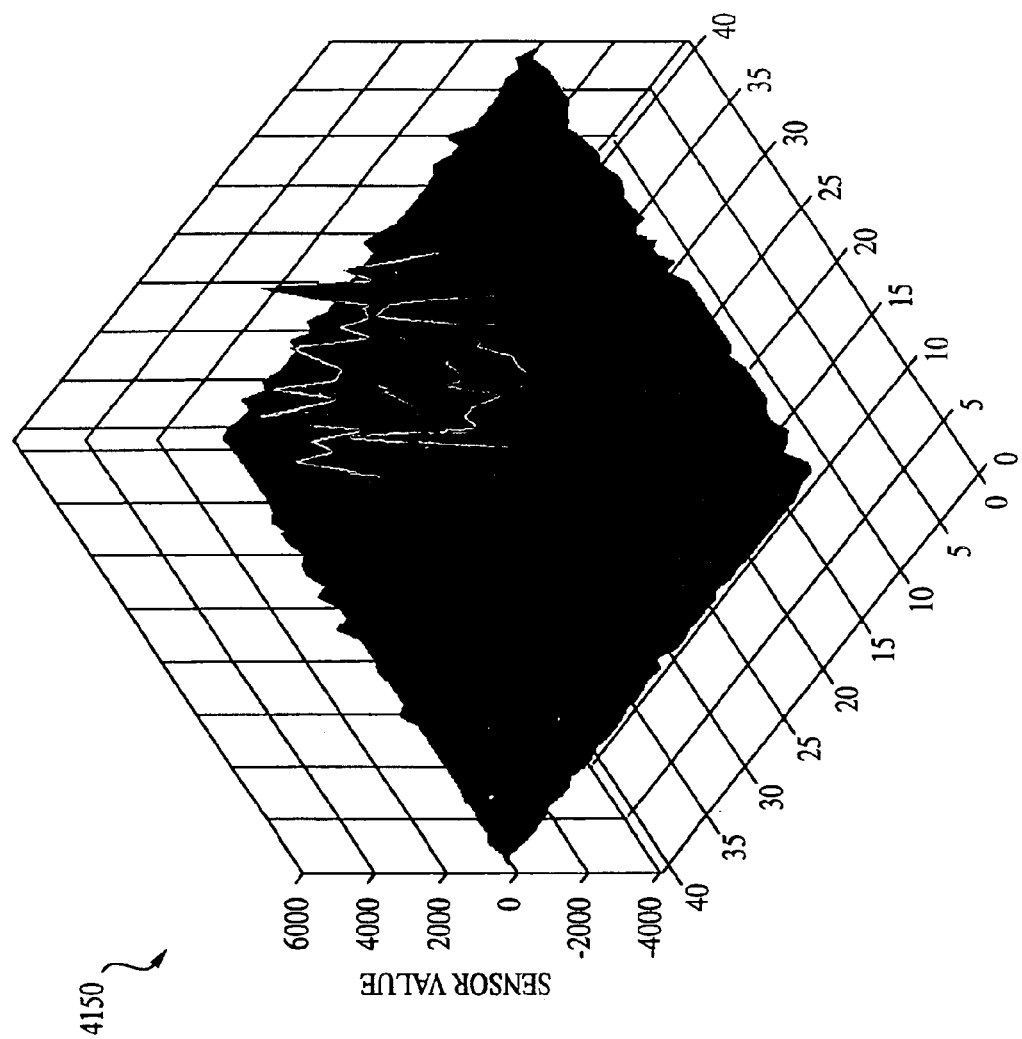
Figure 42A:
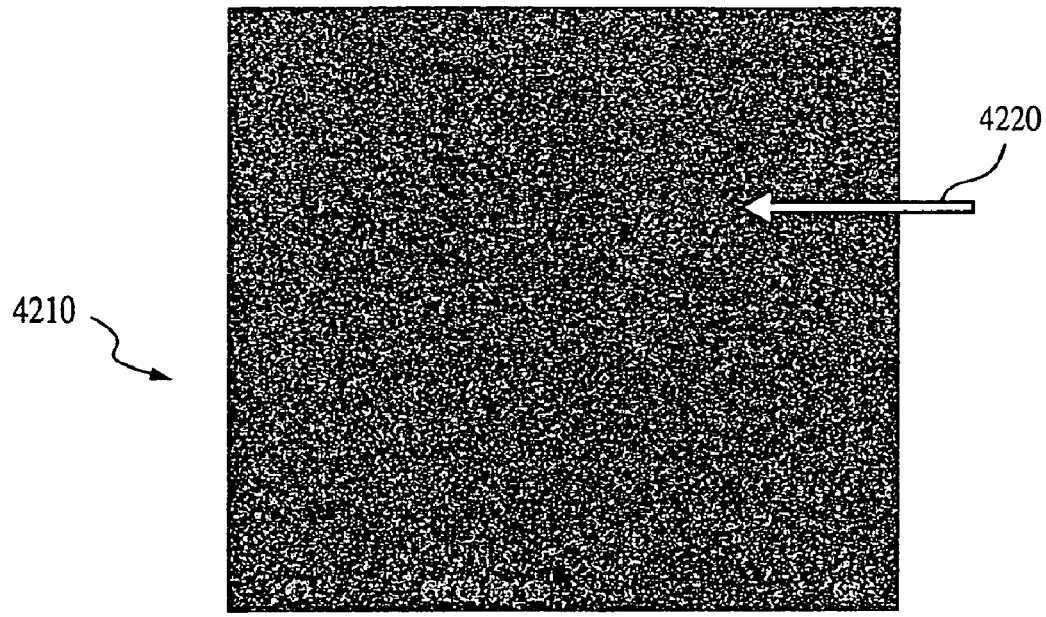
FIG. 42 illustrates an array from FIG. 37 where the sample applied to the cDNA has a concentration of 10 ng, an enlargement of an object of interest from the array, a re-sampled representation of the object of interest; and a three-dimensional intensity representation of the re-sampled object of interest.
Figure 42B:
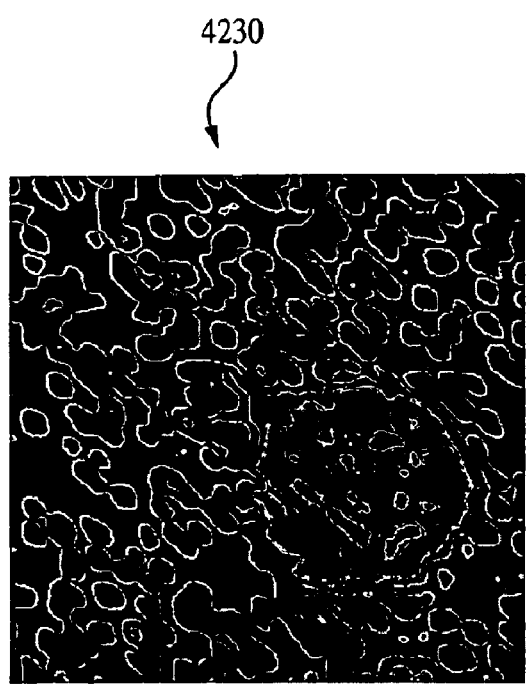
Figure 42C:
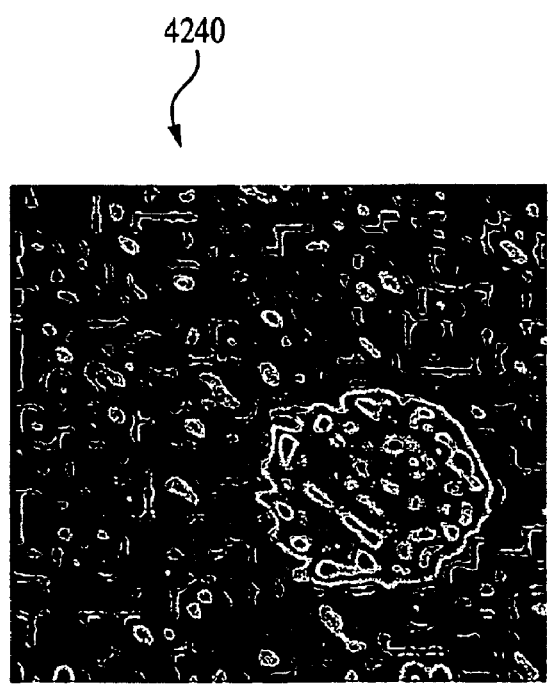
Figure 42D:
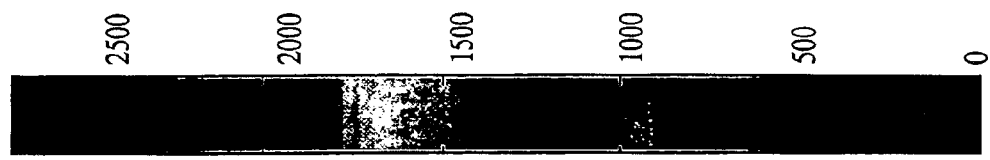
Figure 42D:
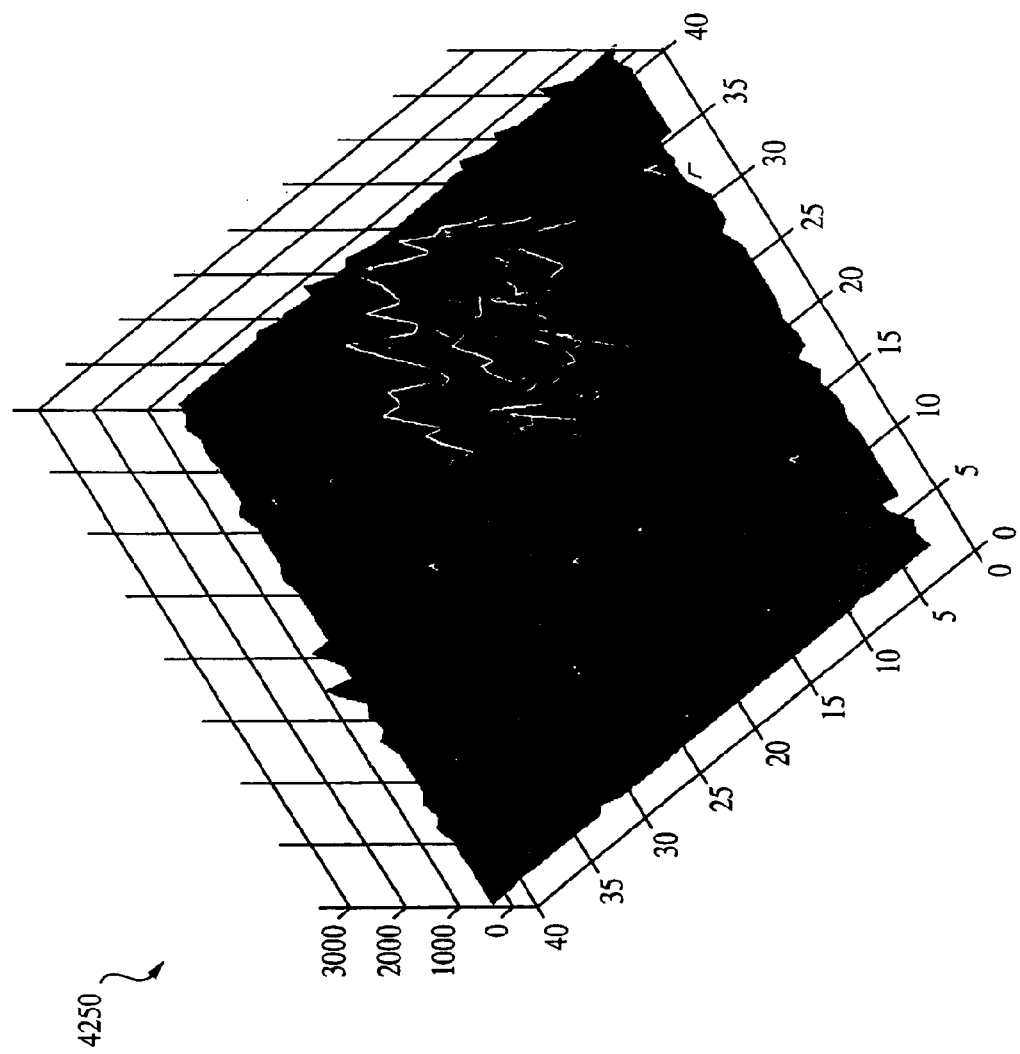
Figure 43A:
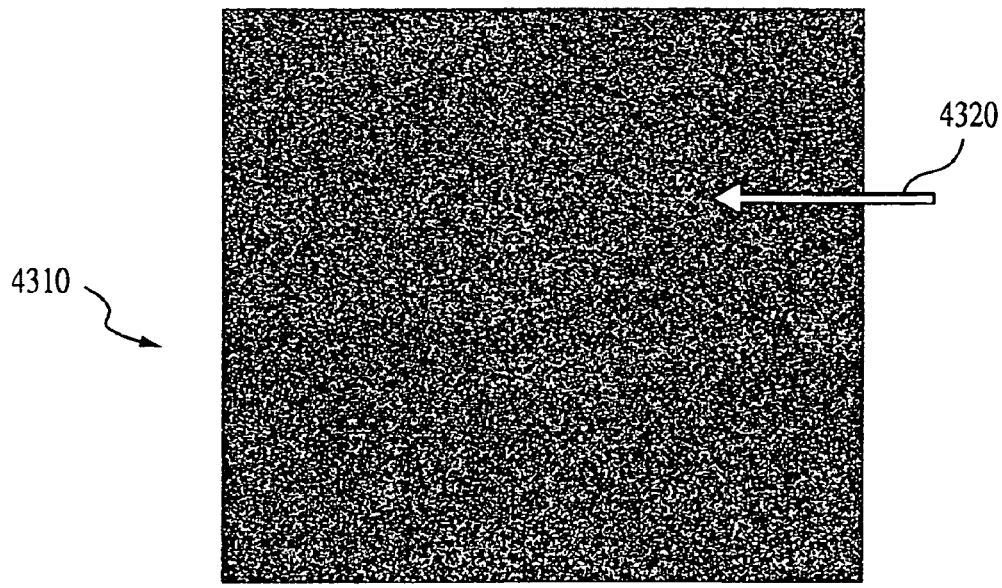
FIG. 43 illustrates an array from FIG. 37 where the sample applied to the cDNA has a concentration of 1 ng, an enlargement of an object of interest from the array, a re-sampled representation of the object of interest; and a three-dimensional intensity representation of the re-sampled object of interest.
Figure 43B:
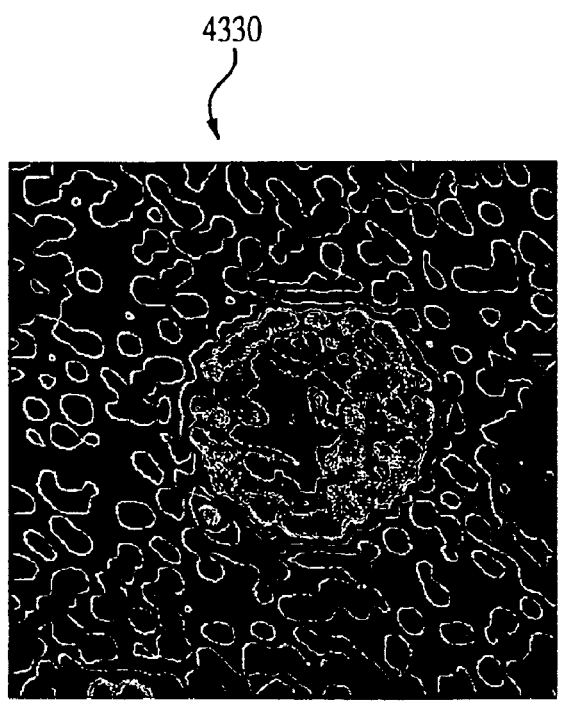
Figure 43C:
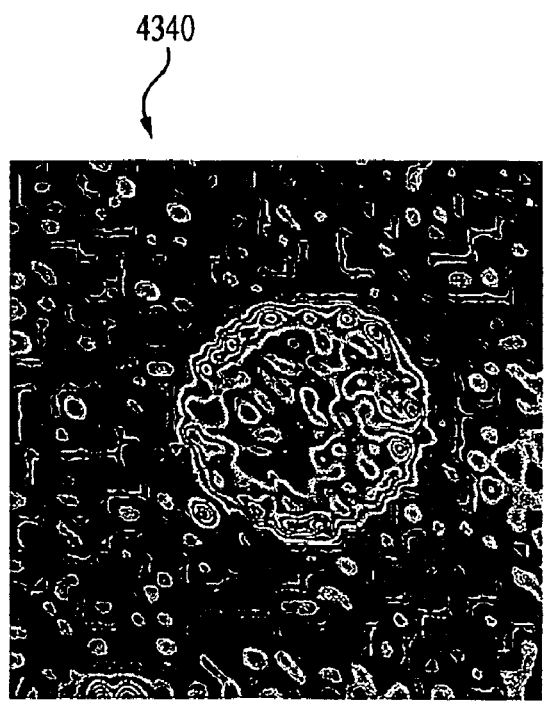
Figure 43D:
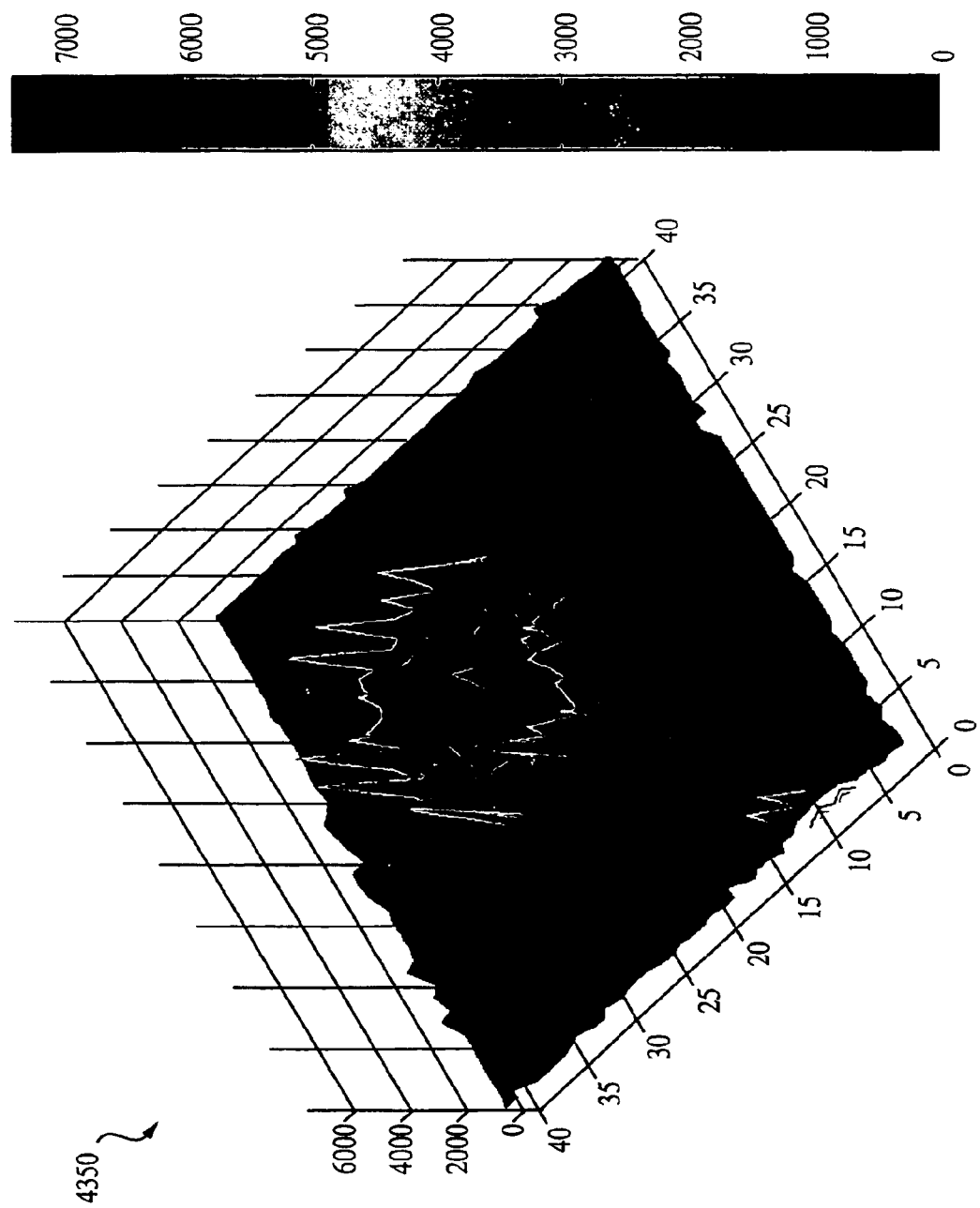

FIG. 37 illustrates an extraction of arrayed images from serial dilution series using cDNA spotted microarray hybridization experiments. The fluorescent RNA probe was total mouse testis RNA, expected to hybridize to all spots containing DNA. The exemplary Cy3 scan images represent the results of 8 hybridizations varying from 100 μg to 1 ng starting total RNA with the following concentrations: 100 μg, 50 μg, 25 μg, 10 μg, 1 μg, 100 ng, 10 ng, and 1 ng. Specifically, mouse testis RNA labeled with both Cy3 and Cy5 dyes was hybridized. The image quality is particularly low and some of the spots have merged due to a contaminant in the spotting buffer.

FIGS. 38–45 demonstrate the efficacy of synthetic re-sampling and morphology preservation on an illustrative spot based on application of Renka and Cline filter (RC) under severe image quality degradation induced by lack of labeled emitters in the diluted RNA samples.

FIG. 38 illustrates the effect of applying a 100×100 up-sample resolution RC filter on extracted spot pixels 3820 within an output pattern 3810 at 100 μg starting RNA concentration. The resolution of the extracted spot is enhanced using a contrast filter as described above 3830. The filtered extracted spot pixels are then filtered with an RC filter to provide even greater resolution which may be embodied in two or three dimensions, 3840, 3850. This transformation preserves both the spot morphology, and also systematically introduces micro-morphology artifacts and fractal artifacts that enable downstream spot characterization and elimination of false negatives and false positives.

FIG. 39 illustrates the effect of applying a 100×100 up-sample resolution RC filter on extracted spot pixels 3920 within an output pattern 3910 at 10 μg starting RNA concentration. The resolution of the extracted spot is enhanced using a contrast filter as described above 3930. The filtered extracted spot pixels are then filtered with an RC filter to provide even greater resolution which may be embodied in two or three dimensions, 3940, 3950.

FIG. 40 illustrates the effect of applying a 100×100 up-sample resolution RC filter on extracted spot pixels 4020 within an output pattern 4010 at 1 μg starting RNA concentration. The resolution of the extracted spot is enhanced using a contrast filter as described above 4030. The filtered extracted spot pixels are then filtered with an RC filter to provide even greater resolution which may be embodied in two or three dimensions, 4040, 4050.

FIG. 41 illustrates the effect of applying a 100×100 up-sample resolution RC filter on extracted spot pixels 4120 within an output pattern 4110 at 100 ng starting RNA concentration. The resolution of the extracted spot is enhanced using a contrast filter as described above 4130. The filtered extracted spot pixels are then filtered with an RC filter to provide even greater resolution which may be embodied in two or three dimensions, 4140, 4150.

FIG. 42 illustrates the effect of applying a 100×100 up-sample resolution RC filter on extracted spot pixels 4220 within an output pattern 4210 at 10 Ma starting RNA concentration. The resolution of the extracted spot is enhanced using a contrast filter as described above 4230. The filtered extracted spot pixels are then filtered with an RC filter to provide even greater resolution which may be embodied in two or three dimensions, 4240, 4250.

FIG. 43 illustrates the effect of applying a 100×100 up-sample resolution RC filter on extracted spot pixels 4320 within an output pattern 4310 at 1 ng starting RNA concentration. The resolution of the extracted spot is enhanced using a contrast filter as described above 4330. The filtered extracted spot pixels are then filtered with an RC filter to provide even greater resolution which may be embodied in two or three dimensions, 4340, 4350.

As demonstrated, computational re-sampling facilitates the preservation of feature consistency over a four log dilution range down to 1 ng concentration level.

The next step transforms the extracted core pixels into the spectral domain, using the Fast Fourier Transform (FFT). In general the FFT provides the means of transforming a signal defined in the time domain into one defined in the frequency domain. Core extraction leads to a spatial signal vector of length N. The transformed spectra are also of length N. A length N sequence x can be denoted by x(n), n=0,1,2, ... N−1 where x(n) may be real ($x \in R^N$) or complex ($x \in C^N$). This is achieved as follows. Consider the core x as a vector $\underline{x}$ in an N dimensional vector space. That is, each extraction core x(n) is regarded as a coordinate in that space. Also this spatial vector, denoted as $\underline{x}$ is mathematically a single point in N-space represented by a list of coordinates ($x_0, x_z, x_2, ..., x_{N-1}$). It can be interpreted geometrically as an arrow in N-space from the origin $\underline{0} \triangleq (0,0,...,0)$ to the point $\underline{x} \triangleq (x_0, x_1, x_2, ..., x_{N-1})$.

We define the following as equivalent:

$$x \triangleq \underline{x} \triangleq x(\cdot) \triangleq (x_0, x_1, \ldots, x_{N-1}) \triangleq [x_0, x_1, \ldots, x_{N-1}] \triangleq [x_0, x_1, \ldots, x_{N-1}]$$

where $x_n \triangleq x(n)$ is the nth sample of the spatial core extraction x.

For purposes of exemplary embodiment consider all extraction vectors to be of length N.

The current invention utilizes zero padding for extraction cores with less than N components (say for small spots).

Zero padding consists of appending zeros to a signal. It maps a length N signal to a length M>N signal, but M need not be an integer multiple of N:

$$ZEROPAD_{M,m}(x) \triangleq \begin{cases} x(m), & 0 \leq m \leq N-1 \\ 0, & N \leq m \leq M-1 \end{cases}$$

For example, $$\text{ZEROPAD}_{10}([1,2,3,4,5]) = [1,2,3,4,5,0,0,0,0,0]$$

The above definition is natural when x(n) represents a signal starting at time 0 and extending for N samples. In general, consider a complex series x(k) with N samples of the form $$x_0, x_2, x_3 \ldots x_k \ldots x_{N-1}$$

where x is a complex number $$X_i = X_{real} + J X_{imaq}$$

Further, assume that that the series outside the range 0, N−1 is extended N-periodic, that is, $X_k = X_{k+N}$ for all k. The FFT of this series will be denoted X(k), it will also have N samples. The forward transform will be defined as $$x(n) = \frac{1}{N} \sum_{k=0}^{N-1} x(k) e^{-jk2\pi n/N} \text{ for } n = 0 \ldots N-1$$

The Discrete Fourier Transform (DFT) of a signal x may be defined by:

$$X_p(w_k) \triangleq \sum_{n=0}^{N-1} x_p(t_n) e^{-j w_k t_n}, k = 0,1,2,\ldots, N-1$$

where
$\triangleq$ means "is defined as" or "equals by definition"

$$\sum_{n=0}^{N-1} f(n) \triangleq f(0) + f(1) + \ldots + f(N-1)$$

$x_p(t_n) \triangleq$ input signal amplitude (real or complex) at time $t_n$ (sec)
$t_n \triangleq$ nT=nth sampling instant (sec)
n $\triangleq$ sample number (integer)
T $\triangleq$ sampling period (sec)
$X_p(\omega_k) \triangleq$ Spectrum of $x_p$ (complex amplitude), at radian frequency $\omega_k$ (rad/sec)
$\omega_k \triangleq$ kΩ=kth frequency sample (rad,/sec)

$$\Omega \triangleq \frac{2\pi}{NT} = \text{radian-frequency sampling interval}(\text{rad/sec})$$

$f_S \triangleq$ 1/T=sampling rate (samples/sec, or Hertz (Hz))
N=number of samples in both time and frequency (integer)
DFT can be rewritten $$X(k) \triangleq \frac{1}{N} \sum_{n=0}^{N-1} x(n) e^{-j2\pi nk/N}, k = 0,1,2,\ldots, N-1$$

-continued $$x(n) = \frac{1}{N} \sum_{k=0}^{N-1} X(k) e^{j2\pi nk/N}, \quad n = 0,1,2,\ldots, N-1$$

where x(n) denotes the input signal at time (sample) n, and X(k) denotes the kth spectral sample.

This general definition above for a complex series can be also defined for a real valued series. A real valued series can be represented by setting the imaginary part to 0. In general, the transform into the frequency domain will be a complex valued function, that is, with magnitude and phase.

$$\text{magnitude} = \|x(n)\| = (x_{real} * x_{real} + x_{imag} * x_{imag})^{0.5}$$

$$\text{phase} = \tan^{-1}\left(\frac{x_{imag}}{x_{real}}\right)$$

The above equations are used for transforming a spatial core to a spectral core.

The spectral core is further converted to a power series representation using the Welch's method. Welch's method (or the periodogram method) for estimating power spectral density is carried out by dividing the time signal into successive blocks, and averaging squared-magnitude DFTs of the signal blocks. Let denote the $x_m$ denote the mth block of the signal x, and let M denote the number of blocks. Then the PSD estimate is given by $$\hat{R}_x(k) = \frac{1}{M} \sum_{m=0}^{M-1} |DFT_k(x_m)|^2 \triangleq \{|X_m(w_k)^2|\}_m$$

The power spectral density representation $R_x(k)$ is used for characterizing and analyzing the extraction core.

In some embodiments, the current invention also utilizes the step of convolving the extracted pixels with discretized coefficients of a function (linear functions, non-linear functions, canonical kernel functions.) In general, the following relationships hold:

The Fourier transform is linear, that is a f(t)+b g(t)→a F(f)+b G(f)

a $x_k$+b $y_k$→a $X_k$+b $Y_k$

Scaling relationship f(t/a)→a F(a f)

f(at)→F(f/a)/a

Shifting f(t+a)→F(f) $e^{-j\, 2\, pi\, a\, f}$

Modulation f(t) $e^{j2\, pi\, a\, t}$→F(t−a)

Also, the convolution operation between two spectra x and y in $C^N$ is denoted "x*y" and defined by $$(x * y)_n \triangleq \sum_{m=0}^{N-1} x(m) y(n-m)$$

The basic concept is that a window of some finite size and shape is scanned across the spectrally transformed vector. The window with its weights is called the convolution kernel. If the filter h[j,k] is zero outside the (rectangular) window {j=0,1, . . . ,J−1; k=0,1, . . . ,K−1}, then the convolution can be written as the following finite sum:

$$c[m,n] = a[m,n] \otimes h(m,n) = \sum_{j=0}^{J-1} \sum_{k=0}^{K-1} h[j,k]a[m-j,n-k]$$

The general steps for convolving the spectral core with a convolution kernel are given by:
  (a) Compute $A(\Omega,\Psi)=F\{a[m,n]\}$
  (b) Multiply $A(\Omega,\Psi)$ by the precomputed $(\Omega,\Psi)=F\{h[m,n]\}$
  (c) Compute the result $c[m,n]=F^{-1}\{A(\Omega,\Psi)*(\Omega,\Psi)\}$
where f, g, and h are arbitrary functions and a is a constant. Convolution satisfies the properties $$f*g=q*f$$

$$f*(g*h)=(f*q)*h$$

$$f*(g+h)=(f*g)+(f*h)$$

The property, f*(g*h), of successive convolutions is also denoted as a convolution cascade. In general, it can be extended to k convolutions, f*(g*(h*(i* . . . (*k))) . . . ))) The above relationships are used to increase the spatial resolution by convolution of the spectrally transformed pixels within extraction core.

Figure 44:
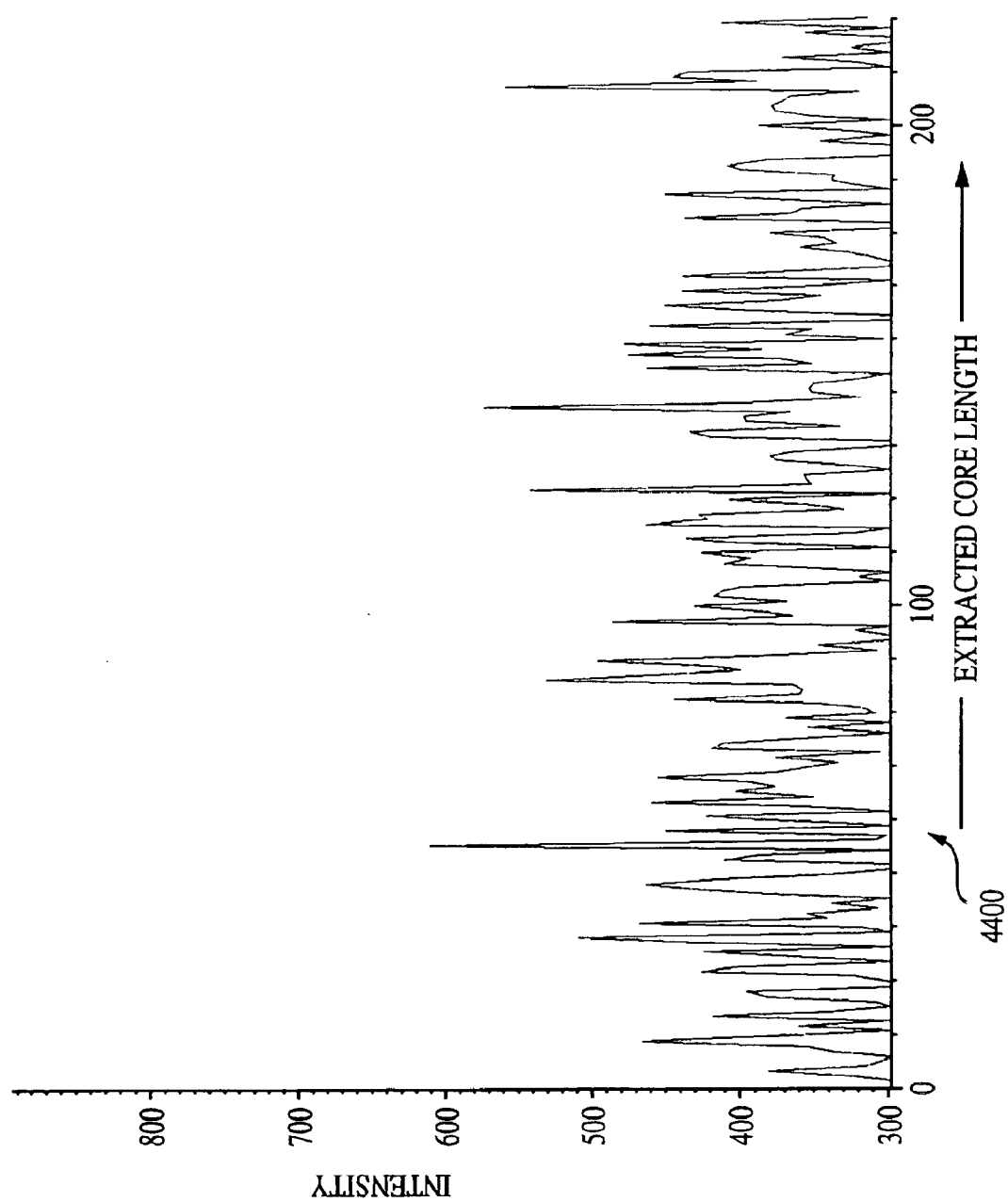
FIG. 44 illustrates an exemplary intensity distribution of extracted core pixels.

With reference to FIG. 44, a one dimensional plot 4400 of the spatial intensities of the pixels in the spirally extracted core of an object of interest is illustrated. The plotted one dimensional vector length corresponds to the length of the spiral traversal starting at the spot centroid. This plot is constructed by directly capturing the spot pixel values copied to the extraction data structure.

Figure 45:
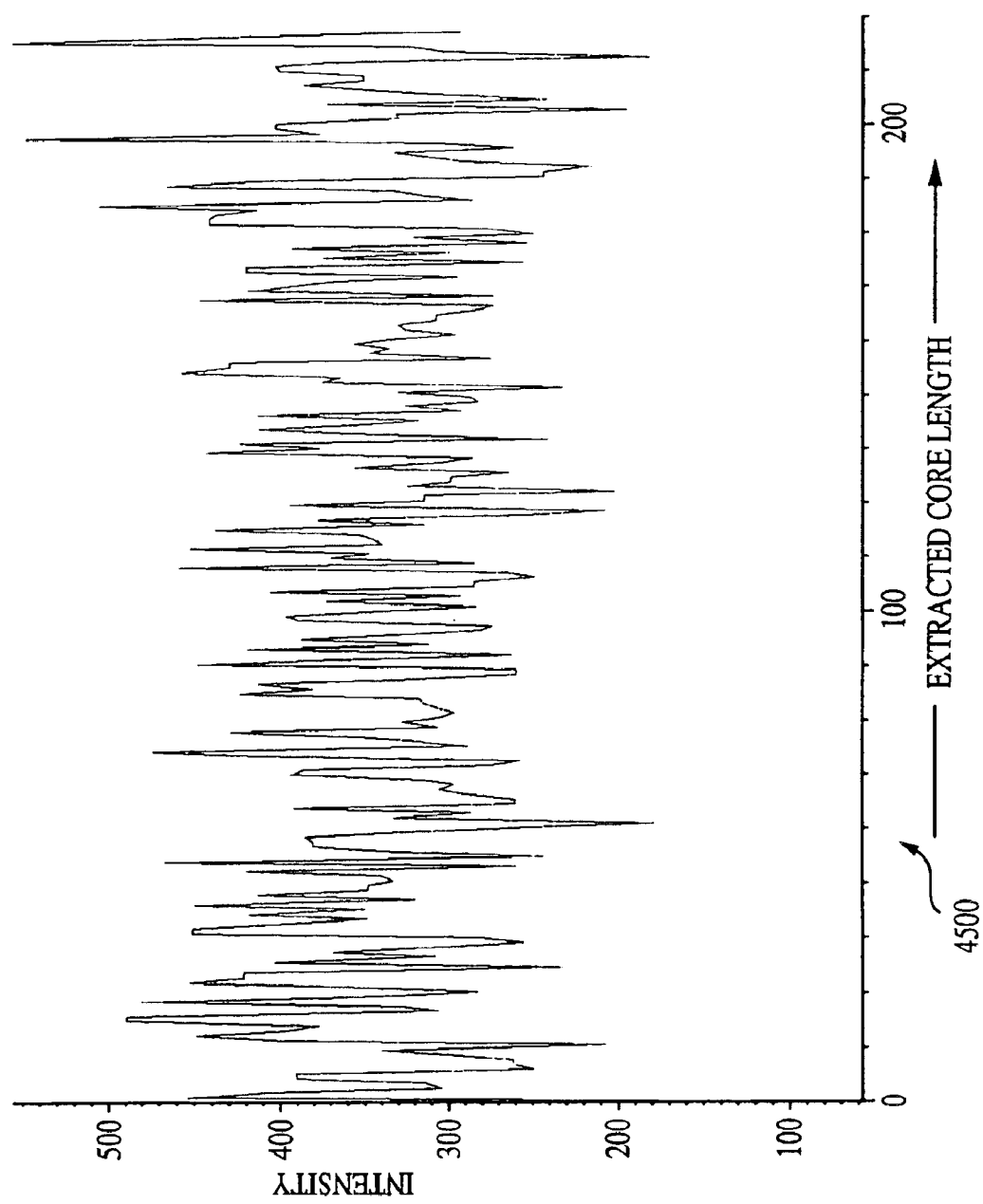
FIG. 45 illustrates an exemplary intensity distribution of pixels within the output pattern that are not associated with an object of interest.

FIG. 45 illustrates a one dimensional plot 4500 of the spatial intensities of the pixels that are not in the spirally extracted core from a segmented object of interest, but instead correspond to the background. The plotted one dimensional vector length corresponds to an arbitrary chosen background section. The plot is constructed either by continuing the spiral extraction for some j-progression points once the object segmentation boundary has been reached, or by starting the radial inward spiral extraction some j-points outside the object segmentation.

Figure 46:
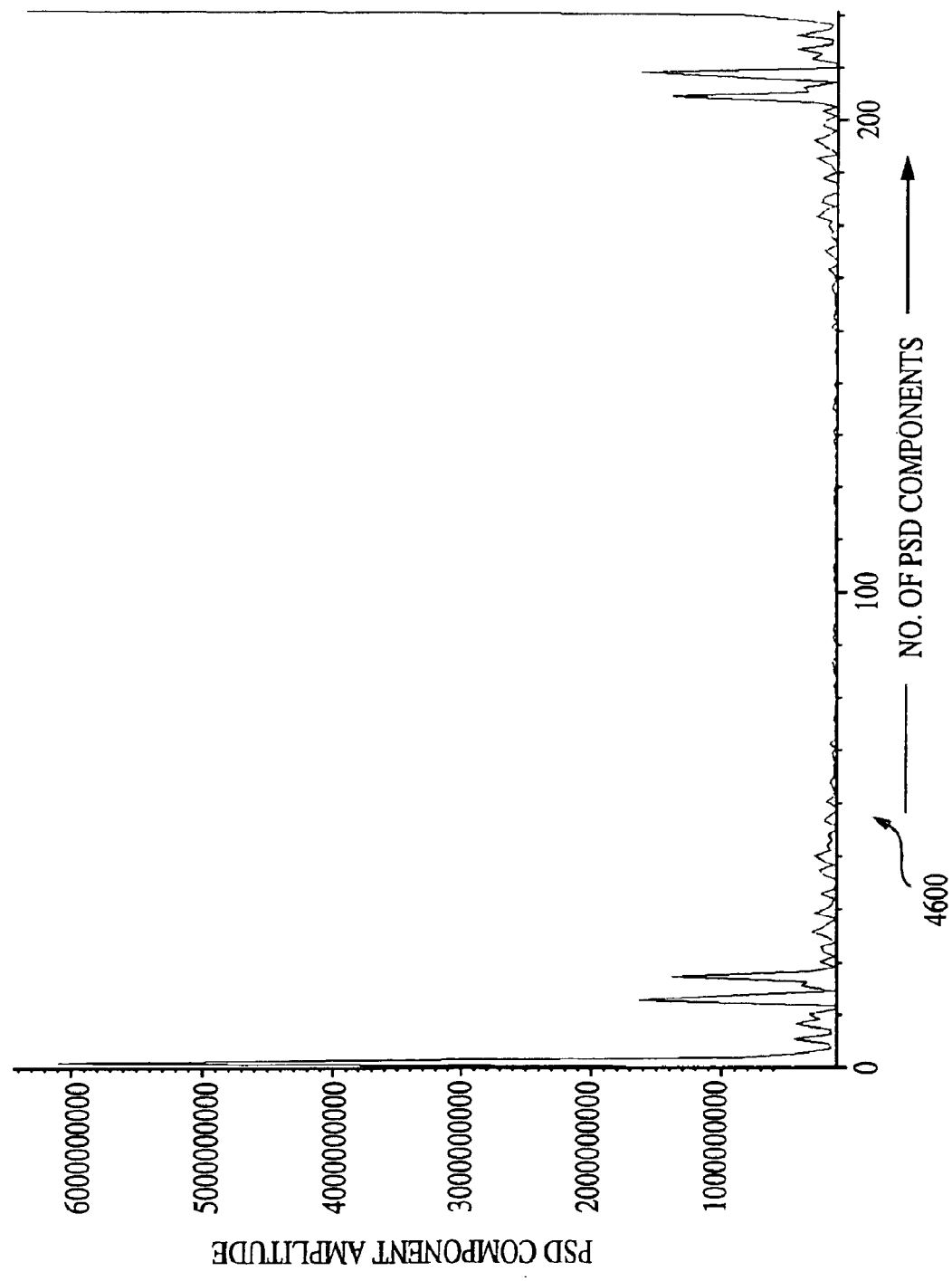
FIG. 46 illustrates an exemplary power spectral density representation of extracted core pixels and adjacent pixels not associated with an object of interest.

FIG. 46 illustrates the power spectral density computing by spectrally transforming the spirally extracted core intensities in 4400 using FFT and then computing the power distribution. For reference, the bipolar harmonic clusters in the PSD correspond to the pixels associated with an object of interest and its background. For a one dimensional FFT or DFT spectral transformation, the number of PSD harmonics corresponds to the length of total spiral extraction, which may or may not include the background pixels.

Figure 3:
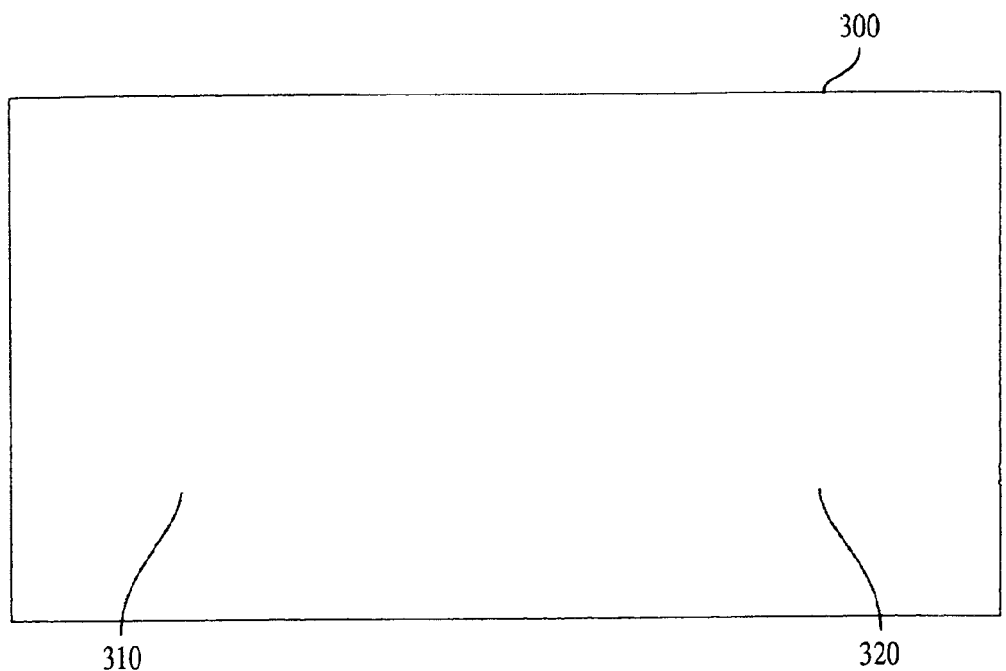
FIG. 3 illustrates a section of an output pattern featuring two objects of interest.
Figure 47:
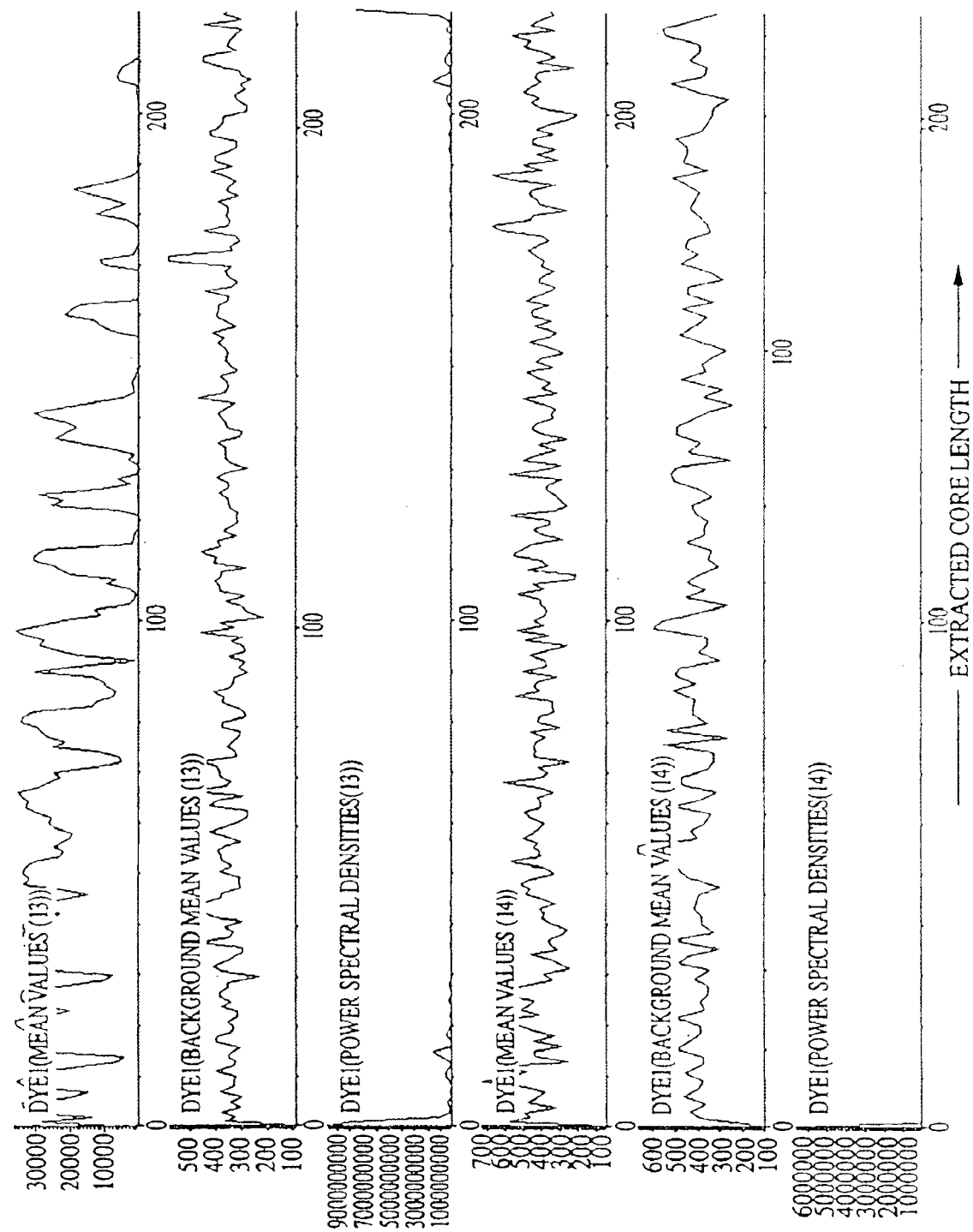
FIG. 47 illustrates the extracted core, pixels not associated with the object of interest, and the power spectral density for the objects of interest shown in FIG. 3.

FIG. 47 illustrates a one dimensional plot for spatial pixel intensities corresponding to the two objects of interest shown in FIG. 3, their background pixel intensities and the PSD for the spirally extracted and transformed core. Both the spots were extracted to the same core length in 4700.

Figure 48:
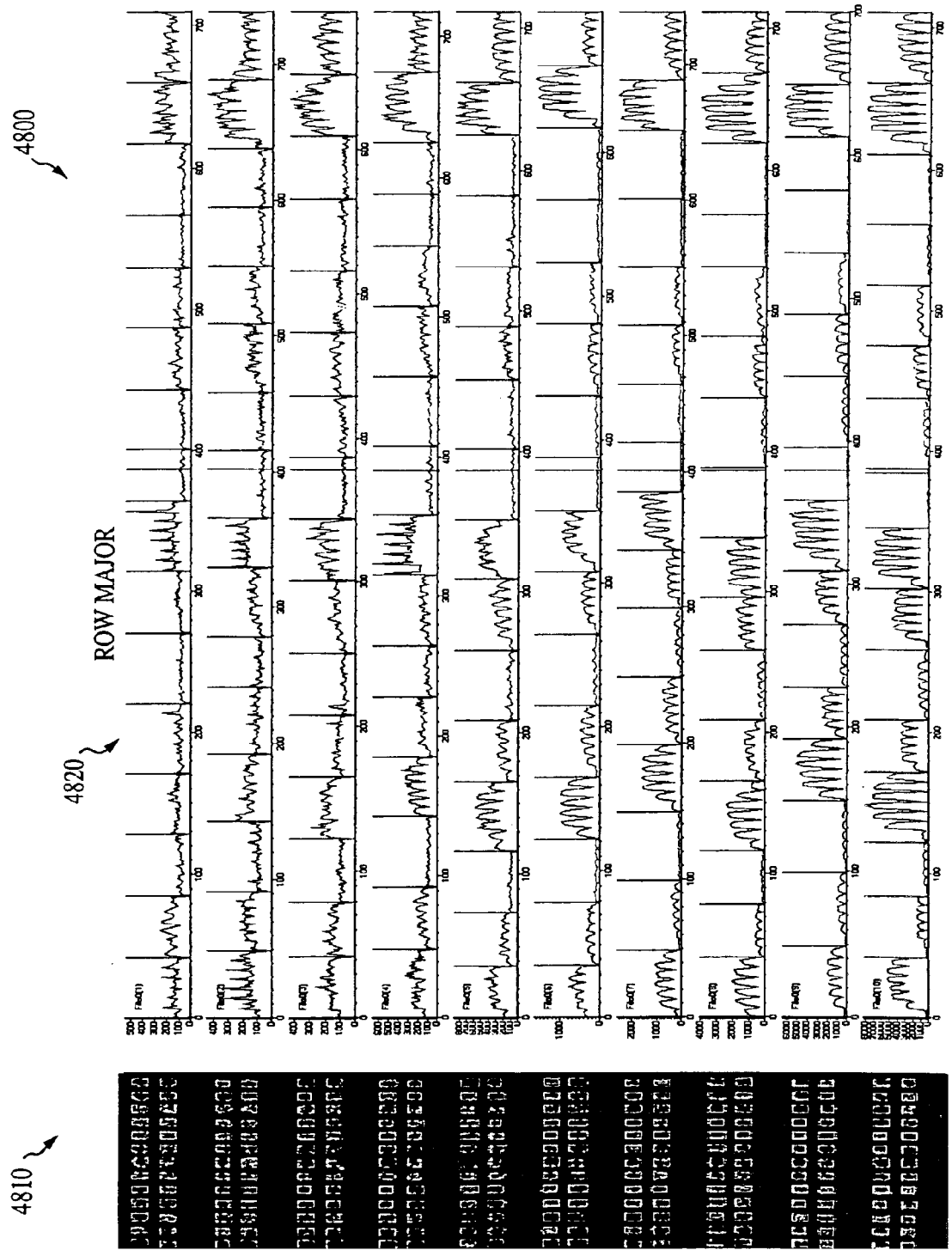
FIG. 48 illustrates a row major extraction of pixels relating to the hybridization of a single serially diluted gene, represented by multiple objects of interest, using a synthesized oligonucleotide microarray.

FIG. 48 illustrates the results of a rectilinear extraction for a gene that is represented by multiple probes or features and includes a computationally constructed pixellated panel of the same gene obtained by deconstructing the features constructing to the gene from several microarray experiments using a synthesized oligonucleotide microarray platform 4810. The experiments present expressions levels for the gene under varying serial dilutions. Each gene is individually represented by 32 features. The panel 4820 shows the spatial distribution of intensities in the extracting core using 16 of the features. Individual features are regular in character and extracted using rectilinear extracted by scanning along the rows in x-direction. The panel is then spectrally transformed to PSD vectors for further analysis. Both one dimensional and two dimensional DFT provide comparable results in spectral regime.

Figure 49:
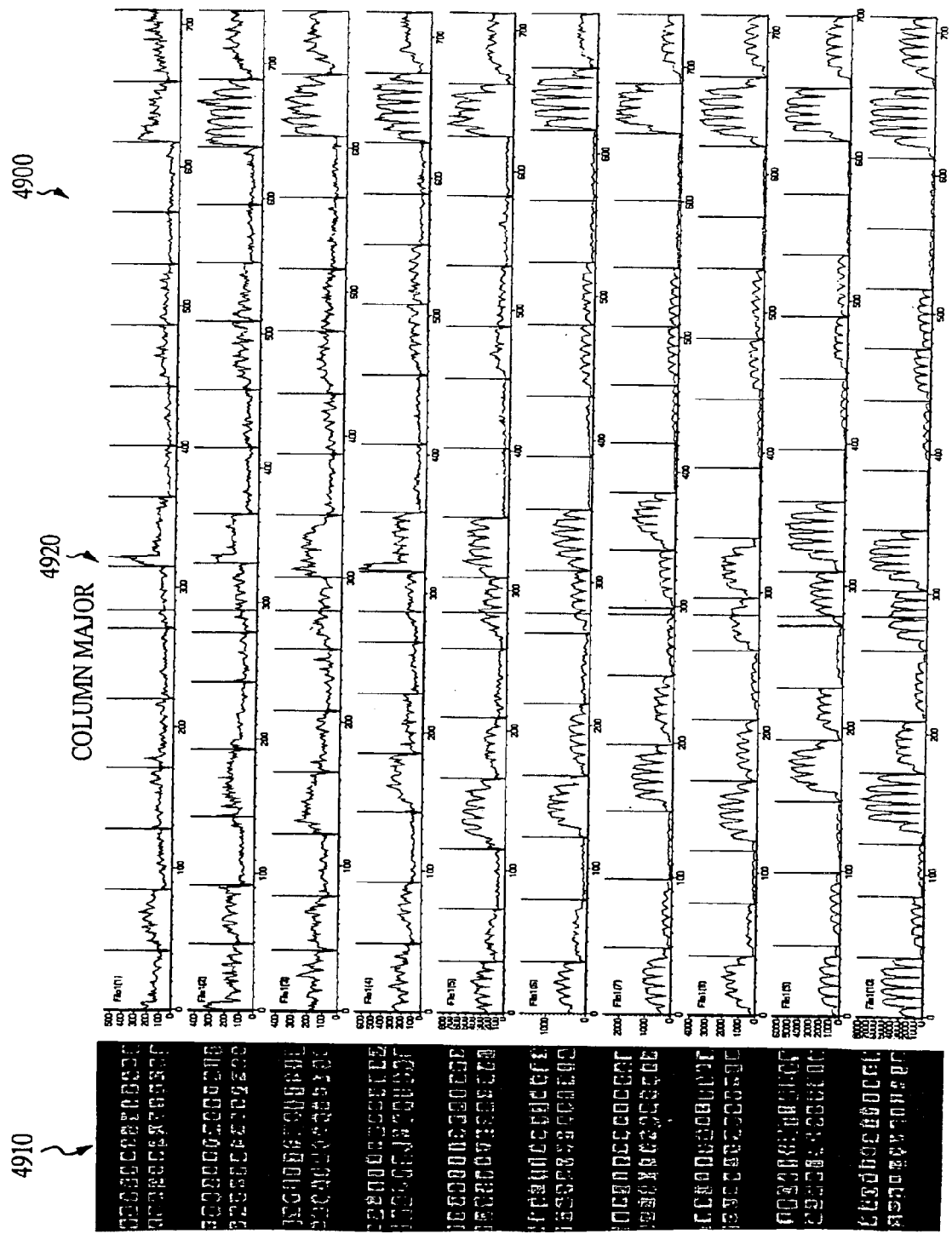
FIG. 49 illustrates a column major extraction of pixels relating to the hybridization of a single serially diluted gene, represented by multiple objects of interest, using a synthesized oligonucleotide microarray.

FIG. 49 illustrates the results of rectilinear extraction for a gene that is represented by multiple probes or feature and includes a computationally constructed pixellated panel of the same gene obtained by deconstructing the features constructing to the gene from several microarray experiments using a synthesized oligonucleotide microarray platform 4910. The experiments present expressions levels for the gene under varying serial dilutions. Each gene is individually represented by 32 features. The panel 4920 shows the spatial distribution of intensities in the extracting core using 16 of the features. Individual features are regular in character and extracted using rectilinear extracted by scanning along the columns in y-direction, and then moving to the next column to the right. The panel 4920 is then spectrally transformed to PSD vectors for further analysis. Both one dimensional and two dimensional DFTs provide comparable results in spectral regime.

In the exemplary embodiment, the following operations are utilized to enhance the spectral resolution of extraction core. First, the spatial core of length N is partitioned into M sub-cores of length J (where J<N). The portioned cores may or may not be overlapping in the spatial domain and the lengths of the sub-cores do not need to be identical. Second, each spatial core of length J is then transformed to a spectral core using FFT described above. Third, the spectral cores of length J are then convolved with 1 discrete kernels where 1>0 with each of the sub-cores being convolved with the same convolution kernel, or in the alternative, each sub-core is convolved with a different convolution kernel. The convolution cascades applied to sub-cores can be of the form of: (i) a serial cascade: with no-recombination of the convolution results; (ii) a parallel cascade which comprises the recombination of the convolution results in the spectral domain after 1 or more convolutions; or (iii) a combination of serial and parallel Cascades which comprises the application of series of convolutions, followed by re-combinations, followed by further convolution cascades.

The extracted pixels that have been transformed into the spectral domain are useful as a stand-alone dataset to characterize the analyzed array as extraneous information not related to an object of interest has been removed through the extraction process and the resolution of the extracted pixels have been increased through spectral domain transformation. In addition, the transformed extracted pixels may also be useful for other applications including parameterizing a pre-determined dynamical system, parameterizing a pre-determined distributed representation of a single canonical dynamical system.

Figure 50:
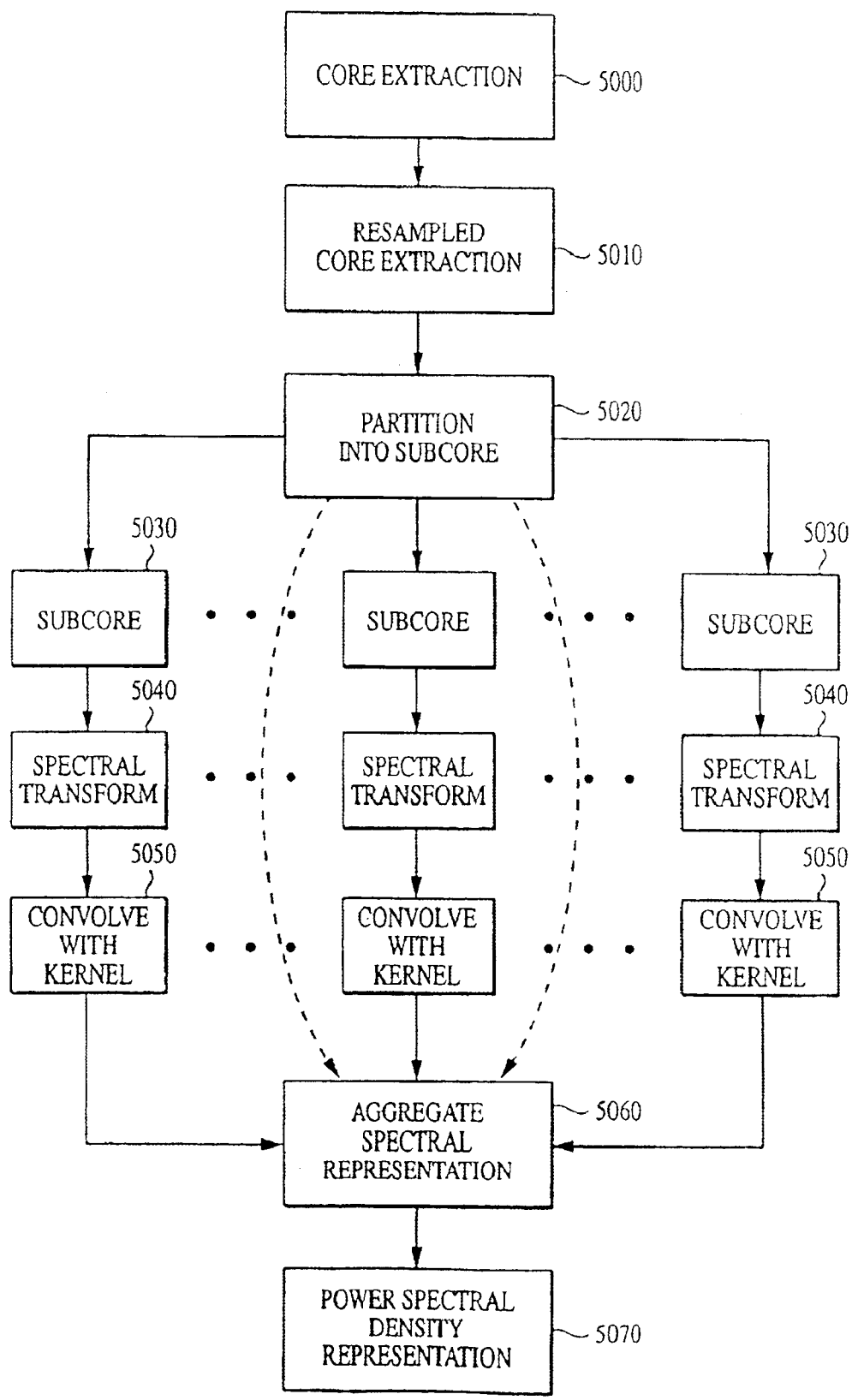
FIG. 50 illustrates a flowchart for transforming an object of interest to a spectral representation by decomposing the extracted core into sub-cores and individually transforming them.

In some embodiments, it may be desirable to partition the extracted core of pixels if the spectral components therein are from a polycyclostationary or a cyclostationary system which represented by k sinusoids. With regard to FIG. 50, an embodiment is disclosed where the extracted core pixels 5000, are re-sampled to enhance spatial resolution 5010, and are then partitioned 5020 into k subcores 5030. The representations for each of the subcores are then transformed from an intensity representation to a spectral representation 5040, and are then convolved with a kernel 5050. The subcores are then added together to form an aggregate spectral representation 5060 which is then used to estimate the power spectral density representation.

The exemplary embodiments have been primarily described with reference to diagrams illustrating pertinent components of the embodiments. It should be appreciated that not all components of a complete implementation of a practical system are necessarily illustrated or described in detail, nor are all of the varying component layout schema described. Rather, only those components and architectures necessary for a thorough understanding of the invention have been illustrated and described in detail. Actual implementations may contain more components or, depending upon the implementation, fewer components. Modifications to the preferred embodiments will be apparent to those skilled in the art. For example, the extraction and re-scaling techniques described above which compensate for low SCR or low SNR are applicable to processing a broad class of spatial and spatio-temporal images. It will also be appreciated that the extraction techniques and spectral transformation techniques described herein are independently useful and need not be practiced together. Consequently, the scope of the present invention should not be limited by the particular embodiments discussed above, but should be defined only by the claims set forth below and equivalents thereof.

What is claimed is:

1. A method for characterizing information from a pixellated output pattern of a microarray having one or more objects of interest, the method comprising:
   extracting pixels within the output pattern representative of each object of interest; and
   transforming the intensity representation of the extracted pixels to a spectral representation, based on an expected signal level for each object of interest.

2. The method of claim 1 wherein the step of extracting pixels utilizes a radial spiral transversal.

3. The method of claim 2 wherein the radial spiral traversal originates at a centroid of each object of interest and progresses outwardly.

4. The method of claim 3 wherein the radial spiral traversal terminates at a segment boundary pixel for each object of interest.

5. The method of claim 3 wherein the radial spiral traversal terminates at a pre-determined distance beyond a segment boundary for each object of interest.

6. The method of claim 3 wherein the radial spiral traversal terminates at a pre-determined distance before a segment boundary for each object of interest.

7. The method of claim 2 wherein the radial spiral traversal converges inwardly toward a centroid of each object of interest.

8. The method of claim 7 wherein the radial spiral traversal terminates at the centroid for each object of interest.

9. The method of claim 7 wherein the radial spiral traversal terminates at a pre-determined distance inside a segment boundary for each object of interest.

10. The method of claim 7 wherein the radial spiral traversal originates at a pre-determined distance outside a segment boundary for each object of interest.

11. The method of claim 7 wherein the radial spiral traversal originates at a pre-determined distance within a segment boundary for each object of interest.

12. The method of claim 7 wherein the radial spiral traversal originates at a segment boundary pixel for each object of interest.

13. The method of claim 2 wherein the radial spiral traversal originates at a pre-determined distance from a centroid of each object of interest and progresses outwardly.

14. The method of claim 2 wherein the radial spiral traversal for pixel extraction is configured to extract pixels associated with objects of interest having varying geometric sizes.

15. The method of claim 2 wherein the radial spiral traversal for pixel extraction is configured to extract pixels associated with objects of interest distributed geometrically irregularly on the microarray.

16. The method of claim 2 wherein the radial spiral traversal for pixel extraction is configured to extract pixels associated with objects of interests having varying geometric sizes and distributed geometrically irregularly on the microarray.

17. The method of claim 1 wherein the step of extracting pixels utilizes a logarithmic spiral.

18. The method of claim 17 wherein the logarithmic spiral uses a tessellated extraction mask.

19. The method of claim 18 wherein the tessellated extraction mask is a texture mask.

20. The method of claim 19 wherein the texture mask is chosen from a group comprising: Bernoulli spiral masks, logistique masks, Hirschorn masks, Voderberg masks, bent-wedge tile masks, kinked tile masks, rhomboidal tile masks, triangular tile masks, equiangular spiral masks, symmetric tessellation masks, asymmetric tessellation masks, and spiral mirabilis masks.

21. The method of claim 1 wherein the step of extracting pixels utilizes an extraction technique from a group comprising: degenerate logarithmic spiral masks, rectilinear masks, row-major extraction, and column-major extraction.

22. The method of claim 1 further comprising computationally re-scaling the extracted pixels to increase spatial resolution of the extracted pixels prior to the step of transforming the intensity representation.

23. The method of claim 22 wherein the step of computationally re-sampling the extracted pixels comprises convolving the extracted pixels with a kernel.

24. The method of claim 23 wherein the kernel is a discretized kernel.

25. The method of claim 24 wherein discretized coefficients of the kernel are chosen from a group comprising; linear functions, non-linear functions, and canonical kernel functions.

26. The method of claim 22 wherein the step of computationally re-scaling the extracted pixels comprises a product of a scalar dot product with an affine transformation, or a linear function.

27. The method of claim 22 wherein the spatial resolution is increased by convolution of the extracted pixels with a canonical coefficient kernel that yields two or more modified pixels for each extracted pixel.

28. The method of claim 22 wherein the computational re-scaling of the extracted pixels utilizes a cascade of computational convolutions with discretized canonical kernel functions, with each successive convolution conducted on the results of preceding convolution.

29. The method of claim 28 wherein the convolution cascade is chosen from a group comprising: a serial cascade, a parallel cascade, and a combination of a serial cascade and a parallel cascade.

30. The method of claim 1 wherein the output pattern comprises an array of spatially contiguous pixels and the step of extracting pixels further comprises determining which pixels are representative of each object of interest.

31. The method of claim 1 wherein the output pattern comprises an array of spatially contiguous pixels and the step of extracting pixels further comprises determining which pixels associated with a morphological representation represent an object of interest.

32. The method of claim 1 wherein the output pattern comprises an array of spatially contiguous pixels and the step of extracting pixels further comprises determining which pixels associated with an object of interest represent a morphological invariant.

33. The method of claim 30 wherein the step of determining which pixels are representative of each object of interest is based on information-theory or an information measure.

34. The method of claim 1 further comprising transforming a domain of the extracted pixels from spatial intensity to spatial frequency.

35. The method of claim 1 wherein the step of transforming the intensity representation of the extracted pixels to a spectral representation uses a Fourier transform.

36. The method of claim 35 wherein the Fourier transform is either a Fast Fourier Transform, or a Discrete Fourier Transform.

37. The method of claim 35 further comprising partitioning a spectral vector representing the transformed pixels into non-overlapping subvectors prior to convolving with discretized coefficients of a function.

38. The method of claim 35 further comprising partitioning a spectral vector representing the transformed pixels into overlapping spectral vectors prior to convolving with discretized coefficients of a function.

39. The method of claim 35 further comprising estimating a power spectral density from a spectral representation of the extracted pixels.

40. The method of claim 35 further comprising decomposing a spectrally transformed vector into subvectors associated with an object of interest.

41. The method of claim 40 wherein each subvector is convolved with a resolution enhancement kernel.

42. The method of claim 41 wherein the convolved subvectors are computationally re-sampled.

43. The method of claim 42 further comprising combining the post-convolution computationally re-sampled transformed spectral subvectors to yield a single spectral vector.

44. The method of claim 1 further comprising decomposing the extracted pixels into a set of discrete extracted objects, wherein each discrete extracted object is transformed into a spectral representation.

45. The method of claim 1 further comprising removing pixels that do not pertain to an object of interest prior to the pixel extraction step.

46. The method of claim 1 further comprising utilizing a logarithmic spiral to estimate a local background of an object of interest.

47. The method of claim 1 wherein the microarray in chosen from a group comprising: hybridized spotted cDNA microarrays, synthesized oligonucleotide arrays, spotted oligonucleotide arrays, peptide nucleotide assays, single nucleotide polymorphism (SNP) arrays, carbohydrate arrays, glycoprotein arrays, protein arrays, proteomic arrays, tissue arrays, antibody arrays, antigen arrays, bioassays, sequencing microarrays, sequencing by hybridization (SBH) microarrays, siRNA duplexes, RNAi arrays glass-based arrays, nylon membrane arrays, thin film, arrays, polymer-substrate arrays, capillary electrophoresis arrays, genospectral arrays, electronic arrays, bead arrays, quantum dot arrays, and gylcan arrays.

48. The method of claim 1 wherein the output pattern is representative of an indicator chosen from a group comprising: fluorescence, chemiluminescence, bioluminescence, and photoluminescence.

49. The method of claim 1 further comprising registering the pixels within the output pattern to approximate locations of the objects of interest.

50. The method of claim 1 further comprising adjusting contrast of the output pattern.

51. The method of claim 50 wherein the contrast is adjusted using a filter from a group comprising: Gabor filters, low-pass band-pass filters, high-pass band-pass filters, edge detection operators, Laplacian filters, and gradient-focusing filters.

52. The method of claim 1 further comprising segmenting the objects of interest within the output pattern prior to the extraction step.

53. A method for characterizing information from a pixellated output pattern of microarray representing one or more objects of interest, the method comprising:

segmenting the output pattern to approximate the locations of the objects of interest within the output pattern;

filtering the segmented output pattern to enhance contrast;

extracting a core of pixels associated with each object of interest;

resampling the extracted core pixels to enhance spatial resolution;

transforming a representation of the resampled extracted core pixels from an intensity domain to a spectral domain;

convolving the transformed spectral domain resampled extracted core pixels with a kernel; and estimating a power spectral density from the convolved transformed spectral domain resampled extracted core pixels.

54. A computer code product, embodied on computer-readable media, that characterizes information from a pixellated output pattern of microarray representing one or more objects of interest, comprising:

computer code that extracts spatial data elements within the output pattern representative of each object of interest; and computer code that transforms an intensity representation of the extracted pixels to a spectral representation based on an expected signal level for each object of interest.

55. A computer system for characterizing information from a pixellated output pattern of a microarray representing one or more objects of interest, comprising: a processor; and a memory coupled to said processor, said memory encoding one or more programs, said one or more programs causing said processor to perform the following steps:

extracting spatial data elements within the output pattern representative of each object of interest; and transforming the intensity representation of the extracted pixels to a spectral representation based on an expected signal level for each object of interest.

56. A system for analyzing an output pattern of an array of detectors, each detector representing one or more objects of interest, comprising:

means for extracting spatial data elements within the output pattern representative of each object of interest; and means for transforming an intensity representation of the extracted pixels to a spectral representation based on the expected signal level for each object of interest.

57. A method for characterizing information from a pixellated output pattern of a microarray having one or more objects of interest, the method comprising:

extracting pixels within the output pattern representative of each object of interest utilizing a technique chosen from a group comprising: logarithmic spirals, degenerate logarithmic spiral masks, rectilinear masks, row-major extraction, and column-major extraction; and transforming an intensity representation of the extracted pixels to a spectral representation.

58. The method of claim 57 wherein the step of transforming the intensity representations of the extracted pixels is dependent upon the expected signal level for each object of interest.

59. The method of claim 57 wherein the step of extracting pixels utilizes a radial spiral transversal.

60. The method of claim 59 wherein the radial spiral traversal originates at a centroid of each object of interest and progresses outwardly.

61. The method of claim 60 wherein the radial spiral traversal terminates at a segment boundary pixel for each object of interest.

62. The method of claim 60 wherein the radial spiral traversal terminates at a pre-determined distance beyond a segment boundary for each object of interest.

63. The method of claim 60 wherein the radial spiral traversal terminates at a pre-determined distance before a segment boundary for each object of interest.

64. The method of claim 59 wherein the radial spiral traversal converges inwardly toward a centroid of each object of interest.

65. The method of claim 59 wherein the radial spiral traversal originates at a pre-determined distance from a centroid of each object of interest and progresses outwardly.

66. The method of claim 59 wherein the radial spiral traversal for pixel extraction is configured to extract pixels associated with objects of interest having varying geometric sizes.

67. The method of claim 59 wherein the radial spiral traversal for pixel extraction is configured to extract pixels associated with objects of interest distributed geometrically irregularly on the microarray.

68. The method of claim 59 wherein the radial spiral traversal for pixel extraction is configured to extract pixels associated with objects of interests having varying geometric sizes and distributed geometrically irregularly on the microarray.

69. The method of claim 64 wherein the radial spiral traversal terminates at the centroid for each object of interest.

70. The method of claim 64 wherein the radial spiral traversal terminate at a pre-determined distance inside a segment boundary for each object of interest.

71. The method of claim 64 wherein the radial spiral traversal originates at a pre-determined distance outside a segment boundary for each object of interest.

72. The method of claim 64 wherein the radial spiral traversal originates at a pre-determined distance within a segment boundary for each object of interest.

73. The method of claim 64 wherein the radial spiral traversal originates at a segment boundary pixel for each object of interest.

74. The method of claim 57 wherein the logarithmic spiral uses a tessellated extraction mask.

75. The method of claim 74 wherein the tessellated extraction mask is a texture mask.

76. The method of claim 75 wherein the texture mask is chosen from a group comprising: Bernoulli spiral masks, logistique masks, Hirschorn masks, Voderberg masks, bent-wedge tile mask, kinked tile masks, rhomboidal tile masks, triangular tile masks, equiangular spiral mask, symmetric tessellation masks, asymmetric tessellation masks, and spiral mirabilis masks.

77. The method of claim 57 further comprising computationally re-scaling the extracted pixels to increase spatial resolution of the extracted pixels prior to the step of transforming the intensity representation.

78. The method of claim 77 wherein the step of computationally re-scaling the extracted pixels comprises convolving the extracted pixels with a kernel.

79. The method of claim 78 wherein the kernel is a discretized Kernel.

80. The method of claim 79 wherein discretized coefficients of the kernel are chosen from a group comprising: linear functions, non-linear functions, and canonical kernel functions.

81. The method of claim 77 wherein the step of computationally re-scaling the extracted pixels comprises a product of a scalar dot product with an affine transformation, or a linear function.

82. The method of claim 77 wherein the spatial resolution is increased by convolution of the extracted pixels with a canonical coefficient kernel that yields two or more modified pixels for each extracted pixel.

83. The method of claim 77 wherein the computational re-scaling of the extracted pixels utilizes a cascade of computational convolutions with discretized canonical kernel functions, with each successive convolution conducted on the results of preceding convolution.

84. The method of claim 83 wherein the convolution cascade is chosen from a group comprising: a serial cascade, a parallel cascade, and a combination of a serial cascade and a parallel cascade.

85. The method of claim 57 wherein the output pattern comprises an array of spatially contiguous pixels and the step of extracting pixels further comprises determining which pixels are representative of each object of interest.

86. The method of claim 85 wherein the step of determining which pixels are representative of each object of interest is based on formation-theory or an information measure.

87. The method of claim 57 wherein the output pattern comprises an array of spatially contiguous pixels and the step of extracting pixels further comprises determining which pixels associated with a morphological representation represent an object of interest.

88. The method of claim 57 wherein the output pattern comprises an array of spatially contiguous pixels and the step of extracting pixels further comprises determining which pixels associated with an object of interest represent a morphological invariant.

89. The method of claim 57 further comprising transforming a domain of the extracted pixels from spatial intensity to spatial frequency.

90. The method of claim 57 wherein the step of transforming the intensity representation of the extracted pixels to a spectral representation uses a Fourier transform.

91. The method of claim 90 wherein the Fourier transform is either a Fast Fourier transform, or a Discrete Fourier Transform.

92. The method of claim 90 further comprising partitioning a spectral vector representing the transformed pixels into non-overlapping subvectors prior to convolving with discretized coefficients of a function.

93. The method of claim 90 further comprising partitioning a spectral vector representing the transformed pixels into overlapping spectral vectors prior to convolving with discretized coefficients of a function.

94. The method of claim 90 further comprising estimating a power spectral density from a spectral representation of the extracted pixels.

95. The method of claim 90 further comprising decomposing a spectrally transformed vector into subvectors associated with an object of interest.

96. The method of claim 95 wherein each subvector is convolved with a resolution enhancement kernel.

97. The method of claim 96 wherein the convolved subvector are computationally re-sampled.

98. The method of claim 97 further comprising combining the post-convolution computationally re-sampled transformed spectral subvectors to yield a single spectral vector.

99. The method of claim 57 further comprising decomposing the extracted pixels into a set of discrete extracted objects, wherein each discrete extracted object is transformed into a spectral representation.

100. The method of claim 57 further comprising removing pixels that do not pertain to an object of interest prior to the pixel extraction step.

101. The method of claim 57 further comprising utilizing a logarithmic spiral to estimate a local background of an object of interest.

102. The method of claim 57 wherein the microarray is chosen from a group comprising: hybridized spotted cDNA microarray, synthesized oligonucleotide arrays, spotted oligonucleotide arrays, peptide nucleotide assays, single nucleotide polymorphism (SNP) arrays, carbohydrate arrays, glycoprotein arrays, protein arrays, proteomic arrays, tissue arrays, antibody arrays, antigen arrays, bioassays, sequencing microarrays, sequencing by hybridization (SBH) microarrays, siRNA duplexes, RNAi arrays glass-based arrays, nylon membrane arrays, thin film arrays, polymer-substrate arrays, capillary electrophoresis arrays, genospectral arrays, electronic arrays, bead arrays, quantum dot arrays, and gylcan arrays.

103. The method of claim 57 wherein the output pattern is representitive of an indicator chosen from a group comprising; fluorescence, chemiluminescence, bioluminescence, and photoluminescence.

104. The method of claim 57 further comprising registering the pixels within the output pattern to approximate the location of the objects of interest.

105. The method of claim 57 further comprising adjusting contrast of the output pattern.

106. The method of claim 105 wherein the contrast is adjusted using a filter from a group comprising: Gabor filters, low-pass band-pass filters, high-pass band-pass filters, edge detection operators, Laplacian filters, and gradient-focusing filters.

107. The method of claim 57 further comprising segmenting the objects of interest within the output pattern prior to the extraction step.

108. A computer code product, embodied on a computer-readable media, that characterizes information from a pixellated output pattern of microarray representing one or more objects of interest, comprising:
computer code that extracts spatial data elements within the output pattern representative of each object of interest utilizing a technique chosen from a group comprising: logarithmic spirals, degenerate logarithmic spiral masks, rectilinear masks, row-major extraction, and column-major extraction; and
computer code that transforms an intensity representation the extracted pixels to a spectral representation.

109. A computer system for characterizing information from a pixellated output pattern of a microarray representing one or more objects of interest, comprising: a processor; and a memory coupled to said processor, said memory encoding one or more programs, said one or more programs causing said processor to perform the following steps:
extracting spatial data elements within the output pattern representative of each object of interest utilizing a technique chosen from a group comprising: logarithmic spirals, degenerate logarithmic spiral masks, rectilinear masks, row-major extraction, and column-major extraction; and
transforming an intensity representation of the extracted pixels to a spectral representation.

110. A system for analyzing an output pattern of an array of detectors, each detector representing one or more objects of interest, comprising:
means for extracting spatial data elements within the output pattern representative of each object of interest utilizing a technique chosen from a group comprising: logarithmic spirals, degenerate logarithmic spiral masks, rectilinear masks, row-major extraction, and column-major extraction; and
means for transforming an intensity representation of the extracted pixels to a spectral representation.

111. The method of claim 110 wherein the step of extracting pixels utilizes a logarithmic spiral.

112. The method of claim 111 wherein the logarithmic spiral uses a tessellated extraction mask.

113. The method of claim 112 wherein the tessellated extraction mask is a texture mask.

114. The method of claim 113 wherein the texture mask is chosen from a group comprising: Bernoulli spiral masks, logistique masks, Hirschorn masks, Voderberg masks, bent-wedge tile masks, kinked tile masks, rhomboidal tile masks, triangular tile masks, equiangular spiral masks, symmetric tessellation masks, asymmetric tessellation masks, and spiral mirabilis masks.

115. A method for characterizing information from a pixellated output pattern of a microarray having one or more objects of interest, the method comprising:
extracting pixels within the output pattern representative of each object of interest;
utilizing a logarithmic spiral to estimate a local background of each object of interest; and
transforming an intensity representation of the extracted pixels to a spectral representation.

116. The method of claim 115 wherein the step of transforming the intensity representations of the extracted pixels is dependent upon the expected signal level for each object of interest.

117. The method of claim 115 wherein the step of extracting pixels utilizes a radial spiral transversal.

118. The method of claim 117 wherein the radial spiral traversal originates at a centroid of each object of interest and progresses outwardly.

119. The method of claim 118 wherein the radial spiral traversal terminates at a segment boundary pixel for each object of interest.

120. The method of claim 118 wherein the radial spiral traversal terminates at a pre-determined distance beyond a segment boundary for each object of interest.

121. The method of claim 118 wherein the radial spiral traversal terminates at a pre-determined distance before a segment boundary for each object of interest.

122. The method of claim 118 wherein the radial spiral traversal for pixel extraction is configured to extract pixels associated with objects of interest having varying geometric sizes.

123. The method of claim 118 wherein the radial spiral traversal for pixel extraction is configured to extract pixels associated with objects of interest distributed geometrically irregularly or the microarray.

124. The method of claim 118 wherein the radial spiral traversal for pixel extraction is configured to extract pixels associated with objects of interests having varying geometric sizes and distributed geometrically irregularly on the microarray.

125. The method of claim 117 wherein the radial spiral traversal converges inwardly toward a centroid of each object of interest.

126. The method of claim 125 wherein the radial spiral traversal terminates at the centroid for each object of interest.

127. The method of claim 125 wherein the radial spiral traversal terminates at a pre-determined distance inside a segment boundary for each object of interest.

128. The method of claim 125 wherein, the radial spiral traversal originates at a pre-determined distance outside a segment boundary for each object of interest.

129. The method of claim 125 wherein the radial spiral traversal originates at a pre-determined distance within a segment boundary for each object of interest.

130. The method of claim 125 wherein the radial spiral traversal originates at a segment boundary pixel for each object of interest.

131. The method of claim 117 wherein the radial spiral traversal originates at a pre-determined distance from a centroid of each object of interest and progresses outwardly.

132. The method of claim 115 wherein the step of extracting pixels utilizes an extraction technique from a group comprising: degenerate logarithmic spiral masks, rectilinear masks, row-major extraction, and column-major extraction.

133. The method of claim 115 further comprising computationally re-scaling the extracted pixels to increase spatial resolution of the extracted pixels prior to the step of transforming the intensity representation.

134. The method of claim 133 wherein the step of computationally re-scaling the extracted pixels comprises convolving the extracted pixels with a kernel.

135. The method of claim 134 wherein the kernel is a discretized kernel.

136. The method of claim 135 wherein discretized coefficients of the kernel are chosen from a group comprising: linear functions, non-linear functions, and canonical kernel functions.

137. The method of claim 133 wherein the step of computationally re-scaling the extracted pixels comprises a product of a scalar dot product with an affine transformation, or a linear function.

138. The method of claim 133 wherein the spatial resolution is increased by convolution of the extracted pixels with a canonical coefficient kernel that yields two or more modified pixels for each extracted pixel.

139. The method of claim 133 wherein the computational re-scaling of the extracted pixels utilizes a cascade of computational convolutions with discretized canonical kernel functions with each successive convolution conducted on the results of preceding convolution.

140. The method of claim 133 wherein the convolution cascade is chosen from a group comprising: a serial cascade, a parallel cascade, and a combination of a serial cascade and a parallel cascade.

141. The method of claim 115 wherein the output pattern comprises on array of spatially contiguous pixels and the step of extracting pixels further comprises determining which pixels are representative of each object of interest.

142. The method of claim 141 wherein the step of determining which pixels are representative of each object of interest is based on information-theory or an information measure.

143. The method of claim 115 wherein the output pattern comprises an array of spatially contiguous pixels and the step of extracting pixels further comprises determining which pixels associated with a morphological representation represent an object of interest.

144. The method of claim 115 wherein the output pattern comprises an array spatially contiguous pixels and the step of extracting pixels further comprises determining which pixels associated with an object of interest represent a morphological invariant.

145. The method of claim 115 further comprising transforming a domain of the extracted pixels from spatial intensity to spatial frequency.

146. The method of claim 115 wherein the step of transforming the intensity representation of the extracted pixels to spectral representation uses a Fourier transform.

147. The method of claim 146 wherein the Fourier transform is either a Fast Fourier Transform, or a Discrete Fourier Transform.

148. The method of claim 146 further comprising partitioning a spectral vector representing the transformed pixels into non-overlapping subvectors prior to convolving with discretized coefficients of a function.

149. The method of claim 146 further comprising partitioning a spectral vector representing the transformed pixels into overlapping spectral vectors prior to convolving with discretized coefficients of a function.

150. The method of claim 146 further comprising estimating a power spectral density from a spectral representation of the extracted pixels.

151. The method of claim 146 further comprising decomposing a spectrally transformed vector into subvectors associated with an object of interest.

152. The method of claim 151 wherein each subvector is convolved with a resolution enhancement kernel.

153. The method of claim 152 wherein the convolved subvectors are computationally re-sampled.

154. The method of claim 153 further comprising combining the post-convolution computationally re-sampled transformed spectral subvectors to yield a single spectral vector.

155. The method of claim 115 further comprising decomposing the extracted pixels into a set of discrete extracted objects, wherein each discrete extracted object, is transformed into a spectral representation.

156. The method of claim 115 further comprising removing pixels that do not pertain to an object of interest prior to the pixel extraction step.

157. The method of claim 115 wherein the microarray is chosen from a group comprising: hybridized spotted cDNA microarrays, synthesized oligonucleotide arrays, spotted oligonucleotide arrays, peptide nucleotide assays, single nucleotide polymorphism (SNP) arrays, carbohydrate arrays, glycoprotein arrays, protein arrays, proteomic arrays, tissue arrays, antibody arrays, antigen arrays, bioassays, sequencing microarrays, sequencing by hybridization (SBH) microarrays, siRNA duplexes, RNAi arrays glass-based arrays, nylon membrane arrays, thin film arrays, polymer-substrate arrays, capillary electrophoresis arrays, genospectral arrays, electronic arrays, bead arrays, quantum dot arrays, and glycan arrays.

158. The method of claim 115 wherein the output pattern is representative of an indicator chosen from a group comprising; fluorescence chemiluminescence, bioluminescence, and photoluminescence.

159. The method of claim 115 further comprising registering the pixels within the output pattern to approximate location of the objects of interest.

160. The method of claim 115 further comprising adjusting contrast of the output pattern.

161. The method of claim 160 wherein the contrast is adjusted using a filter from a group comprising: Gabor filters, low-pass band-pass filters, high-pass band-pass filters, edge detection operators, Laplacian filters, and gradient-focusing filters.

162. The method of claim 115 further comprising segmenting the objects of interest within the output pattern prior to the extraction step.

163. A computer code product, embodied on a computer-readable media, that characterizes information from a pixellated output pattern of microarray representing one or more objects of interest, comprising:
 computer code that extracts spatial data elements within the output pattern representative of each object of interest;
 computer code that utilizes a logarithmic spiral to estimate a local background of each object of interest; and
 computer code that transforms an intensity representation of the extracted pixels to a spectral representation.

164. A computer system for characterizing information from a pixellated output pattern of a microarray representing one or more objects of interest, comprising: a processor; and a memory coupled to said processor, said memory encoding one or more programs, said one or more programs causing said processor to perform the following steps:
 extracting spatial data elements within the output pattern representative of each object of interest;
 utilizing a logarithmic spiral to estimate a local background of each object of interest; and
 transforming an intensity representation of the extracted pixels to a spectral representation.

165. A system for analyzing an output pattern of an array detectors, each detector representing one or more objects of interest, comprising:
 means for extracting spatial data elements within the output pattern representative of each object of interest;
 means for utilizing a logarithmic spiral to estimate a local background of each object of interest; and
 means for transforming an intensity representation of the extracted pixels to a spectral representation.

166. A method for characterizing information from a pixellated output pattern of a microarray having one or more objects of interest the method comprising:
 extracting pixels within the output pattern representative of each object of interest utilizing a radial spiral transversal;
 transforming an intensity presentation of the extracted pixels to a spectral representation;
 wherein the radial spiral traversal originates at or near a centroid of each object of interest and progresses outwardly; and
 wherein the radial spiral traversal terminates either at a pre-determined distance beyond a segment boundary for each object of interest or at a pre-determined distance before a segment boundary for each object of interest.

167. A computer code product, embodied on a computer-readable media that characterizes information from a pixellated output pattern of microarray representing one or more objects of interest, comprising:
 computer code that extracts spatial data elements within the output pattern representative of each object of interest utilizing a radial spiral transversal;
 computer code that transform an intensity representation of the extracted pixels to a spectral representation;
 wherein the radial spiral traversal originates at or near a centroid of each object of interest and progresses outwardly; and
 wherein the radial spiral traversal terminates either at a pre-determined distance beyond a segment boundary for each object of interest or at a pre-determined distance before a segment boundary for each object of interest.

168. A computer system for characterizing information from pixellated output pattern of a microarray representing one or more objects of interest, comprising: a processor; and a memory coupled to said processor, said memory encoding one or more programs, said one or more programs causing said processor to perform the following steps:
 extracting spatial data elements within the output pattern representative of each object of interest utilizing a radial spiral transversal; and
 transforming an intensity representation of the extracted pixels to a spectral representation;
 wherein the radial spiral traversal originates at or near a centroid of each object of interest and progresses outwardly; and
 wherein the radial spiral traversal terminates either at a pre-determined distance beyond a segment boundary for each object of interest or at a pre-determined distance before a segment boundary for each object of interest.

169. A system for analyzing an output pattern of an array of detectors, each detector representing one or more objects of interest, comprising:
 means for extracting spatial data elements within the output pattern representative of each object of interest utilizing a radial spiral transversal; and
 means for transforming an intensity representation of the extracted pixels to a spectral representation;
 wherein the radial spiral traversal originates at or near a centroid of each object of interest and progresses outwardly; and
 wherein the radial spiral traversal terminates either at a pre-determined distance, beyond a segment boundary for each object of interest or at a pre-determined distance before a segment boundary for each object of interest.

170. A method for characterizing information from a pixellated output pattern of a microarray having one or more objects of interest the output pattern including an array of spatially contiguous pixels, the method comprising:
 extracting pixels within the output pattern representative of each object of interest; and
 transforming an intensity representation of the extracted pixels to a spectral representation; and
 wherein the extracting step comprises determining which pixels are representative of each object of interest.

171. A computer code product, embodied on a computer-readable media, that characterizes information from a pixellated output pattern of microarray representing one or more objects of interest, the output pattern including an array of spatially contiguous pixels, the computer code product comprising:

computer code that extracts spatial data elements within the output pattern representative of each object of interest; and computer code that transforms an intensity representation of the extracted pixels to a spectral representation;

wherein the computer code that extracts spatial data elements determines which pixels are representative of each object of interest.

172. A computer system for characterizing information from a pixellated output pattern of a microarray representing one or more objects of interest, the output pattern including an array of spatially contiguous pixels, the computer system comprising: a processor; and a memory coupled to said processor, said memory encoding one or more programs, said one or more programs causing said processor to perform the following steps:

extracting spatial data elements within the output pattern representative of each object of interest;

transforming an intensity representation of the extracted pixels to a spectral representation; and wherein the extracting step comprises determining which pixels are representative of each object of interest.

173. A system for analyzing an output pattern of an array of detectors, each detector representing one or more objects of interest, comprising:

means for extracting spatial data, elements within the output pattern representative of each object of interest;

means for transforming an intensity representation of the extracted pixels to a spectral representation; and wherein the extraction means determines which pixels are representative of each object of interest.

174. A method for characterizing information from a pixellated output pattern of a microarray having one or more object of interest the output pattern including an array of spatially contiguous pixels, the method comprising:

extracting pixels within the output pattern representative of each object of interest; and transforming an intensity representation of the extracted pixels to a spectral representation; and wherein the extracting step comprises determining which pixels pixels are associated with a morphological representation represents an object of interest.

175. A computer code product, embodied on a computer-readable media, that characterizes information from a pixellated output pattern of microarray representing one or more objects of interest, the output pattern including an array of spatially contiguous pixels, the computer code product comprising:

computer code that extracts spatial data elements within the output pattern representative of each object of interest; and computer code that transforms an intensity representation of the extracted pixels to a spectral representation;

wherein the computer code that extracts spatial data elements determines which pixels associated with a morphological representation represents an object of interest.

176. A computer system for characterizing information from a pixellated output pattern of a microarray representing one or more objects of interest, the output pattern including an array of spatially contiguous pixels, the computer system comprising a processor; and a memory coupled to said processor, said memory encoding one or more programs, said one or more programs causing said processor to perform the following steps;

extracting spatial data elements within the output pattern representative of each object of interest;

transforming an intensity representation of the extracted pixels to a spectral representation; and wherein the extracting step comprises determining which pixels associated with a morphological representation represents an object of interest.

177. A system for analyzing an output pattern of an array of detectors, each detector representing one or more objects of interest, comprising:

means for extracting spatial data elements within the output pattern representative of each object of interest;

means for transforming an intensity representation of the extracted pixels to a spectral representation; and wherein the extraction means determines which pixels associated with an object interest represent a morphological invariant.

178. A method for characterizing information from a pixellated output pattern of a microarray having one or more objects of interest the output pattern including an array of spatially contiguous pixels, the method comprising:

extracting pixels within the output pattern representative of each object of interest; and transforming an intensity representation of the extracted pixels to a spectral representation; and wherein the extracting step comprises determining which pixels associated with an object of interest represent a morphological invariant.

179. A computer code product, embodied on a computer-readable media, that characterizes information from a pixellated output pattern of microarray representing one or more objects of interest, the output pattern including an array of spatially contiguous pixels, the computer code product comprising:

computer code that extracts spatial data elements within the output pattern representative of object of interest; and computer code that transforms an intensity representation of the extracted pixels to a spectral representation wherein the computer code that extracts spatial data elements determines which pixels associated with an object of interest represent a morphological invariant.

180. A computer system for characterizing information from a pixellated output pattern of a microarray representing one or more objects of interest, the output pattern including an array of spatially contiguous pixels, the computer system comprising a processor; and a memory coupled to said processor, said memory encoding one or more programs, said one or more program causing said processor to perform the following steps:

extracting spatial data elements within the output pattern representative of each object of interest;

transforming an intensity representation of the extracted pixels to a spectral representation; and wherein the extracting step comprises determining which pixels associated with an object of interest represent a morphological invariant.

181. A system for analyzing an output pattern of an array of detectors, each detector representing one or more objects of interest, comprising:

means for extracting spatial data elements within the output pattern representative of each object of interest;

means for transforming an intensity representation of the extracted pixels to a spectral representation; and wherein the extraction means determines pixels associated with an object of interest represent a morphological invariant.

182. A method for characterizing information from a pixellated output pattern of a microarray having one or more objects of interest, the method comprising:

extracting pixels within the output pattern representative of each object of interest;

transforming an intensity representation of the extracted pixel to a spectral representation using a Fourier transform; and partitioning a spectral vector representing the transformed pixels into either overlapping or non-overlapping subvectors prior to convolving with discretized coefficients of a function.

183. A computer code product, embodied on a computer-readable media, that characterizes information from a pixellated output pattern of microarray representing one or more objects of interest, comprising:

computer code that extracts spatial data elements within the output pattern representative of each object of interest;

computer code that transforms an intensity representation of the extracted pixels to a spectral representation; and computer code that partitions a spectral vector representing the transformed pixels into either overlapping or non-overlapping subvectors prior to convolving with discretized coefficients of a function.

184. A computer system for characterizing information from a pixellated output pattern of a microarray representing one or more objects of interest, comprising: a processor; and a memory coupled to said processor, said memory encoding one or more programs, said one or more programs causing said processor to perform the following steps:

extracting spatial data elements within the output pattern representative of each object of interest;

transforming an intensity representation of the extracted pixels to a spectral representation; and partitioning a spectral vector representing the transformed pixels into either overlapping or non-overlapping subvectors prior to convolving with discretized coefficients of a function.

185. A system for analyzing an output pattern of an array of detectors, each detector representing one or more objects of interest, comprising:

means for extracting spatial data elements within the output pattern representative of each object of interest;

means for transforming an intensity representation of the extracted pixels to representation; and means for partitioning a spectral vector representing the transformed pixels into either overlapping or non-overlapping subvectors prior to convolving with discretized coefficients of a function.

186. A method for characterizing information from a pixellated output pattern of a microarray having one or more objects of interest, the method comprising:

extracting pixels within the output pattern representative of each object of interest;

transforming an intensity representation of the extracted pixel to a spectral representation using a Fourier transform; and decomposing a spectrally transformed vector into subvectors associated with an object of interest.

187. A computer code product, embodied on a computer-readable media, that characterizes information from a pixellated output pattern of microarray representing one or more objects of interest comprising:

computer code that extracts spatial data elements within the output pattern representative of each object of interest;

computer code that transforms an intensity representation of the extracted pixels to a spectral representation; and computer code that decomposes a spectrally transformed vector into subvectors associated with an object of interest.

188. A computer system for characterizing information from a pixellated output pattern of a microarray representing one or more objects of interest, comprising: a processor; and a memory coupled to said processor, said memory encoding one or more programs, said one or more programs causing said processor to perform the following steps:

extracting spatial data elements within the output pattern representative of each object of interest;

transforming an intensity representation of the extracted pixels to a spectral representation; and decomposing a spectrally transformed vector into subvectors associated with an object of interest.

189. A system for analyzing an output pattern of an array of detectors, each detector representing one or more objects of interest, comprising:

means for extracting spatial data elements within the output pattern representative of each object of interest;

means for transforming an intensity representation of the extracted pixels to a representation; and means for decomposing a spectrally transformed vector into subvectors associated with an object of interest.

190. A method for characterizing information from a pixellated output pattern of a microarray having one or more objects of interest, the method comprising:

extracting pixels within the output pattern representative of each object of interest using logarithmic extraction means;

transforming an intensity representation of the extracted pixel to a spectral representation; and wherein the output pattern is representative of an indicator chosen from a group comprising chemiluminescence, bioluminescence, and photoluminescence.

191. A computer code product, embodied on a computer-readable media that characterizes information from a pixellated output pattern of microarray representing one or more objects of interest comprising:

computer code that extracts spatial data elements within the output pattern representative of each object of interest using logarithmic extraction means;

computer code that transforms an intensity representation of the extracted pixels to a spectral representation; and wherein the output pattern representative of an indicator chosen from a group comprising: chemiluminescence, bioluminescence, and photoluminescence.

192. A computer system for characterizing information from a pixellated output pattern of a microarray representing one or more objects of interest, comprising: a processor; and a memory coupled to said processor, said memory encoding one or more programs, said one or more programs causing said processor to perform the following steps:

extracting spatial data elements within the output pattern representative of each object of interest using logarithmic extraction means;

transforming an intensity representation of the extracted pixels to a spectral representation; and wherein the output pattern representative of an indicator chosen from a group comprising: chemiluminescence, bioluminescence, and photoluminescence.

193. A system for analyzing an output pattern of an array of detectors, each detector representing one or more objects of interest, comprising:

means for extracting spatial data elements within the output pattern representative of each object of interest using logarithmic extraction means;

means for transforming an intensity representation of the extracted pixels to representation; and wherein the output pattern representative of an indicator chosen from a group comprising: chemiluminescence, bioluminescence, and photoluminescence.

194. A method for characterizing information from a pixellated output pattern of a microarray having one or more objects of interest, the method comprising:

extracting pixels within the output pattern representative of each object of interest using logarithmic extraction means;

adjusting the contrast of the output pattern using a filter chosen from a group comprising: Gabor filters, edge detection operators Laplacian filters, and gradient-focusing filters; and transforming the intensity representation of the extracted pixels to a spectral representation.

195. A computer code product, embodied on a computer-readable media, that characterizes information from a pixellated output pattern of microarray representing one or more objects of interest, comprising:

computer code that extracts spatial data elements within the output pattern representative of each object of interest using logarithmic extraction means;

computer code that adjusts contrast of the output pattern using a filter chosen from a group comprising: Gabor filters, edge detection operators, Laplacian filters, and gradient-focusing filters; and computer code that transforms an intensity representation of the extracted pixels to a spectral representation.

196. A computer system for characterizing information from a pixellated output pattern of a microarray representing one or more objects of interest, comprising: a processor; and a memory coupled to said processor, said memory encoding one or more programs, said one or more programs causing said processor to perform the following steps:

extracting spatial data elements within the output pattern representative of each object of interest using logarithmic extraction means;

adjusting contrast of the output pattern using a filter chosen from a group comprising: Gabor filters, edge detection operators, Laplacian filters, and gradient-focusing filters; and transforming the intensity representation of the extracted pixels to a spectral representation.

197. A system for analyzing an output pattern of an array of detectors, each detector representing one or more objects of interest, comprising:

means for logarithmically extracting spatial data elements within the output pattern representative of each object of interest;

means for adjusting contrast of the output pattern using a filter chosen from a group comprising: Gabor filters, edge detection operators, Laplacian filters, and gradient-focusing filters; and means for transforming an intensity representation of the extracted pixels to a spectral representation.

198. A method for characterizing information from a pixellated output pattern of a microarray having one or more objects of interest, the method comprising:

segmenting the object of interest within the output pattern using tessellation;

extracting pixels within the output pattern representative of each object of interest; and transforming the intensity representation of the extracted pixels to a spectral representation.

199. The method of claim 198 wherein the step of transforming the intensity representations of the extracted pixels is dependent upon the expected signal level for each object of interest.

200. The method of claim 198 wherein the step of extracting pixels utilizes a radial spiral transversal.

201. The method of claim 200 wherein the radial spiral traversal originates at a centroid of each object of interest and progress outwardly.

202. The method of claim 201 wherein the radial spiral traversal terminates at a segment boundary pixel for each object of interest.

203. The method of claim 201 wherein the radial spiral traversal terminates at a pre-determined distance beyond a segment boundary for each object of interest.

204. The method of claim 201 wherein the radial spiral traversal terminates at a pre-determined distance before a segment boundary for each object of interest.

205. The method of claim 200 wherein the radial spiral traversal converges inwardly toward a centroid of each object of interest.

206. The method of claim 205 wherein the radial spiral traversal terminates at the centroid for each object of interest.

207. The method of claim 205 wherein the radial spiral traversal terminates at a pre-determined distance inside a segment boundary for each object of interest.

208. The method of claim 205 wherein, the radial spiral traversal originates at a pre-determined distance outside a segment boundary for each object of interest.

209. The method of claim 205 wherein the radial spiral traversal originates at a pre-determined distance within a segment boundary for each object of interest.

210. The method of claim 205 wherein the radial spiral traversal originates at a segment boundary pixel for each object of interest.

211. The method of claim 200 wherein the radial spiral traversal originates at a pre-determined distance from a centroid of each object of interest and progresses outwardly.

212. The method of claim 200 wherein the radial spiral traversal for pixel extraction is configured to extract pixels associated with objects of interest having varying geometric sizes.

213. The method of claim 200 wherein the radial spiral traversal for pixel extraction is configured to extract pixels associated with objects of interest distributed geometrically irregularly or the microarray.

214. The method of claim 200 wherein the radial spiral traversal for pixel extraction is configured to extract pixels associated with objects of interests having varying geometric sizes and distributed geometrically irregularly on the microarray.

215. The method of claim 198 wherein the step of extracting pixels utilizes a logarithmic spiral.

216. The method of claim 215 wherein the logarithmic spiral uses tessellated extraction mask.

217. The method of claim 216 wherein the tessellated extraction mask is a texture mask.

218. The method of claim 217 wherein the texture mask is chosen from a group comprising: Bernoulli spiral masks, logistique masks, Hirschorn masks, Voderberg masks, bent-wedge tile masks, kinked tile masks, rhomboidal tile masks, triangular tile masks, equiangular spiral masks, symmetric tessellation masks, asymmetric tessellation masks, and spiral mirabilis masks.

219. The method of claim 198 wherein the step of extracting pixels utilizes an extraction technique from a group comprising: degenerate logarithmic spiral masks, rectilinear masks, row-major extraction, and column-major extraction.

220. The method of claim 198 further comprising computationally re-scaling the extracted pixels to increase spatial resolution of the extracted pixels prior to the step of transforming the intensity representation.

221. The method of claim 220 wherein the step of computationally re-scaling the extracted pixels comprises convolving the extracted pixels with a kernel.

222. The method of claim 221 wherein the kernel is a discretized kernel.

223. The method of claim 222 wherein discretized coefficients of the kernel are chosen from a group comprising: linear functions, non-linear functions, and canonical kernel functions.

224. The method of claim 220 wherein the step of computationally re-scaling the extracted pixels comprises a product a scalar dot product with an affine transformation, or a linear function.

225. The method of claim 220 wherein the spatial resolution is increased by convolution of the extracted pixels with a canonical coefficient kernel that yields two or more modified pixels for each extracted pixel.

226. The method of claim 220 wherein the computational re-scaling of the extracted pixels utilizes a cascade of computational convolutions with discretized canonical kernel functions, with each successive convolution conducted on the results of preceding convolution.

227. The method of claim 226 wherein the convolution cascade is chosen from a group comprising: a serial cascade, a parallel cascade, and a combination of a serial cascade and a parallel cascade.

228. The method of claim 198 wherein the output pattern comprises on array of spatially contiguous pixels and the step of extracting pixels further comprises determining which pixels are representative of each object of interest.

229. The method of claim 228 wherein the step of determining which pixels are representative of each object of interest is based on information-theory or an information measure.

230. The method of claim 198 wherein the output pattern comprises an array of spatially contiguous pixels and the step of extracting pixels further comprises determining which pixels associated with a morphological representation represent an object of interest.

231. The method of claim 198 wherein the output pattern comprises an array spatially contiguous pixels and the step of extracting pixels further comprises determining which pixels associated with an object of interest represent a morphological invariant.

232. The method of claim 198 further comprising transforming a domain of the extracted pixels from spatial intensity to spatial frequency.

233. The method of claim 198 wherein the step of transforming the intensity representation of the extracted pixels to spectral representation uses a Fourier transform.

234. The method of claim 233 wherein the Fourier transform is either a Fast Fourier Transform, or a Discrete Fourier Transform.

235. The method of claim 233 further comprising partitioning a spectral vector representing the transformed pixels into non-overlapping subvectors prior to convolving with discretized coefficients of a function.

236. The method of claim 233 further comprising partitioning a spectral vector representing the transformed pixels into overlapping spectral vectors prior to convolving with discretized coefficients of a function.

237. The method of claim 233 further comprising estimating a power spectral density from a spectral representation of the extracted pixels.

238. The method of claim 233 further comprising decomposing a spectrally transformed vector into subvectors associated with an object of interest.

239. The method of claim 238 wherein each subvector is convolved with a resolution enhancement kernel.

240. The method of claim 239 wherein the convolved subvectors are computationally re-sampled.

241. The method of claim 240 further comprising combining the post-convolution computationally re-sampled transformed spectral subvectors to yield a single spectral vector.

242. The method of claim 198 further comprising decomposing the extracted pixels into a set of discretes extracted objects, wherein each discrete extracted object is transformed into a spectral representation.

243. The method of claim 198 further comprising removing pixels that do not pertain to an object of interest prior to the pixel extraction step.

244. The method of claim 198 further comprising utilizing a logarithmic spiral to estimate a local background of an interest.

245. The method of claim 198 wherein the microarray is chosen from a group comprising: hybridized spotted cDNA microarrays, synthesized oligonucleotide arrays, spotted oligonucleotide arrays peptide nucleotide assays, single nucleotide polymorphism (SNP) arrays, carbohydrate arrays, glycoprotein arrays, protein arrays, proteomic arrays, tissue arrays, antibody arrays, antigen arrays, bioassays, sequencing microarrays, sequencing by hybridization (SBH) microarrays, siRNA duplexes, RNAi arrays glass-based arrays, nylon membrane arrays, thin film arrays, polymer-substrate arrays, capillary electrophoresis arrays, genospectral arrays, electronic arrays, bead arrays, quantum dot arrays, and glycan array.

246. The method of claim 198 wherein the output pattern is representative of an indicator chosen from a group comprising: fluorescence, chemiluminescence, bioluminescence, and photoluminescence.

247. The method of claim 198 further comprising registering the pixels within the output pattern to approximate location of the objects of interest.

248. The method of claim 198 further comprising adjusting contrast of the output pattern.

249. The method of claim 248 wherein the contrast is adjusted using a filter from a group comprising: Gabor filters, low-pass band-pass filters, high-pass band-pass filters, edge detection operators, Laplacian filters, and gradient-focusing filters.

250. A computer code product, embodied on a computer-readable media, that characterizes information from a pixellated output pattern of microarray representing one or more objects of interest, comprising:

computer code that segments the objects of interest within the output pattern using tessellation;

computer code that extracts spatial data elements within the output pattern representative of each object of interest; and computer code that transform an intensity representation of the extracted pixels to a spectral representation.

251. A computer system for characterizing information from a pixellated output pattern of a microarray representing one or more objects of interest, comprising: a processor; and a memory coupled to said processor, said memory encoding one or more programs, said one or more programs causing said processor to perform the following steps:

segmenting the objects of interest within the output pattern using tessellation;

extracting spatial data element within the output pattern representative of each object of interest; and transforming an intensity representation of the extracted pixels to a spectral representation.

252. A system for analyzing an output pattern of an array detectors, each detector representing one or more objects of interest, comprising:

tessellation means for segmenting the objects of interest within the output pattern;

means for extracting spatial data elements within the output pattern representative of each object of interest; and means for transforming an intensity representation of the extracted pixels to a spectral representation.

253. A method for characterizing information from a pixellated output pattern of a microarray having one or more objects of interest, the method comprising:

extracting pixels within the output pattern representative of each object of interest utilizing a radial spiral;

using means for transforming an intensity representation of the extracted pixels to a spectral representation; and associating the extracted pixels with one or more objects of interest.

254. The method of claim 253 wherein the logarithmic spiral uses tessellated extraction mask.

255. The method of claim 254 wherein the tessellated extraction mask is a texture mask.

256. The method of claim 255 wherein the texture mask is chosen from a group comprising: Bernoulli spiral masks, logistique masks, Hirschorn masks, Voderberg masks, bent-wedge tile masks, kinked tile masks, rhomboidal tile masks, triangular tile masks, equiangular spiral masks, symmetric tessellation masks, asymmetric tessellation masks, and spiral mirabilis masks.

257. The method of claim 253 further comprising computationally re-scaling the extracted pixels to increase spatial resolution of the extracted pixels prior to the step of transforming the intensity representation.

258. The method of claim 257 wherein the step of computationally re-scaling the extracted pixels comprises convolving the extracted pixels with a kernel.

259. The method of claim 258 wherein the kernel is a discretized kernel.

260. The method of claim 259 wherein discretized coefficients of the kernel are chosen from a group comprising: linear functions, non-linear functions, and canonical kernel functions.

261. The method of claim 257 wherein the step of computationally re-scaling the extracted pixels comprises a product a scalar dot product with an affine transformation, or a linear function.

262. The method of claim 257 wherein the spatial resolution is increased by convolution of the extracted pixels with a canonical coefficient kernel that yields two or more modified pixels for each extracted pixel.

263. The method of claim 257 wherein the computational re-scaling of the extracted pixels utilizes a cascade of computational convolutions with discretized canonical kernel functions, with each successive convolution conducted on the results of preceding convolution.

264. The method of claim 257 wherein the convolution cascade is chosen from a group comprising: a serial cascade is a parallel cascade, and a combination of a serial cascade and a parallel cascade.

265. The method of claim 253 wherein the output pattern comprises on array of spatially contiguous pixels and the step of extracting pixels further comprises determining which pixels are representative of each object of interest.

266. The method of claim 265 wherein the step of determining which pixels are representative of each object of interest is based on information-theory or an information measure.

267. The method of claim 253 wherein the output pattern comprises array of spatially contiguous pixels and the step of extracting pixels further comprises determining which pixels associated with a morphological representation represent an object of interest.

268. The method of claim 253 wherein the output pattern comprises an array spatially contiguous pixels and the step of extracting pixels further comprises determining which pixels associated with an object of interest represent a morphological invariant.

269. The method of claim 253 further comprising transforming a domain of the extracted pixels from spatial intensity to spatial frequency.

270. The method of claim 253 wherein the step of transforming the intensity representation of the extracted pixels to a spectral representation uses a Fourier transform.

271. The method of claim 270 wherein the Fourier transform is either a Fast Fourier Transform, or a Discrete Fourier Transform.

272. The method of claim 270 further comprising partitioning a spectral vector representing the transformed pixels into non-overlapping subvectors prior to convolving with discretized coefficients of a function.

273. The method of claim 270 further comprising partitioning a spectral vector representing the transformed pixels into overlapping spectral vectors prior to convolving with discretized coefficients of a function.

274. The method of claim 270 further comprising decomposing a spectrally transformed vector into subvectors associated with an object of interest.

275. The method of claim 274 wherein each subvector is convolved with a resolution enhancement kernel.

276. The method of claim 274 wherein the convolved subvectors are computationally re-sampled.

277. The method of claim 276 further comprising combining the post-convolution computationally re-sampled transformed spectral subvectors to yield a single spectral vector.

278. The method of claim 253 further comprising decomposing the extracted pixels into a set of discrete extracted objects, wherein each discrete extracted object is transformed into a spectral representation.

279. The method of claim 270 further comprising estimating a power spectral density from a spectral representation of the extracted pixels.

280. The method of claim 253 further comprising removing pixels that do not pertain to an object of interest prior to the pixel extraction step.

281. The method of claim 253 further comprising utilizing a logarithmic spiral to estimate a local background of an interest.

282. The method of claim 253 wherein the microarray is chosen from a group comprising: hybridized spotted cDNA microarrays, synthesized oligonucleotide arrays, spotted oligonucleotide arrays, peptide nucleotide assays, single nucleotide polymorphism (SNP) arrays, carbohydrate arrays, glycoprotein arrays, protein arrays, proteomic arrays, tissue arrays, antibody arrays, antigen arrays, bioassays, sequencing microarrays, sequencing by hybridization (SBH) microarrays, siRNA duplexes, RNAi arrays glass-based arrays, nylon membrane arrays, thin film arrays, polymer-substrate arrays, capillary electrophoresis arrays, genospectral arrays, electronic arrays, bead arrays, quantum dot arrays, and glycan arrays.

283. The method of claim 253 wherein the output pattern is representative of an indicator chosen from a group comprising: fluorescence, chemiluminescence, bioluminescence, and photoluminescence.

284. The method of claim 253 further comprising registering the pixels within the output pattern to approximate location of the objects of interest.

285. The method of claim 253 further comprising adjusting contrast of the output pattern.

286. The method of claim 285 wherein the contrast is adjusted using a filter from a group comprising: Gabor filters, low-pass band-pass filters, high-pass band-pass filters, edge detection operators, Laplacian filters, and gradient-focusing filters.

287. The method of claim 253 further comprising segmenting the objects of interest within the output pattern prior to the extraction step.

288. The method of claim 253 wherein the using step is dependent upon the expected signal level for each object of interest.

289. A computer code product, embodied on a computer-readable media, that characterizes information from a pixellated output pattern of microarray representing one or more objects of interest, comprising:

computer code that extracts pixels within the output pattern representative of each object of interest using a logarithmic spiral;

computer code that uses means for transforming the intensity representation of the extracted pixels to a spectral representation; and computer code that associates the extracted pixels with one or more objects of interest.

290. A computer system for characterizing information from a pixellated output pattern of a microarray representing one or more objects of interest, comprising: a processor; and a memory coupled to said processor, said memory encoding one or more programs, said one or more programs causing said processor to perform the following steps:

extracting spatial within the output pattern representative of each object of interest using a logarithmic spiral;

using means for transforming an intensity representation of the extracted pixels to a spectral representation; and associating the extracted pixels with one or more objects of interest.

291. A system for analyzing an output pattern of an array of detectors each detector representing one or more objects of interest, comprising:

means for extracting within the output pattern representative of each object of interest using a logarithmic spiral;

means for transforming an intensity representation of the extracted pixels to a spectral representation; and means associating the extracted pixels with one or more objects of interest.

292. A method for characterizing information from a pixellated output pattern of a microarray having one or more object of interest, the method comprising:

extracting pixels within the output pattern representative of each object of interest;

utilizing a logarithmic spiral to estimete a local background of an object of interest;

using means for transforming an intensity representation of the extracted pixels to a spectral representation; and associating the extracted pixels with one or more objects of interest.

293. A computer code product, embodied on a computer-readable media, that characterizes information from a pixellated output pattern of microarray representing one or more objects of interest, comprising:

computer code that extracts pixels within the output pattern representative of each object of interest;

computer code that utilizes a logarithmic spiral to estimate a local background of an object of interest;

computer code that uses means for transforming an intensity representation of the extracted pixels to a spectral representation; and computer code that associates the extracted pixels with one or more objects of interest.

294. A computer system for characterizing information from a pixellated output pattern of a microarray representing one or more objects of interest, comprising: a processor; and a memory coupled to said processor, said memory encoding one or more programs, said one or more programs causing said processor to perform the following steps:

extracting spatial within the output pattern representative of each object of interest;

utilizing a logarithmic spiral to estimate a local background of an object of interest;

using means for transforming an intensity representation of the extracted pixels to a spectral representation; and associating the extracted pixels with one or more objects of interest.

295. A system for analyzing an output pattern of an array of detectors, each detector representing one or more object of interest, comprising:

means for logarithmically extracting pixels within the output pattern representative each of interest;

means for utilizing a logarithmic to estimate a local background of an object of interest;

means for transforming an intensity representation of the extracted pixels to a spectral representation; and means for associating the extracted pixels with one or more objects of interest.

296. A method for characterizing information from a pixellated output pattern of a microarray having one or more object of interest, the method comprising:

extracting pixels within the output pattern representative of each object of interest using a logarithmic spiral;

using means for transforming an intensity representation of the extracted pixels to a spectral representation; and associating the extracted pixels with one or more objects of interest.

297. A system for characterizing information from a pixellated output pattern of microarray representing one or more objects of interest, the system comprising:

a segmentation module for segmenting the output pattern to approximate the locations of the objects of interest within the output pattern;

a filter module for filtering the segmented output pattern to enhance contrast;

an extraction module for extracting a core of pixels associated with each object of interest;

a resampling module for resampling the extracted core pixels to enhance spatial resolution;

a transformation module for transforming a representation of the resampled extracted core pixels from an intensity domain to a spectral domain;

a convolution module for convolving the transformed spectral domain resampled extracted core pixels with a kernel; and an estimation module for estimating a power spectral density from the convolved transformed spiral domain resampled extracted core pixels.

298. A system for characterizing information from a pixellated output pattern of microarray representing one or more objects of interest, the system comprising:

means for segmenting the output pattern to approximate the locations of the objects of interest within the output pattern;

a filter module for filtering the segmented output pattern to enhance contrast;

means for extracting a core of pixels associated with each object of interest;

a resampling module for resampling the extracted core pixels to enhance spatial resolution;

a transformation module for transforming a representation of the resampled extracted core pixels from an intensity domain to a spectral domain;

a convolution module for convolving the transformed spectral domain resampled extracted core pixels with a kernel; and an estimation module for estimating a power spectral density from the convolved transformed spectral domain resampled extracted core pixels.

299. The system of claim 298, wherein the means for segmenting the output pattern comprises a tessellation segmentation module and the means for extracting a core of pixels comprises an extraction module.

300. The method of claim 298, wherein the means for extracting pixels utilizes an extraction technique from a group comprising: degenerate logarithmic spiral masks, rectilinear masks, row-major extraction, and column-major extraction.

* * * * *